US008546627B2

(12) United States Patent
Gruber et al.

(10) Patent No.: US 8,546,627 B2
(45) Date of Patent: *Oct. 1, 2013

(54) RENEWABLE COMPOSITIONS

(75) Inventors: Patrick R. Gruber, Longmont, CO (US); Matthew W. Peters, Highlands Ranch, CO (US); Josefa M. Griffith, Englewood, CO (US); Yassin Al Obaidi, Somerset, KY (US); Leo E. Manzer, Wilmington, DE (US); Joshua D. Taylor, Evergreen, CO (US); David E. Henton, Midland, MI (US)

(73) Assignee: Gevo, Inc., Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/441,468

(22) Filed: Apr. 6, 2012

(65) Prior Publication Data

US 2012/0259146 A1 Oct. 11, 2012

Related U.S. Application Data

(62) Division of application No. 12/327,723, filed on Dec. 3, 2008, now Pat. No. 8,193,402.

(60) Provisional application No. 60/991,978, filed on Dec. 3, 2007, provisional application No. 60/991,990, filed on Dec. 3, 2007, provisional application No. 61/012,110, filed on Dec. 7, 2007, provisional application No. 61/035,076, filed on Mar. 10, 2008, provisional application No. 61/038,980, filed on Mar. 24, 2008, provisional application No. 61/039,153, filed on Mar. 25, 2008, provisional application No. 61/039,329, filed on Mar. 25, 2008, provisional application No. 61/054,739, filed on May 20, 2008, provisional application No. 61/054,752, filed on May 20, 2008, provisional application No. 61/055,600, filed on May 23, 2008, provisional application No. 61/073,688, filed on Jun. 18, 2008, provisional application No. 61/083,044, filed on Jul. 23, 2008, provisional application No. 61/083,048, filed on Jul. 23, 2008, provisional application No. 61/091,858, filed on Aug. 26, 2008.

(51) Int. Cl.
*C10L 1/04* (2006.01)
*C07C 2/04* (2006.01)
*C07C 15/08* (2006.01)
*C07C 69/82* (2006.01)

(52) U.S. Cl.
USPC ............ 585/240; 585/14; 585/24; 585/407; 44/300; 208/15; 500/76; 500/77

(58) Field of Classification Search
USPC ......................................... 585/240, 407–421
See application file for complete search history.

(56) References Cited

U.S. PATENT DOCUMENTS

| 2,391,188 A | 12/1945 | Patterson |
| 2,391,646 A | 12/1945 | Schulze et al. |

(Continued)

FOREIGN PATENT DOCUMENTS

| GB | 1313083 | 4/1973 |
| JP | 10-237017 A | 9/1998 |

(Continued)

OTHER PUBLICATIONS

"International Preliminary Report on Patentability," 10 pages, International Patent Appl. No. PCT/US2010/025234, United States Patent and Trademark Office (issued Aug. 30, 2011).

(Continued)

*Primary Examiner* — Ellen McAvoy
(74) *Attorney, Agent, or Firm* — Cooley LLP

(57) ABSTRACT

The present invention is directed to renewable compositions derived from fermentation of biomass, and integrated methods of preparing such compositions.

21 Claims, 7 Drawing Sheets

Integrated process to produce renewable jet fuel from biomass.

(56) References Cited

U.S. PATENT DOCUMENTS

| | | |
|---|---|---|
| 2,529,061 A | 11/1950 | Vergnaud |
| 2,554,054 A | 5/1951 | Owen |
| 2,813,119 A | 11/1957 | Taves |
| 2,894,978 A | 7/1959 | Katzschmann |
| 2,945,900 A | 7/1960 | Alexander et al. |
| 2,982,795 A | 5/1961 | Owen |
| 2,984,644 A | 5/1961 | Wheat |
| 3,002,035 A | 9/1961 | Hieronymus |
| 3,154,593 A | 10/1964 | Long |
| 3,301,906 A | 1/1967 | Besozzi et al. |
| 3,344,037 A | 9/1967 | Leavitt |
| 3,356,754 A | 12/1967 | Wofford |
| 3,445,521 A | 5/1969 | Callahan et al. |
| 3,509,237 A | 4/1970 | Aubrey |
| 3,513,193 A | 5/1970 | Katzschmann |
| 3,644,550 A | 2/1972 | Beuther et al. |
| 3,662,016 A | 5/1972 | Furuoya et al. |
| 3,686,341 A | 8/1972 | Eberly |
| 3,755,458 A | 8/1973 | Vrbaski et al. |
| 3,825,502 A | 7/1974 | Takenaka et al. |
| 3,827,968 A | 8/1974 | Givens et al. |
| 3,830,866 A | 8/1974 | D'Alessandro et al. |
| 3,832,418 A | 8/1974 | Bercik et al. |
| 3,836,603 A | 9/1974 | Connor, Jr. et al. |
| 3,850,981 A | 11/1974 | Trebellas et al. |
| 3,851,008 A | 11/1974 | Stowe et al. |
| 3,886,224 A | 5/1975 | Mitchell, Jr. |
| 3,887,612 A | 6/1975 | Shigeyasu et al. |
| 3,891,721 A | 6/1975 | Prudence |
| 3,959,400 A | 5/1976 | Lucki |
| 3,960,978 A | 6/1976 | Givens et al. |
| 3,997,621 A | 12/1976 | Brennan |
| 4,025,575 A | 5/1977 | Chang et al. |
| 4,096,340 A | 6/1978 | Fujii et al. |
| 4,100,220 A | 7/1978 | Bowman et al. |
| 4,112,011 A | 9/1978 | Kolombos |
| 4,129,600 A | 12/1978 | Childress et al. |
| 4,152,300 A | 5/1979 | Riesser |
| 4,190,608 A | 2/1980 | Grasselli et al. |
| 4,197,185 A | 4/1980 | Le Page et al. |
| 4,225,743 A | 9/1980 | Hoshiyama et al. |
| 4,229,320 A | 10/1980 | Slaugh |
| 4,229,603 A | 10/1980 | Lyon |
| 4,241,220 A | 12/1980 | Itaya et al. |
| 4,244,806 A | 1/1981 | Le Page et al. |
| 4,266,958 A | 5/1981 | Cummings |
| 4,293,722 A | 10/1981 | Ward et al. |
| 4,304,948 A | 12/1981 | Vora et al. |
| 4,324,646 A | 4/1982 | Le Page et al. |
| 4,329,493 A | 5/1982 | Hashizume et al. |
| 4,331,823 A | 5/1982 | Wieder et al. |
| 4,342,876 A | 8/1982 | Klingman |
| 4,354,044 A | 10/1982 | Aoshima et al. |
| 4,385,157 A | 5/1983 | Auclair et al. |
| 4,393,259 A | 7/1983 | Ward et al. |
| 4,396,787 A | 8/1983 | Gluzek et al. |
| 4,398,920 A | 8/1983 | Guibet et al. |
| 4,423,267 A | 12/1983 | Dowling et al. |
| 4,448,643 A | 5/1984 | Lindner et al. |
| 4,456,779 A | 6/1984 | Owen et al. |
| 4,456,781 A | 6/1984 | Marsh et al. |
| 4,463,211 A | 7/1984 | Manning |
| 4,465,884 A | 8/1984 | Degnan et al. |
| 4,471,147 A | 9/1984 | Owen et al. |
| 4,499,316 A | 2/1985 | Garska et al. |
| 4,504,692 A | 3/1985 | Arakawa et al. |
| 4,504,693 A | 3/1985 | Tabak et al. |
| 4,518,796 A | 5/1985 | Aoshima et al. |
| 4,531,014 A | 7/1985 | Gregory et al. |
| 4,542,251 A | 9/1985 | Miller |
| 4,544,792 A | 10/1985 | Smith et al. |
| 4,612,406 A | 9/1986 | Long et al. |
| 4,621,164 A | 11/1986 | Chang et al. |
| 4,642,369 A | 2/1987 | Modic et al. |
| 4,663,406 A | 5/1987 | Bronstert et al. |
| 4,698,452 A | 10/1987 | Le Van Mao et al. |
| 4,720,600 A | 1/1988 | Beech, Jr. et al. |
| 4,720,601 A | 1/1988 | Suzukamo et al. |
| 4,740,652 A | 4/1988 | Frame |
| 4,788,376 A | 11/1988 | Mazurek et al. |
| 4,806,701 A * | 2/1989 | Shum ............ 585/417 |
| 4,808,763 A * | 2/1989 | Shum ............ 585/415 |
| 4,855,528 A | 8/1989 | Young et al. |
| 4,864,068 A * | 9/1989 | Shamshoum ............ 585/514 |
| 4,873,392 A | 10/1989 | Le Van Mao |
| 4,908,471 A | 3/1990 | Leuck et al. |
| 4,950,828 A * | 8/1990 | Shum ............ 585/417 |
| 4,975,402 A | 12/1990 | Le van Mao et al. |
| 5,026,938 A * | 6/1991 | Shum ............ 585/417 |
| 5,087,789 A | 2/1992 | McDaniel et al. |
| 5,107,050 A | 4/1992 | Gaffney et al. |
| 5,130,458 A | 7/1992 | Wu |
| 5,135,861 A | 8/1992 | Pavilon |
| 5,386,071 A * | 1/1995 | Kuchar et al. ............ 585/313 |
| 5,414,160 A | 5/1995 | Sato et al. |
| 5,519,101 A | 5/1996 | Nubel et al. |
| 5,550,306 A | 8/1996 | Chauvin et al. |
| 5,625,109 A * | 4/1997 | Gupta ............ 585/639 |
| 5,672,800 A | 9/1997 | Mathys et al. |
| 5,693,793 A | 12/1997 | Ritz et al. |
| 5,753,474 A | 5/1998 | Ramey |
| 5,801,286 A | 9/1998 | Besson et al. |
| 5,856,604 A | 1/1999 | Stine et al. |
| 5,877,372 A | 3/1999 | Evans et al. |
| 5,895,830 A | 4/1999 | Stine et al. |
| 5,962,604 A | 10/1999 | Rath |
| 5,969,178 A | 10/1999 | Okamoto et al. |
| 5,990,367 A | 11/1999 | Stine et al. |
| 5,994,601 A | 11/1999 | Nierlich et al. |
| 6,111,160 A | 8/2000 | Powers et al. |
| 6,143,942 A | 11/2000 | Verrelst et al. |
| 6,239,321 B1 | 5/2001 | Mossman et al. |
| 6,300,536 B1 | 10/2001 | Verrelst et al. |
| 6,323,384 B1 | 11/2001 | Powers et al. |
| 6,331,580 B1 | 12/2001 | Molnar |
| 6,358,717 B1 | 3/2002 | Blaschek et al. |
| 6,376,731 B1 | 4/2002 | Evans et al. |
| 6,600,081 B2 | 7/2003 | Manzer et al. |
| 6,649,757 B2 | 11/2003 | Kuroda et al. |
| 6,660,898 B1 | 12/2003 | Pyhälahti et al. |
| 6,689,927 B1 * | 2/2004 | Frame et al. ............ 585/510 |
| 6,770,791 B2 | 8/2004 | Mathys et al. |
| 6,875,899 B2 | 4/2005 | Martens et al. |
| 6,884,916 B1 | 4/2005 | Brown et al. |
| 7,002,053 B2 | 2/2006 | Nierlich et al. |
| 7,012,167 B2 | 3/2006 | Kahn |
| 7,038,101 B2 | 5/2006 | Nurminen et al. |
| 7,067,708 B2 | 6/2006 | Manzer et al. |
| 7,161,053 B2 | 1/2007 | Beckmann et al. |
| 7,169,588 B2 | 1/2007 | Burch et al. |
| 7,183,450 B2 | 2/2007 | Brown et al. |
| 7,238,844 B2 | 7/2007 | Mathys et al. |
| 7,271,304 B2 | 9/2007 | Du Toit |
| 7,304,196 B2 | 12/2007 | Purola et al. |
| 7,329,788 B2 | 2/2008 | Tiitta et al. |
| 7,345,212 B2 | 3/2008 | Beadle et al. |
| 7,439,409 B1 | 10/2008 | Jan et al. |
| 7,498,473 B2 * | 3/2009 | Zhou et al. ............ 585/417 |
| 7,553,997 B2 * | 6/2009 | Stark et al. ............ 585/275 |
| 7,682,811 B2 * | 3/2010 | Leschine et al. ............ 435/161 |
| 7,833,778 B2 * | 11/2010 | Butler, III ............ 435/252.7 |
| 8,193,402 B2 * | 6/2012 | Gruber et al. ............ 585/240 |
| 2002/0183578 A1 | 12/2002 | Commereuc et al. |
| 2003/0055179 A1 | 3/2003 | Ota et al. |
| 2004/0044261 A1 | 3/2004 | Feng et al. |
| 2005/0069998 A1 | 3/2005 | Ballesteros Perdices et al. |
| 2005/0112739 A1 | 5/2005 | Golubkov |
| 2005/0176870 A1 | 8/2005 | Kulkarni et al. |
| 2005/0183325 A1 | 8/2005 | Sutkowski |
| 2005/0228203 A1 | 10/2005 | Manzer |
| 2005/0228204 A1 | 10/2005 | Manzer |
| 2006/0111599 A1 | 5/2006 | Lamprecht et al. |
| 2007/0039239 A1 | 2/2007 | Forester et al. |
| 2007/0092957 A1 | 4/2007 | Donaldson et al. |

| | | | |
|---|---|---|---|
| 2007/0135665 | A1 | 6/2007 | Wiese et al. |
| 2007/0148751 | A1 | 6/2007 | Griffin et al. |
| 2007/0191662 | A1 | 8/2007 | Oikarinen et al. |
| 2007/0202062 | A1 | 8/2007 | Workman et al. |
| 2007/0215519 | A1 | 9/2007 | Dierickx |
| 2007/0259410 | A1 | 11/2007 | Donaldson et al. |
| 2007/0259411 | A1 | 11/2007 | Bramucci et al. |
| 2007/0264697 | A1* | 11/2007 | Taguchi et al. ............... 435/167 |
| 2007/0292927 | A1 | 12/2007 | Donaldson et al. |
| 2008/0009656 | A1 | 1/2008 | D'Amore et al. |
| 2008/0015395 | A1 | 1/2008 | D'Amore et al. |
| 2008/0015397 | A1 | 1/2008 | D'Amore et al. |
| 2008/0045754 | A1 | 2/2008 | D'Amore et al. |
| 2008/0057555 | A1* | 3/2008 | Nguyen ........................ 435/165 |
| 2008/0124774 | A1 | 5/2008 | Bramucci et al. |
| 2008/0131948 | A1 | 6/2008 | Manzer et al. |
| 2008/0132730 | A1 | 6/2008 | Manzer et al. |
| 2008/0132732 | A1 | 6/2008 | Manzer et al. |
| 2008/0132741 | A1 | 6/2008 | D'Amore et al. |
| 2008/0138870 | A1 | 6/2008 | Bramucci et al. |
| 2008/0182308 | A1 | 7/2008 | Donaldson et al. |
| 2008/0220488 | A1 | 9/2008 | D'Amore et al. |
| 2008/0227940 | A1 | 9/2008 | Wilson et al. |
| 2008/0234523 | A1 | 9/2008 | Manzer et al. |
| 2008/0248540 | A1 | 10/2008 | Yang |
| 2008/0261230 | A1 | 10/2008 | Liao et al. |
| 2008/0274525 | A1 | 11/2008 | Bramucci et al. |
| 2008/0312482 | A1 | 12/2008 | Jan et al. |
| 2008/0312485 | A1 | 12/2008 | Takai et al. |
| 2009/0030239 | A1 | 1/2009 | D'Amore et al. |
| 2009/0061492 | A1* | 3/2009 | Benning et al. ............... 435/134 |
| 2009/0068714 | A1* | 3/2009 | Leschine et al. ............. 435/161 |
| 2009/0099401 | A1 | 4/2009 | D'Amore et al. |
| 2009/0155869 | A1* | 6/2009 | Buelter et al. ................ 435/160 |
| 2009/0171129 | A1 | 7/2009 | Evanko et al. |
| 2009/0182163 | A1 | 7/2009 | Foo et al. |
| 2009/0215137 | A1 | 8/2009 | Hawkins et al. |
| 2009/0226990 | A1 | 9/2009 | Hawkins et al. |
| 2009/0226991 | A1 | 9/2009 | Feldman et al. |
| 2009/0239009 | A1 | 9/2009 | Tanaka |
| 2009/0240068 | A1 | 9/2009 | Rajendran |
| 2009/0247799 | A1 | 10/2009 | Myllyoja et al. |
| 2009/0299109 | A1 | 12/2009 | Gruber et al. |
| 2010/0108568 | A1 | 5/2010 | De Klerk |
| 2010/0137647 | A1* | 6/2010 | Bradin ........................ 568/382 |
| 2010/0216958 | A1 | 8/2010 | Peters et al. |
| 2011/0087000 | A1 | 4/2011 | Peters et al. |
| 2011/0172475 | A1 | 7/2011 | Peters et al. |
| 2011/0288311 | A1* | 11/2011 | Frost et al. .................... 549/244 |
| 2011/0288352 | A1 | 11/2011 | Peters et al. |
| 2012/0171741 | A1 | 7/2012 | Peters et al. |
| 2012/0238787 | A1* | 9/2012 | Gruber et al. ................... 585/14 |

FOREIGN PATENT DOCUMENTS

| | | |
|---|---|---|
| JP | 2001-2600 A | 1/2001 |
| JP | 2006-306731 A | 11/2006 |
| JP | 2007-61763 A | 3/2007 |
| WO | WO 03/053570 A1 | 7/2003 |
| WO | WO 03/070671 A1 | 8/2003 |
| WO | WO 2005/065393 A2 | 7/2005 |
| WO | WO 2005/073172 A1 | 8/2005 |
| WO | WO 2005/092821 A1 | 10/2005 |
| WO | WO 2007/091862 | 8/2007 |
| WO | WO 2008/058664 A1 | 5/2008 |
| WO | WO 2008/113492 A1 | 9/2008 |
| WO | WO 2009/038965 A1 | 3/2009 |
| WO | WO 2009/039000 A2 | 3/2009 |
| WO | WO 2009/039333 A1 | 3/2009 |
| WO | WO 2009/039335 A1 | 3/2009 |
| WO | WO 2009/039347 A1 | 3/2009 |

OTHER PUBLICATIONS

"International Search Report," 2 pages, from International Appl. No. PCT/US2010/051641, United States Patent and Trademark Office, Alexandria, Virginia, USA (mailed Dec. 2, 2010).

"International Search Report," 2 pages, from PCT appl. No. PCT/US2011/020549, United States Patent and Trademark Office, Alexandria, Virginia, United States (mailed Mar. 11, 2011).

"International Search Report," 2 pages, International Patent Appl. No. PCT/US2011/035769, United States Patent and Trademark Office (Aug. 17, 2011).

"International Search Report," 2 pages, International Patent Appl. No. PCT/US2011/058766, United States Patent and Trademark Office (Feb. 17, 2012).

"International Search Report," 5 pages, International Patent Appl. No. PCT/US2010/025234, United States Patent and Trademark Office (mailed Jun. 15, 2010).

"Written Opinion of the International Searching Authority," 5 pages, International Patent Appl. No. PCT/US2011/035769, United States Patent and Trademark Office (Aug. 17, 2011).

"Written Opinion of the International Searching Authority," 5 pages, International Patent Appl. No. PCT/US2011/058766, United States Patent and Trademark Office (Feb. 17, 2012).

"Written Opinion of the International Searching Authority," 7 pages, from International Appl. No. PCT/US10/51641, United States Patent and Trademark Office, Alexandria, Virginia, USA (mailed Dec. 2, 2010).

"Written Opinion of the International Searching Authority," 9 pages, International Patent Appl. No. PCT/US2010/025234, United States Patent and Trademark Office (mailed Jun. 15, 2010).

"Written Opinion of the International Searching Authority," 9 pages, from PCT appl. No. PCT/US11/20549, United States Patent and Trademark Office, Alexandria, Virginia, United States (mailed Mar. 11, 2011).

Angermayr et al., "Energy Biotechnology with Cyanobacteria" Current Opinion in Biotechnology Jun. 2009, vol. 20, pp. 257-263.

Atsumi "Direct photosynthetic recycling of carbon dioxide to isobutyraldehyde" Nature Biotechnology, Nov. 15, 2009, vol. 27, pp. 1177-1182.

Batist et al. "The catalytic oxidation of 1-butene over bismuth molybdate catalysts: II. Dependence of activity and selectivity on the catalyst composition" Journal of Catalysis, Feb. 1966, vol. 5, pp. 55-64.

Bekker and Prinsloo, "Butene Oligomerization over Phosphoric Acid: Structural Characterization of Products," Ind. Eng. Chem. Res. 48(22):10156-10162 (2009).

Bezergianni et al., "Catalytic Hydrocracking of Fresh and Used Cooking Oil," Ind. Eng. Chem. Res. 48:8402-8406 (2009).

Buyanov et al. "Catalysts and Processes for Paraffin and Olefin Dehydrogenation," Kinetics and Catalysis, Jan. 2001, vol. 42, pp. 64-75.

Connor et al. "Engineering of an *Escherichia coli* Strain for the Production of 3-Methyl-1-Butanol" Applied Envirionmental Microbiology, Sep. 2008, vol. 74, pp. 5769-5775.

de Klerk, "Can Fischer-Tropsch Syncrude Be Refined to On-Specification Diesel Fuel?" Energy Fuels 23:4593-4604 (2009).

de Klerk, "Distillate Production by Oligomerization of Fischer-Tropsch Olefins over Solid Phosphoric Acid," Energy Fuels 20:439-445 (2006).

de Klerk, "Fischer-Tropsch Refining," Title page and pp. i-xi, Ph.D. Thesis, University of Pretoria (Feb. 2008).

de Klerk, "Fischer-Tropsch refining: technology selection to match molecules," Green Chem. 10:1249-1279 (2008).

Delhomme et al. "Succinic acid from renewable resources as a C4 building-block chemical—a review of the catalytic possibilities in aqueous media" Green Chemistry, Jan. 2009, vol. 11(1), pp. 13-26.

Dexter et al. "Metabolic Engineering of Cyanobacteria for Ethanol Production" Energy & Environmental Science, Aug. 2009, vol. 2(8), pp. 857-864.

Dhaliwal et al. "Measurement of the Unsaturation of Butyl Rubbers by the Iodine Index Method" Rubber Chemistry and Technology, 1994, vol. 67, pp. 567-581.

Genomatica, Inc. press release, 10 pages (2008/2009).

Hileman et al., "Near-Term Feasibility of Alternative Jet Fuels," 152 pages, RAND Corporation, 2009.

Jung et al. "Oxidative Dehydrogenation of $C_4$ Raffinate-3 to 1,3-Butadiene in a Dual-bed Reaction System Comprising $ZnFe_2O_4$ and $Co_9Fe_3Bi_1Mo_{12}O_{13.51}$ Catalysts: A Synergistic Effect of $ZnFe_2O_4$ and $Co_9Fe_3Bi_1Mo_{12}O_{51}$ Catalysts" Catalysis Letters, Jul. 2008 vol. 123, pp. 239-245.

Kamath "Process Analysis for Dimerization of Isobutene by Reactive Distillation" Industrial & Engineering Chemistry Research, Feb. 1, 2006, vol. 45, pp. 1575-1582.

Krishnan et al. "Oxidative Dehydrogenation of 1-Butene over Manganese Oxide Octahedral Molecular Sieves" Journal of Catalysis, Jun. 1999, vol. 184, pp. 305-315.

Latshaw "Dehydration of Isobutane to Isobutene in a Slurry Reactor" Department of Energy Topical Report, 84 pages, Feb. 1994.

Lopez Nieto et al. "Selective Oxidation of n-Butane and Butenes over Vanadium-Containing Catalysts" Journal of Catalysis, Jan. 2000, vol. 189, pp. 147-157.

McAvoy, "Office Action Summary," 7 pages, U.S. Appl. No. 13/441,459 (mailed Jul. 20, 2012).

Pines and Haag, "Alumina: Catalyst and Support. IX. The Alumina Catalyzed Dehydration of Alcohols," J. Am. Chem. Soc. 83:2847-2852 (1961).

Rossberg et al., "Chlorinated Hydrocarbons," in Ullmann's Encyclopedia of Industrial Chemistry 2002, Wiley VCH, published online Jul. 15, 2006.

Rumizen, "ASTM Aviation Synthetic Fuel Specification," $3^{rd}$ International Conference on Biofuel Standards, World Biofuels Markets Congress, 19 pages (Mar. 2010).

Saad et al., "Characterization of various zinc oxide catalysts and their activity in the dehydration-dehydrogenation of isobutanol" Journal of the Serbian Chemical Society 2008, vol. 73(10), pp. 997-1009.

Syu, "Biological production of 2,3-butanediol" Applied Microbiology and Biotechnology, Jan. 2001, vol. 55(1), pp. 10-18.

Threadingham et al., "Rubber, 3. Synthetic," in Ullmann's Encyclopedia of Industrial Chemistry 2002, Wiley VCH, published online Apr. 30, 2004.

Tiwari et al. "Effect of aluminium oxide on the properties of Cu-Mo catalyst in the oxidative dehydrogenation of butene-1 to butadiene" Journal of Catalysis, Nov. 1989, vol. 120, pp. 278-281.

Toledo-Antonio et al. "Correlation between the magnetism of non-stoichiometric zinc ferrites and their catalytic activity for oxidative dehydrogenation of 1-butene" Applied Catalysis A: General, Aug. 2002, vol. 234, pp. 137-144.

"International Search Report," 4 pages, International Patent Application No. PCT/US2008/085423, United States Patent and Trademark Office, Alexandria, Virginia, United States (mailed Jul. 15, 2009).

"Part 2, Oxidative Dehydrodimerization of Alkenes", Catalysis Today, (1992), 343-393.

"Written Opinion of the International Searching Authority," 6 pages, International Patent Application No. PCT/US2008/085423, United States Patent and Trademark Office, Alexandria, Virginia, United States (mailed Jul. 15, 2009).

Amin et al., "Dealuminated ZSM-5 Zeolite Catalyst for Ethylene Oligomerization to Liquid Fuels", Journal of Natural Gas Chemistry 2002, 11, 79-86.

ASTM International, "Standard Specification for Automotive Spark-Ignition Engine Fuel," Designation D4814-11, 31 pages (Jul. 2011).

ASTM International, "Standard Specification for Aviation Gasolines," Designation D910-11, 8 pages (May 2011).

ASTM International, "Standard Specification for Aviation Turbine Fuels," Designation D1655-11a, 16 pages (Aug. 2011).

ASTM International, "Standard Specification for Diesel Fuel Oils," Designation D975-11, 25 pages (Apr. 2011).

ASTM test method D 6866-05, "Determining the Biobased Content of Natural Range Materials Using Radiocarbon and Isotope Ratio Mass Spectrometry Analysis".

Atsumi et al., "Non-fermentative Pathways for Synthesis of Branched-Chain Higher Alcohols as Biofuels", Nature, 2008, 451, p. 86-89.

Atsumi et al., Online Supplementary Information of "Non-fermentative Pathways for Synthesis of Branched-Chain Higher Alcohols as Biofuels", Nature, 2008, pp. 1-8.

Busca, "Acid Catalysts in Industrial Hydrocarbon Chemistry" Chemical Reviews, 2007, 107, 5366-5410.

Čaejka et al., "Acid-Catalyzed Sythesis of Mono- and Dialkyl Benzenes over Zeolites: Active Sites, Zeolite Topology, and Reaction Mechanisms", Catalysis Review 2002, 44(3), 375-421.

Chen and Yan, "M2 Forming — A Process for Aromatization of Light Hydrocarbons", Ind. Eng. Chem. Process Des. Dev., 25 (1986), 151-155.

Frame et al., "High Octane Gasoline from Field Butanes by the UOP Indirect Alkylation (InAlk) Process", Erdöl, Erdgas Kohle, 114(7-8) (1998), 385-387.

Gnep et al., "Conversion of Light Alkanes to Aromatic Hydrocarbons; II. Role of Gallium Species in Propane Transformation on GaHZSM5 Catalysts", Applied Catalysis 1988, 43, 155.

Guisnet et al., "Aromatization of short chain alkanes on zeolite catalysts," Appl. Catal. A, 1992, 89, p. 1-30.

Hobbie et al., "Intramolecular, compound-specific, and bulk carbon isotope patterns in $C_3$ and $C_4$ plants: a review and synthesis," New Phytologist, 2004, 161, p. 371-385.

Lamprecht, "Fischer-Tropsch Fuel for Use by the U.S. Military as Battlefield-Use Fuel of the Future", Energy & Fuels 2007, 21, 1448-1453.

Mazumder et al., "Oxidative Dehydrodimerization and Aromatization of Isobutene on $Bi_2 O_3$-$SnO_2$ Catalysts", Applied Catalysis A: General, 245 (2003), 87-102.

McAvoy, "Notice of Allowability," 5 pages, U.S. Appl. No. 12/327,723 (mailed Mar. 9, 2012).

McAvoy, "Office Action Summary," 5 pages, U.S. Appl. No. 12/327,723 (mailed Jan. 4, 2012).

McAvoy, "Office Action Summary," 7 pages, U.S. Appl. No. 12/327,723 (mailed Jan. 11, 2011).

McAvoy, "Office Action Summary," 8 pages, U.S. Appl. No. 12/327,723 (mailed Apr. 8, 2011).

McAvoy, "Supplemental Notice of Allowability," 4 pages, U.S. Appl. No. 12/327,723 (mailed Apr. 27, 2012).

Sakuneka et al., "Synthetic Jet Fuel Production by Combined Propene Oligomerization and Aromatic Alkylation over Solid Phosphoric Acid", Ind. Eng. Chem. Res., 47 (2008), 1828-1834.

Savidge et al., "Intramolecular Carbon Isotopic Composition of Monosodium Glutamate: Biochemical Pathways and Product Source Identification," J. Agric. Food Chem. 2005, 53, p. 197-201.

Schmidt, "Fundamentals and systematics of the non-statistical distributions of isotopes in natural compounds," Naturwissenschaften 2003, 90, p. 537-552.

Solymosi et al., Aromatization of Isobutane and Isobutene Over $Mo_2C$/ZSM-5 Catalyst, Applied Catalysis A: General, 278 (2004), 111-121.

Speiser et al., "Catalytic Ethylene Dimerization and Oligomerization: Recent Developments with Nickel Complexes Containing P,N-Chelating Ligands", Accounts of Chemical Research 2005, 38, 784-793.

Subramani et al., "A Review of Recent Literature to Search for an Efficient Catalytic Process for the Conversion of Syngas to Ethanol", Energy and Fuels, 2008, 22, p. 814-839.

Suresh et al., "Engineering Aspects of Industrial Liquid-Phase Air Oxidation of Hydrocarbons", Ind. Eng. Chem. Res. 39 (2000), 3958-3997.

Taubert et al., "Dehydrodimerization of Isobutene to 2,5-Dimethyl-1,5-hexadiene over Bismuth-(III)-Oxide and Various Additives", Chem. Eng. Technol., 29(4) (2006), 468-472.

UOP, "Cyclar™" (process fact sheet).

UOP, UOP Indirect Alkylation (InAlk™) Process Mixed Olefins Application (process fact sheet).

Weber et al., "13C-Pattern of Natural Glycerol: Origin and Practical Importance," J. Agric. Food Chem. 1997, 45, p. 2042-2046.

Wyman, "Potential Synergies and Challenges in Refining Cellulosic Biomass to Fuels, Chemicals, and Power", 2003 Biotechnological Progress 19:254-62.

\* cited by examiner

Schematic of combined oligomerization and aromatic alkylation in one pot.

Comparison of Petroleum-Derived Gasoline and a Renewable Gasoline

Fig.4
Comparison of Petroleum-Derived Jet Fuel and a Renewable Jet Fuel
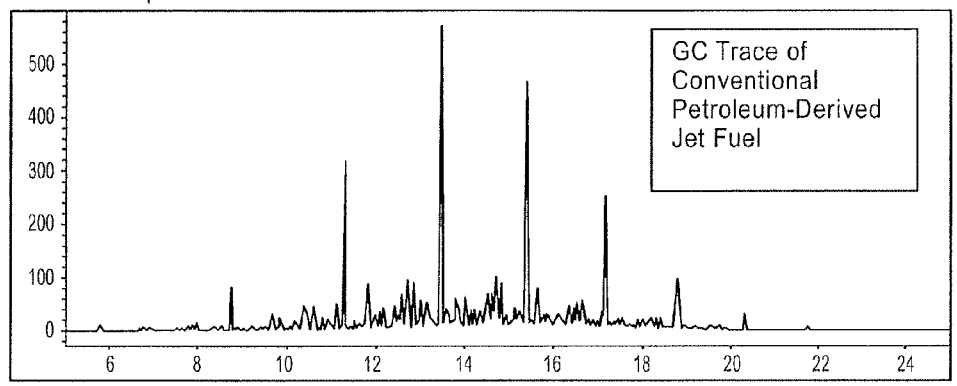
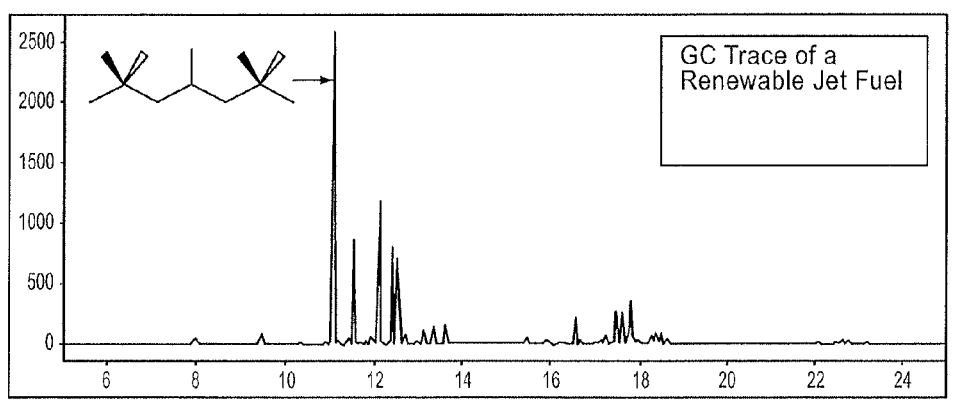

Fig. 7

Comparison of Various Properties Of Petroleum-Derived Diesel Fuel and a Renewable Diesel Fuel

|  | Petroleum-Derived Diesel Fuel | Renewable Diesel Fuel |
| --- | --- | --- |
| Boiling Point (°C) | 150-360 | 150-250 |
| Flash Point (°C) | >38 | 51 |
| Cloud Point (°C) | -40 to 0 (seasonal by state) | < -40 |
| Cetane Number | >40 | 68 |
| Sulfur Content (ppm) | >15 | 0 |
| Aromatic (%) | 25-30 | 0 |

RENEWABLE COMPOSITIONS

CROSS REFERENCE TO RELATED APPLICATIONS

This application is a divisional application of U.S. patent application Ser. No. 12/327,723, filed on Dec. 32008, now U.S. Pat. No. 8,193,402 which claims priority to U.S. Provisional Appl. No. 60/991,978, filed Dec. 3, 2007; U.S. Provisional Appl. No. 60/991,990, filed Dec. 3, 2007; U.S. Provisional Appl. No. 61/012,110, filed Dec. 7, 2007; U.S. Provisional Appl. No. 61/035,076, filed Mar. 10, 2008; U.S. Provisional Appl. No. 61/038,980, filed Mar. 24, 2008; U.S. Provisional Appl. No. 61/039,153, filed Mar. 25, 2008; U.S. Provisional Appl. No. 61/039,329, filed Mar. 25, 2008; U.S. Provisional Appl. No. 61/054,739, filed May 20, 2008; U.S. Provisional Appl. No. 61/054,752, filed May 20, 2008; U.S. Provisional Appl. No. 61/055,600, filed May 23, 2008; U.S. Provisional Appl. No. 61/073,688, filed Jun. 18, 2008; U.S. Provisional Appl. No. 61/083,044, filed Jul. 23, 2008; U.S. Provisional Appl. No. 61/083,048, filed Jul. 23, 2008; and U.S. Provisional Appl. No. 61/091,858, filed Aug. 26, 2008. Each of the above applications is herein incorporated by reference in its entirety for all purposes.

BACKGROUND OF THE INVENTION

Conventional transportation fuels and many fine chemicals (e.g. monomers, polymers, plasticizers, adhesives, thickeners, aromatic and aliphatic solvents, etc.) are typically derived from non-renewable raw materials such as petroleum. However, there is increasing concern that the use of petroleum as a basic raw material contributes to environmental degradation (e.g., global warming, air and water pollution, etc.) and fosters overdependence on unreliable petroleum supplies from politically unstable parts of the world.

For example, burning a gallon of typical gasoline produces over 19 pounds of carbon dioxide. Because no carbon dioxide is consumed by a refinery in the manufacture of gasoline, the net carbon dioxide produced is always at least as great as the amount of carbon contained in the fuel. In addition, the net carbon dioxide produced by burning a gallon of petroleum-based gasoline can be even higher when the combustion of additional fossil fuels required to power the refinery and the transportation vehicles that bring the fuel to market are considered. In contrast to fossil fuels, when biomass is converted into biofuels, carbon dioxide is removed from the atmosphere. In contrast for a biofuel process, it is possible and probable that the net carbon dioxide of burning a gallon of biofuel is less than the carbon dioxide corresponding to the carbon atoms in the biofuel. Thus, a defining feature of biofuels and biofuel blends is that the net carbon dioxide produced by burning a gallon of biofuel or biofuel blend is less than the net carbon dioxide produced by burning a gallon of gasoline. Thus, biofuels and biomass-derived organic chemical materials provide significant environmental benefits. There is thus a need to identify new renewable sources of raw materials useful for e.g. transportation fuels and as raw materials for the chemical industry, which are scalable and cost-competitive with conventional sources.

Market fluctuations in the 1970s, due to the Arab oil embargo and the Iranian revolution, coupled with the decrease in US oil production led to an increase in crude oil prices and a renewed interest in renewable materials. Today, many interest groups including policy makers, industry planners, aware citizens, and the financial community are interested in replacing or supplementing petroleum-derived fuels with biomass-derived biofuels. One leading motivation for developing biofuels is economic, namely the concern that the consumption rate of crude oil may soon exceed the supply rate, thus leading to significantly increased fuel cost.

Biofuels are renewable transportation fuels which have a long history ranging back to the beginning on the 20th century. As early as 1900, Rudolf Diesel demonstrated an engine running on peanut oil. Soon thereafter, Henry Ford demonstrated his Model T running on ethanol derived from corn. However, petroleum-derived fuels displaced biofuels in the 1930s and 1940s due to increased supply and efficiency at a lower cost.

At present, biofuels tend to be produced using local agricultural resources in many relatively small facilities, and are viewed as providing a stable and secure supply of fuels independent of the geopolitical problems associated with petroleum. At the same time, biofuels can enhance the agricultural sector of national economies. In addition, environmental concerns relating to the possibility of carbon dioxide related climate change is an important social and ethical driving force which is triggering new government regulations and policies such as caps on carbon dioxide emissions from automobiles, taxes on carbon dioxide emissions, and tax incentives for the use of biofuels.

The acceptance of biofuels depends primarily on their economical competitiveness compared to petroleum-derived fuels. As long as biofuels are more expensive than petroleum-derived fuels, the use of biofuels will be limited to specialty applications and niche markets. Today, the primary biofuels are ethanol and biodiesel. Ethanol is typically made by the fermentation of corn in the US and from sugar cane in Brazil. Ethanol from corn or sugar cane is competitive with petroleum-derived gasoline (exclusive of subsidies or tax benefits) when crude oil stays above $50 per barrel and $40 per barrel, respectively. Biodiesel is competitive with petroleum-based diesel when the price of crude oil is $60/barrel or more.

In addition to cost, the acceptance of biofuels is predicated on their performance characteristics, their ability to run in many types of existing equipment, and their ability to meet demanding industry specifications that have evolved over the last century. Fuel ethanol has achieved only limited market penetration in the automotive market in part due to its much lower energy content compared to gasoline, and other properties (such as water absorption) that hinder its adoption as a pure fuel. To date, the maximum percentage of ethanol used in gasoline has been 85% (the E85 grade), and this has found use in only a small fraction of newer, dual-fuel cars where the engines have been redesigned to accommodate the E85 fuel.

Acceptance of biofuels in the diesel industry and aviation industry has lagged even farther behind that of the automotive industry. Methyl trans-esterified fatty acids from seed oils (such as soybean, corn, etc.) have several specific disadvantages compared to petroleum-derived diesel fuels, particularly the fact that insufficient amounts of seed oil are available. Even under the most optimistic scenarios, seed oils could account for no more than 5% of the overall diesel demand. Furthermore, for diesel and aviation engines, the cold flow properties of the long chain fatty esters from seed oils are sufficiently poor so as to cause serious operational problems even when used at levels as low as 5%. Under cold conditions, the precipitation and crystallization of fatty paraffin waxes can cause debilitating flow and filter plugging problems. For aviation engines, the high temperature instability of the esters and olefinic bonds in seed oils is also a potential problem. To use fatty acid esters for jet fuel, the esters must be hydrotreated to remove all oxygen and olefinic bonds. Additionally, jet fuels must contain aromatics in order to meet the stringent energy density and seal swelling demands of jet turbine engines. Accordingly, synthetic jet fuels including hydrotreated fatty acid esters from seed oils, or synthetic fuels produced from coal, must be blended with aromatic compounds derived from fossil fuels to fully meet jet fuel specifications.

Aromatic compounds are conventionally produced from petroleum feedstocks in refineries by reacting mixtures of light hydrocarbons ($C_1$-$C_6$) and naphthas over various catalysts at high heat and pressure. The mixture of light hydrocarbons available to a refinery is diverse, and provides a mixture of aromatic compounds suitable for use in fuel once the carcinogenic benzene is removed. Alternatively, the hydrocarbon feedstocks can be purified into single components to produce a purer aromatic product. For example, aromatization of pure isooctene selectively forms p-xylene over some catalysts. The by-products of these reactions are very light fractions containing hydrogen, methane, ethane, and propane gases which are captured at the refinery for other uses.

Low molecular weight alkanes and alkenes can also be converted into aromatic compounds such as xylene using a variety of alumina and silica based catalysts and reactor configurations. For example, the Cyclar process developed by UOP and BP for converting liquefied petroleum gas into aromatic compounds uses a gallium-doped zeolite (*Appl. Catal. A*, 1992, 89, p. 1-30). Other catalysts reported in the patent literature include bismuth, lead, or antimony oxides (U.S. Pat. Nos. 3,644,550 and 3,830,866), chromium treated alumina (U.S. Pat. Nos. 3,836,603 and 6,600,081 B2), rhenium treated alumina (U.S. Pat. No. 4,229,320) and platinum treated zeolites (WO 2005/065393 A2).

Alternatively, low molecular weight ($C_2$-$C_5$) alkanes and alkenes can be treated with acidic catalysts to produce higher molecular weight ($C_8$-$C_{20}$) alkanes and alkenes. Mixtures of these alkanes and alkenes are then blended at the refinery to provide gasoline, jet, and diesel fuel. In particular, these "alkylates" can be blended with gasoline to reduce vapor pressure and raise octane value. However, unlike gasoline and diesel, jet fuel specifications cannot tolerate high quantities of olefins. To produce useful hydrocarbons suitable for jet fuel, the olefins must be reduced to saturated hydrocarbons using an additional hydrogenation step. In general, in petroleum refineries small alkanes and alkenes have little value and are processed as described above to form higher molecular weight hydrocarbons that can be blended into the higher value hydrocarbons that constitute the majority of a barrel of crude oil.

The compositions and processes of the present invention provide improved, renewable biofuels with costs and performance properties comparable to, or superior to existing biofuels and petroleum-derived fuels (e.g., jet fuels). In addition, the process of the present invention provides an integrated and simple method for producing saturated $C_8$-$C_{24}$ aliphatic hydrocarbons and aromatics from renewable alcohols (with low levels of olefins) derived from biomass. In one embodiment, the process of the present invention provides an on-specification fuel (e.g., gasoline, diesel, or jet fuel) which is completely comprised of renewable hydrocarbons.

SUMMARY OF THE INVENTION

In one embodiment, the present invention is directed to a process for preparing renewable hydrocarbons comprising:

(a) treating biomass to form a feedstock;
(b) fermenting the feedstock with one or more species of microorganism, thereby forming one or more $C_2$-$C_6$ alcohols;
(c) dehydrating at least a portion of the one or more $C_2$-$C_6$ alcohols obtained in step (b), thereby forming a product comprising one or more $C_2$-$C_6$ olefins;
(d) isolating the one or more $C_2$-$C_6$ olefins;
(e) oligomerizing at least a portion of the one or more $C_2$-$C_6$ olefins isolated in step (d), thereby forming a product comprising one or more $C_6$-$C_{24}$ unsaturated oligomers; and
(f) optionally hydrogenating at least a portion of the product of step (e) in the presence of hydrogen, thereby forming a product comprising one or more $C_6$-$C_{24}$ saturated alkanes.

In another embodiment, the present invention is directed to a process for preparing a renewable aromatic compound, comprising:

(i) treating biomass to form a feedstock;
(ii) fermenting the feedstock with one or more species of microorganism, thereby forming one or more $C_2$-$C_6$ alcohols;
(iii) dehydrating at least a portion of the one or more $C_2$-$C_6$ alcohols obtained in step (ii), thereby forming a product comprising one or more $C_2$-$C_6$ olefins;
(iv) isolating the one or more $C_2$-$C_6$ olefins;
(v) optionally oligomerizing the one or more $C_2$-$C_6$ olefins to one or more dimers and/or one or more trimers of the $C_2$-$C_6$ olefins;
(vi) aromatizing one or more $C_2$-$C_6$ olefins from step (iv) or one or more dimers and/or one or more trimers of the $C_2$-$C_6$ olefins of step (v), thereby forming a product comprising $C_6$-$C_{14}$ aromatic hydrocarbons, and hydrogen; and
(vii) optionally oligomerizing the product of step (vi) in the presence of the one or more $C_2$-$C_6$ olefins of step (v) to form a product comprising one or more $C_8$-$C_{16}$ aromatic hydrocarbons.

In still another embodiment, the present invention is directed to a process for preparing renewable oxidized hydrocarbons comprising:

(A) treating biomass to form a feedstock;
(B) fermenting the feedstock with one or more species of microorganism, thereby forming one or more $C_2$-$C_6$ alcohols;
(C) dehydrating at least a portion of the one or more $C_2$-$C_6$ alcohols obtained in step (b), thereby forming a product comprising one or more $C_2$-$C_6$ olefins;
(D) isolating the one or more $C_2$-$C_6$ olefins; and
(E) oxidizing the one or more $C_2$-$C_6$ olefins of step (c) to form at least one oxidized hydrocarbon.

In still yet another embodiment, the present invention is directed to a biofuel or biofuel precursor prepared by the processes of the present invention described herein.

In further embodiments, the present invention is directed to a biofuel or biofuel precursor comprising at least 10% renewable $C_8$-$C_{24}$ branched aliphatic hydrocarbons.

In still other embodiments, the present invention is directed to a renewable jet fuel, a renewable gasoline, a renewable aviation gasoline, a renewable diesel fuel, and renewable oxidized hydrocarbons.

BRIEF DESCRIPTION OF THE DRAWINGS

FIG. 4 is a comparison of GC traces of petroleum-derived jet fuel and GC traces of a renewable jet fuel prepared by the process of the present invention.

FIG. 7 is a Table comparing various properties of petroleum-derived diesel fuel and a renewable diesel fuel prepared by the process of the present invention.

DETAILED DESCRIPTION OF THE INVENTION

Figure 1:
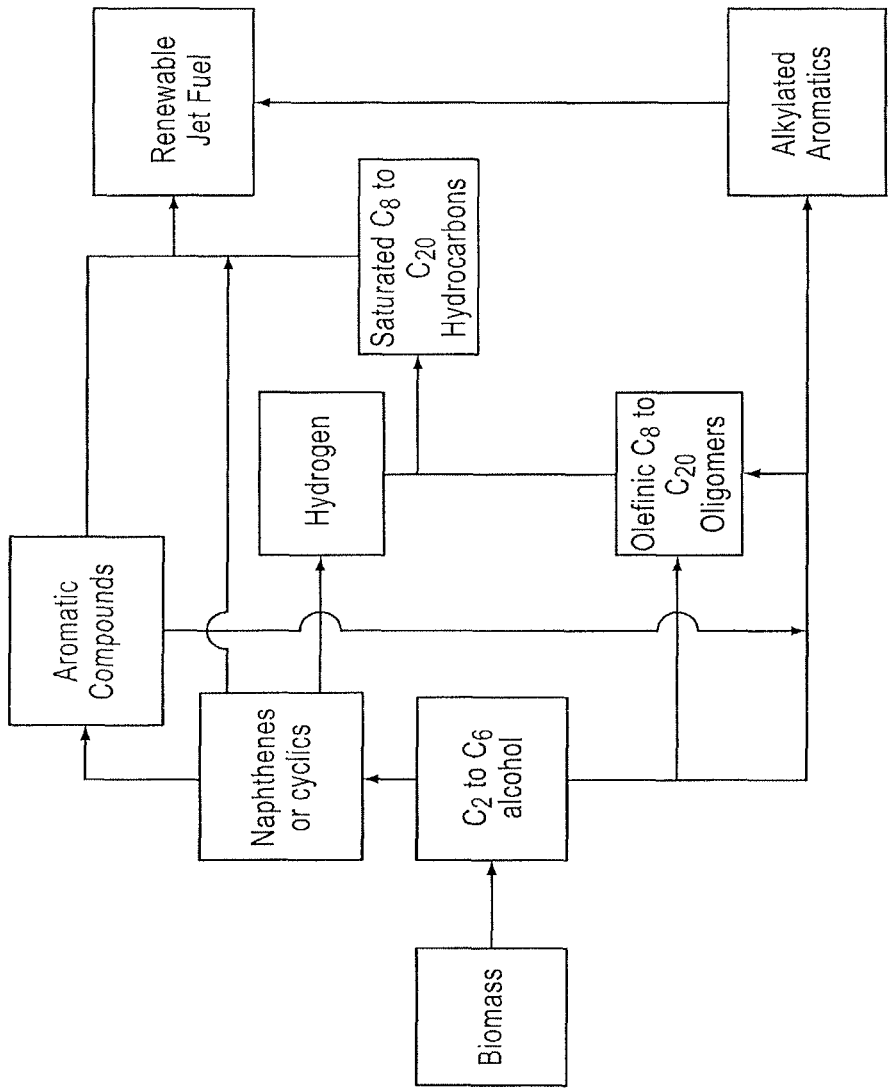
FIG. 1 shows a schematic diagram of one embodiment of an integrated process for producing a renewable jet fuel from biomass.
Figure 2:
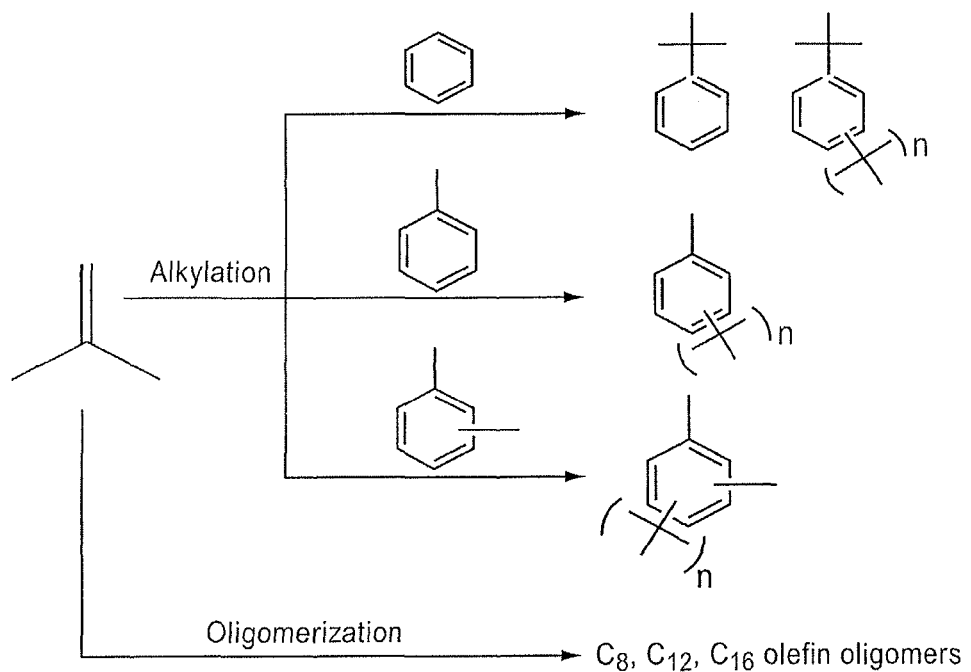
FIG. 2 is a schematic diagram of a combined oligomerization and aromatic alkylation in one pot.
Figure 3:
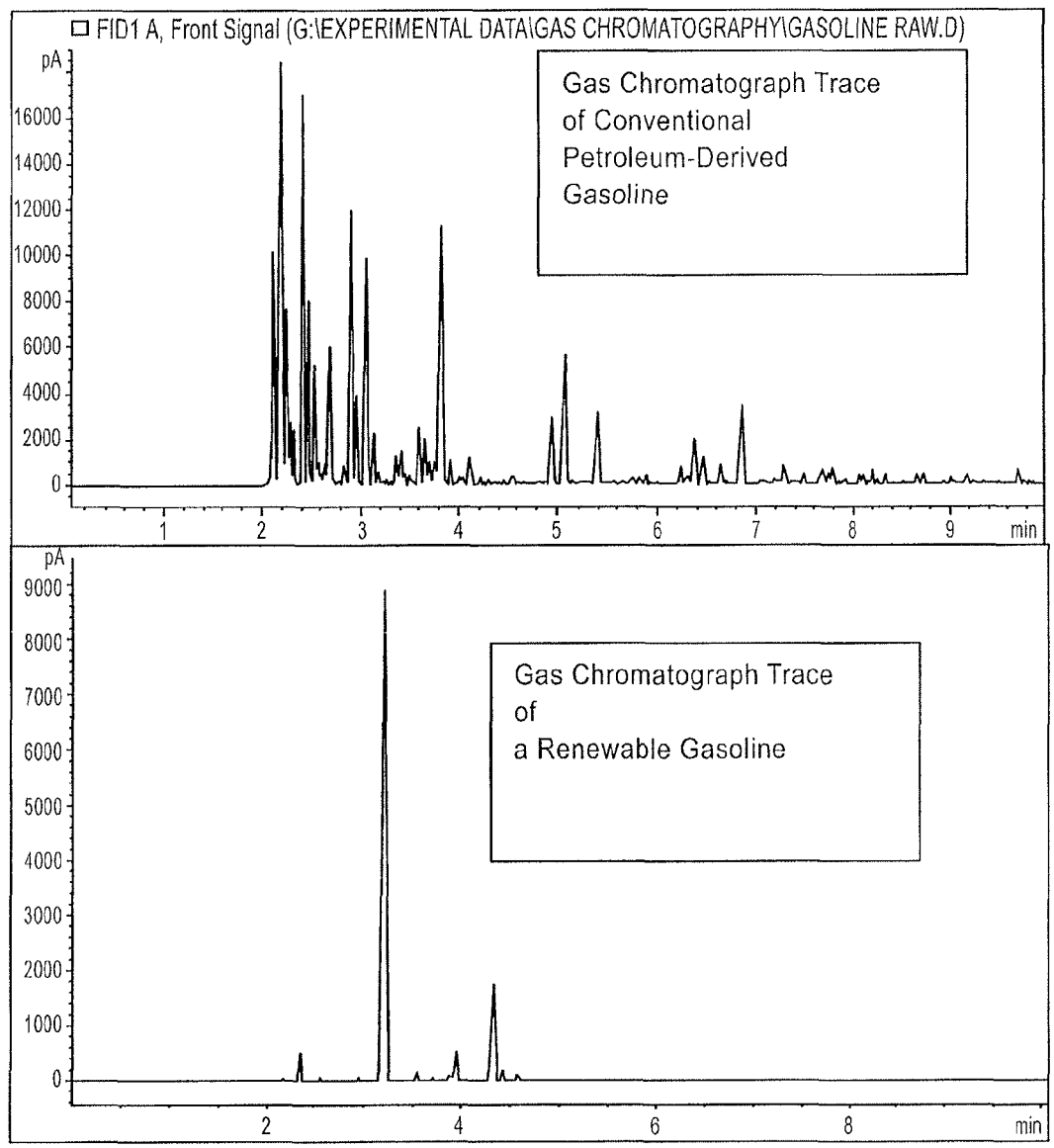
FIG. 3 is a comparison of GC traces of petroleum-derived gasoline and GC traces of a renewable gasoline prepared by the process of the present invention.
Figure 5:
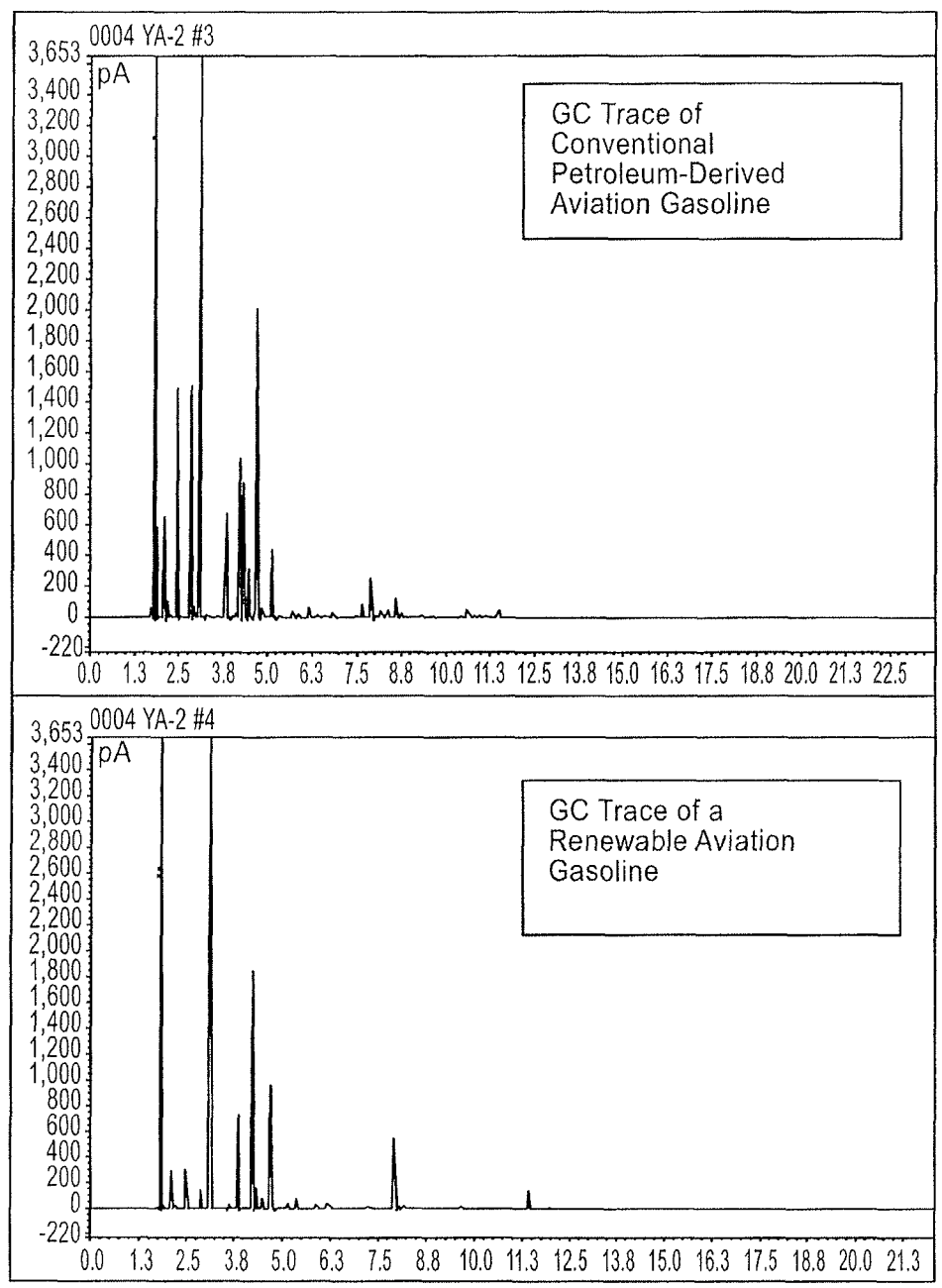
FIG. 5 is a comparison of GC traces of petroleum-derived aviation gasoline and GC traces of a renewable aviation gasoline prepared by the process of the present invention.
Figure 6:
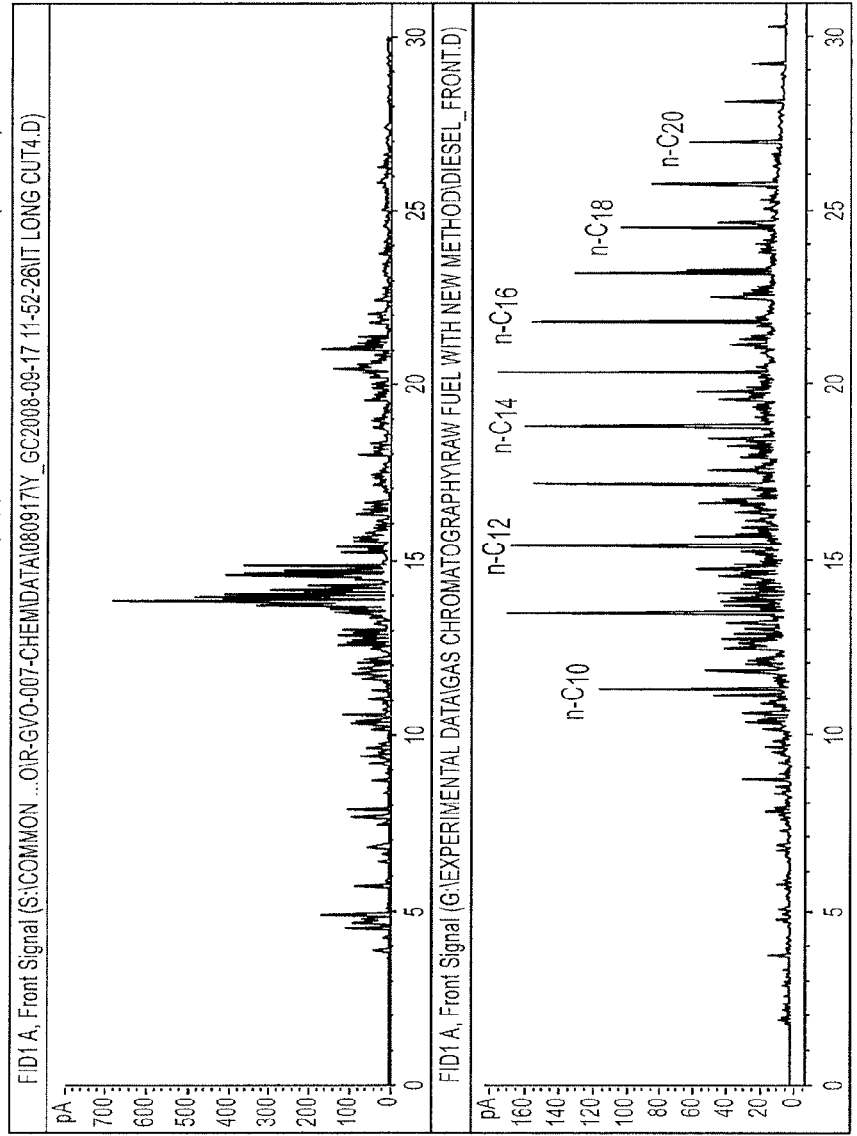
FIG. 6 is a comparison of GC traces of petroleum-derived diesel fuel and GC traces of a renewable diesel fuel prepared by the process of the present invention.

All documents disclosed herein (including patents, journal references, ASTM methods, etc.) are each incorporated by reference in their entirety for all purposes.

The term "biocatalyst" means a living system or cell of any type that speeds up chemical reactions by lowering the activation energy of the reaction and is neither consumed nor altered in the process. Biocatalysts may include, but are not limited to, microorganisms such as yeasts, fungi, bacteria, and archaea.

The biocatalyst herein disclosed can convert various carbon sources into biofuels. The term "carbon source" generally refers to a substance suitable to be used as a source of carbon for prokaryotic or eukaryotic cell growth. Carbon sources include, but are not limited to biomass hydrolysates, starch, sucrose, cellulose, hemicellulose, xylose, and lignin, as well as monomeric components of these substrates. Carbon sources can comprise various organic compounds in various forms including, but not limited to, polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis. In some embodiments, carbon sources may be selected from biomass hydrolysates and glucose.

The term "feedstock" is defined as a raw material or mixture of raw materials supplied to a biocatalyst (e.g., microorganism) or fermentation process from which other products can be made. For example, a carbon source, such as biomass or the carbon compounds derived from biomass (e.g., a biomass hydrolysate as described herein) are a feedstock for a biocatalyst (e.g., a microorganism) that produces a biofuel (e.g., ethanol, isobutanol) or biofuel precursor (e.g., isobutanol) in a fermentation process. However, a feedstock may contain nutrients other than a carbon source. The term feedstock is used interchangeably with the term "renewable feedstock", as the feedstocks used are generated from biomass or traditional carbohydrates, which are renewable substances.

The term "traditional carbohydrates" refers to sugars and starches generated from specialized plants, such as sugar cane, corn, and wheat. Frequently, these specialized plants concentrate sugars and starches in portions of the plant, such as grains, that are harvested and processed to extract the sugars and starches. Traditional carbohydrates are used as food, and also to a lesser extent, as renewable feedstocks for fermentation processes to generate biofuel precursors.

The term "biomass" as used herein refers primarily to the stems, leaves, and starch-containing portions of green plants, and is mainly comprised of starch, lignin, cellulose, hemicellulose, and/or pectin. Biomass can be decomposed by either chemical or enzymatic treatment to the monomeric sugars and phenols of which it is composed (Wyman, C. E. 2003 Biotechnological Progress 19:254-62). This resulting material, called biomass hydrolysate, is neutralized and treated to remove trace amounts of organic material that may adversely affect the biocatalyst, and is then used as a feedstock for fermentations using a biocatalyst. Alternatively, the biomass may be thermochemically treated to produce alcohols and alkanes that may be further treated to produce biofuels.

The term "starch" as used herein refers to a polymer of glucose readily hydrolyzed by digestive enzymes. Starch is usually concentrated in specialized portions of plants, such as potatoes, corn kernels, rice grains, wheat grains, and sugar cane stems.

The term "lignin" as used herein refers to a polymer material, mainly composed of linked phenolic monomeric compounds, such as p-coumaryl alcohol, coniferyl alcohol, and sinapyl alcohol, which forms the basis of structural rigidity in plants and is frequently referred to as the woody portion of plants. Lignin is also considered to be the non-carbohydrate portion of the cell wall of plants.

The term "cellulose" as used herein refers is a long-chain polymer polysaccharide carbohydrate comprised of β-glucose monomer units, of formula $(C_6H_{10}O_5)_n$, usually found in plant cell walls in combination with lignin and any hemicellulose.

The term "hemicellulose" refers to a class of plant cell-wall polysaccharides that can be any of several heteropolymers. These include xylane, xyloglucan, arabinoxylan, arabinogalactan, glucuronoxylan, glucomannan and galactomannan. Monomeric components of hemicellulose include, but are not limited to: D-galactose, L-galactose, D-mannose, L-rhamnose, L-fucose, D-xylose, L-arabinose, and D-glucuronic acid. This class of polysaccharides is found in almost all cell walls along with cellulose. Hemicellulose is lower in weight than cellulose and cannot be extracted by hot water or chelating agents, but can be extracted by aqueous alkali. Polymeric chains of hemicellulose bind pectin and cellulose in a network of cross-linked fibers forming the cell walls of most plant cells.

The term "pectin" as used herein refers to a class of plant cell-wall heterogeneous polysaccharides that can be extracted by treatment with acids and chelating agents. Typically, 70-80% of pectin is found as a linear chain of α-(1-4)-linked D-galacturonic acid monomers. The smaller RG-I fraction of pectin is comprised of alternating (1-4)-linked galacturonic acid and (1-2)-linked L-rhamnose, with substantial arabinogalactan branching emanating from the rhamnose residue. Other monosaccharides, such as D-fucose, D-xylose, apiose, aceric acid, Kdo, Dha, 2-O-methyl-D-fucose, and 2-O-methyl-D-xylose, are found either in the RG-II pectin fraction (<2%), or as minor constituents in the RG-1 fraction. Proportions of each of the monosaccharides in relation to D-galacturonic acid vary depending on the individual plant and its micro-environment, the species, and time during the growth cycle. For the same reasons, the homogalacturonan and RG-I fractions can differ widely in their content of methyl esters on GalA residues, and the content of acetyl residue esters on the C-2 and C-3 positions of GalA and neutral sugars.

The term "inhibitor" refers to organic and inorganic compounds that when present above a certain concentration, defined as the "inhibitory concentration," impair a biocatalyst during a fermentation process. The inhibitory concentration is dependent upon the inhibitor, the biocatalyst, and the process conditions combined. Examples of inhibitors include, but are not limited to, fermentation products, pretreatment products, fermentation intermediates, carbon source, and feedstock components.

The term "volumetric productivity" is defined as the amount of product per volume of media in a fermentor per unit of time. In some embodiments, the productivity may be expressed as the amount of product per unit of time, e.g., g/hr, when the volume of the fermentor is fixed at a specific volume.

The term "specific productivity" is defined as the rate of formation of the product. To describe productivity as an inherent parameter of the microorganism or biocatalyst and not of the fermentation process, productivity is herein further defined as the specific productivity in g product per g of cell dry weight (CDW) per hour (g product g $CDW^{-1}$ $h^{-1}$).

The term "yield" is defined as the amount of product obtained per unit weight of raw material and may be expressed as g product/g substrate. Yield may be expressed as a percentage of the theoretical yield. "Theoretical yield" is defined as the maximum amount of product that can be generated per a given amount of substrate as dictated by the stoichiometry of the metabolic pathway used to make the product. For example, if the theoretical yield for one typical conversion of glucose to isobutanol is 0.41 g/g, the yield of butanol from glucose of 0.39 g/g would be expressed as 95% of theoretical or 95% theoretical yield.

The term "tolerance" is defined as the ability of the biocatalyst to maintain its specific productivity at a given concentration of an inhibitor. The term "tolerant" describes a biocatalyst that maintains its specific productivity at a given concentration of an inhibitor. For example, if in the presence of 2% of an inhibitor a biocatalyst maintains the specific productivity that it had at 0 to 2% of an inhibitor, the biocatalyst is tolerant to 2% of the inhibitor, or has a tolerance to 2% of the inhibitor.

The term "rate of inhibition" is defined as the rate of decrease of the specific productivity of a biocatalyst relative to the increased concentration of an inhibitor, at inhibitor levels above the inhibitory concentration.

The term "resistance" is defined as a property of a biocatalyst that leads to a low rate of inhibition in the presence of increasing concentrations of an inhibitor in the fermentation broth. The term "more resistant" describes a biocatalyst that has a lower rate of inhibition towards an inhibitor than another biocatalyst with a higher rate of inhibition towards the same inhibitor. For example, suppose two biocatalysts, A and B, are both tolerant to 2% (w/w) of an inhibitor and both a specific productivity of 1 g product g $CDW^{-1}$ $h^{-1}$. If at 3% (w/w) inhibitor concentration biocatalyst A has a specific productivity of 0.5 g product g $CDW^{-1}$ $h^{-1}$ and biocatalyst B has a productivity of 0.75 g product g $CDW^{-1}$ $h^{-1}$, then biocatalyst B is more resistant than biocatalyst A.

The term "titre" (or "titer", which can be used interchangeably) is defined as the strength of a solution or the concentration of a substance in solution. For example, the titre of a biofuel precursor in a fermentation broth is described as g of biofuel precursor in solution per liter of fermentation broth.

The term "primarily" in reference to a component of a composition of the present invention (e.g., a composition comprised "primarily of butene dimers") refers to a composition which comprises at least 50% of the referenced component.

The term "biofuel precursor" refers to an organic molecule in which all of the carbon contained within the molecule is derived from biomass, and is thermochemically or biochemically converted from a feedstock into the precursor. A biofuel precursor may be a biofuel in its own right or may be configured for conversion, either chemically or biochemically, into a biofuel with different properties. Biofuel precursors include, but are not limited to, 1-propanol, 2-propanol, 1-butanol, 2-butanol, isobutanol, 1-pentanol, isopentanol (3-methyl-1-butanol), 3-pentanol, 2-methyl-1-butanol, or neopentanol.

The term "byproduct" means an undesired product related to the production of biofuel or biofuel precursor. Byproducts are generally disposed of as waste, thereby increasing the cost of the process.

The term "co-product" means a secondary or incidental product related to the production of biofuel or biofuel precursor. Co-products have potential commercial value that increases the overall value of biofuel precursor production, and may be the deciding factor as to the viability of a particular biofuel or biofuel precursor production process.

The terms "alkene" and "olefin" are used interchangeably herein to refer to non-aromatic hydrocarbons having at least one carbon-carbon double bond.

The term "distillers dried grains", abbreviated herein as DDG, refers to the solids remaining after a fermentation, usually consisting of unconsumed feedstock solids, remaining nutrients, protein, fiber, and oil, as well as biocatalyst cell debris. The term may also include soluble residual material from the fermentation and is then referred to as "distillers dried grains and solubles" (DDGS).

The term "fusel alcohols" refers to alcohols such as propanols, butanols, and pentanols that are produced by microorganisms such as yeast during the fermentation process to make wine and beer.

"Carbon of atmospheric origin" as used herein refers to carbon atoms from carbon dioxide molecules that have recently (e.g., in the last few decades) been free in the earth's atmosphere. Such carbon atoms are identifiable by the ratio of particular radioisotopes as described herein. "Green carbon", "atmospheric carbon", "environmentally friendly carbon", "life-cycle carbon", "non-fossil fuel based carbon", "non-petroleum based carbon", "carbon of atmospheric origin", and "biobased carbon" are used synonymously herein.

"Carbon of fossil origin" as used herein refers to carbon of petrochemical origin. Carbon of fossil origin is identifiable by means described herein. "Fossil fuel carbon", "fossil carbon", "polluting carbon", "petrochemical carbon", "petrocarbon" and "carbon of fossil origin" are used synonymously herein.

The term "isomerate" as used herein refers to the product of an isomerization reaction, for example a relatively high octane hydrocarbon mixture prepared by isomerizing simple alkanes.

"Renewably-based" or "renewable" denote that the carbon content of the biofuel precursor and subsequent products is from a "new carbon" source as measured by ASTM test method D 6866-05, "Determining the Biobased Content of Natural Range Materials Using Radiocarbon and Isotope Ratio Mass Spectrometry Analysis", incorporated herein by reference in its entirety. This test method measures the $^{14}C/^{12}C$ isotope ratio in a sample and compares it to the $^{14}C/^{12}C$ isotope ratio in a standard 100% biobased material to give percent biobased content of the sample. "Biobased materials" are organic materials in which the carbon comes from recently (on a human time scale) fixated $CO_2$ present in the atmosphere using sunlight energy (photosynthesis). On land, this $CO_2$ is captured or fixated by plant life (e.g., agricultural crops or forestry materials). In the oceans, the $CO_2$ is captured or fixated by photosynthesizing bacteria or phytoplankton. For example, a biobased material has a $^{14}C/^{12}C$ isotope ratio greater than 0. Contrarily, a fossil-based material, has a $^{14}C/^{12}C$ isotope ratio of about 0. The term "renewable" with regard to compounds such as alcohols or hydrocarbons (linear or cyclic alkanes/alkenes/alkynes, aromatic, etc.) refers to compounds prepared from biomass using thermochemical methods (e.g., Fischer-Tropsch catalysts), biocatalysts (e.g., fermentation), or other processes, for example as described herein.

A small amount of the carbon atoms of the carbon dioxide in the atmosphere is the radioactive isotope $^{14}C$. This $^{14}C$ carbon dioxide is created when atmospheric nitrogen is struck by a cosmic ray generated neutron, causing the nitrogen to lose a proton and form carbon of atomic mass 14 ($^{14}C$), which is then immediately oxidized to carbon dioxide. A small but measurable fraction of atmospheric carbon is present in the form of $^{14}CO_2$. Atmospheric carbon dioxide is processed by green plants to make organic molecules during the process known as photosynthesis. Virtually all forms of life on Earth depend on this green plant production of organic molecule to produce the chemical energy that facilitates growth and reproduction. Therefore, the $^{14}C$ that forms in the atmosphere eventually becomes part of all life forms and their biological products, enriching biomass and organisms which feed on biomass with $^{14}C$. In contrast, carbon from fossil fuels does not have the signature $^{14}C:^{12}C$ ratio of renewable organic molecules derived from atmospheric carbon dioxide. Furthermore, renewable organic molecules that biodegrade to $CO_2$ do not contribute to global warming as there is no net increase of carbon emitted to the atmosphere.

Assessment of the renewably based carbon content of a material can be performed through standard test methods, e.g. using radiocarbon and isotope ratio mass spectrometry analysis. ASTM International (formally known as the American Society for Testing and Materials) has established a standard method for assessing the biobased content of materials. The ASTM method is designated ASTM-D6866.

The application of ASTM-D6866 to derive "biobased content" is built on the same concepts as radiocarbon dating, but without use of the age equations. The analysis is performed by deriving a ratio of the amount of radiocarbon ($^{14}C$) in an unknown sample compared to that of a modem reference standard. This ratio is reported as a percentage with the units "pMC" (percent modern carbon). If the material being analyzed is a mixture of present day radiocarbon and fossil carbon (containing very low levels of radiocarbon), then the pMC value obtained correlates directly to the amount of biomass material present in the sample.

The transportation fuels of the present invention have pMC values of at least about 1, 5, 10, 15, 20, 25, 30, 35, 40, 45, 50, 55, 60, 65, 70, 75, 80, 85, 90, 95, 100, inclusive of all values and subranges therebetween.

The term "dehydration" refers to a chemical reaction that converts an alcohol into its corresponding alkene. For example, the dehydration of isobutanol produces isobutylene.

The term "aromatic compounds" or "aromatics" refers to hydrocarbons that contain at least one aromatic, six-membered ring. Examples of aromatics relative to this invention are benzene, toluene, ethyl benzene, propyl benzene, o-xylene, m-xylene, p-xylene, o-methyl ethyl xylene, and other mono- and di-alkylated benzenes.

The term "oligomerization" or "oligomerizing" refer to processes in which activated molecules such as alkenes are combined with the assistance of a catalyst to form larger molecules called oligomers. Oligomerization refers to the combination of identical alkenes (e.g. isobutylene) as well as the combination of different alkenes (e.g. isobutylene and propene), or the combination of an unsaturated oligomer with an alkene. For example, isobutylene is oligomerized by an acidic catalyst to form eight-carbon oligomers such as isooctene (e.g., trimethylpent-1-enes and trimethylpent-2-enes) and twelve-carbon oligomers such as 2,2,4,6,6-pentamethylheptene, 2,4,4,6,6-pentamethylhept-1-ene. In this example, isobutylene is a monomer, isooctene is a dimer of isobutylene, and 2,2,4,6,6-pentamethylheptene is a trimer of isobutylene.

The term "rearrangement" refers to a chemical reaction in which alkyl groups on a hydrocarbon migrate to different positions on a carbon backbone molecule during an oligomerization reaction. For example, the expected product of the oligomerization of isobutylene without rearrangement is the trimer 2,4,4,6,6-pentamethylhept-1-ene. With rearrangement, the methyl groups can migrate to other positions on the heptene backbone to produce hydrocarbons such as 2,4,4,5,6-pentamethylheptene and 2,4,5,5,6-pentamethylheptene.

Typically, acidic catalysts catalyze both oligomerization and rearrangement, and thus both reactions typically occur nearly simultaneously. Accordingly, as used herein the term "oligomerization" refers to the combination of alkenes in the presence of a catalyst to form larger molecules, as described herein, as well as the rearrangement of the resulting oligomers to form various isomers as described herein, unless otherwise indicated.

As described herein, olefins or mixtures of olefins can be reacted to form aromatic hydrocarbons (including alkylated aromatic hydrocarbons) in the presence of an aromatization catalyst. The resulting aromatic hydrocarbons can be reacted in the presence of olefins and an oligomerization catalyst to form more highly alkylated aromatic hydrocarbons. For example, benzene can be reacted with isobutylene in the presence of an oligomerization catalyst as described herein to form t-butylbenzene or di-t-butylbenzenes. Similarly, toluene can be reacted in the presence of an oligomerization catalyst and isobutylene to form t-butylmethylbenzenes, etc. The term "oligomerization" thus can also include the "alkylation" of aromatic hydrocarbons in the presence of an oligomerization catalyst and olefins. Catalysts specifically intended or optimized for the alkylation of aromatics are also termed alkylation or alkylating catalysts, and catalysts specifically intended or optimized for oligomerization are termed oligomerization catalysts. Oligomerization and alkylation can, in some embodiments be carried out simultaneously in the presence of a single catalyst capable of carrying out both reactions, or in other embodiments can be carried out as separate reactions using separate oligomerization and alkylation catalysts.

The term "aromatization" refers to processes in which hydrocarbon starting materials, typically alkenes or alkanes, are converted into aromatic compounds (e.g., benzene, toluene, and/or xylenes) by dehydrocyclodimerization.

The term "reaction zone" refers to the part of a reactor or series of reactors where the substrates and chemical intermediates contact a catalyst to ultimately form product. The reaction zone for a simple reaction may be a single vessel containing a single catalyst. For a reaction requiring two different catalysts, the reaction zone can be a single vessel containing a mixture of the two catalysts, a single vessel such as a tube reactor which contains the two catalysts in two separate layers, or two vessels with a separate catalyst in each which may be the same or different.

The term "conventional fuels" or "non-renewable" fuels refers to any liquid fuel in which all of the carbon is originally derived from a fossil sources, such as petroleum, natural gas, and coal.

The term "fuel additive" refers to any component of liquid fuel, representing less than 30% of the total fuel volume, which is added to the fuel to impart specific performance properties to the fuel. Fuel additives include, but are not limited to octane enhancers for gasoline; cetane enhancers for diesel fuel; anti-static additives to enhance static charge dissipation; anti-icing additives to reduce the formation of ice crystals, and prevent the plugging of fuel filters at low temperatures; and anti-microbial additives to prevent fungal and bacterial growth at water/fuel interfaces. While all currently-used fuel additives are derived from non-renewable or fossil sources, such as petroleum, natural gas, and coal, new fuel additive products may also be derived from renewable, biomass-derived sources.

The term "ASTM" refers to the American Society of Testing and Materials, which defines testing procedures and specifications for all petroleum products manufactured and sold commercially. For example, the specification for gasoline is D4814; for aviation fuels, D1655; and for diesel fuels, D975.

The terms "Research Octane Number (RON)" and "Motor Octane Number (MON)" are measures of gasoline engine performance. RON is defined by ASTM methods D2699 and D2885, and MON is defined by ASTM methods D2700 and D2885. Anti-knock index is defined by the arithmetic average of the two octane numbers: (RON+MON)/2.

The term "Cetane Number" is defined as measure of diesel engine performance by ASTM method D613, and is roughly analogous in its usage to octane numbers used in gasoline engines. A close approximation to the Cetane Number is the Cetane Index, which can be computed according to ASTM D976.

The term "Derived Cetane Number" or DCN is another measure of diesel fuel ignition performance as defined in ASTM methods D7170-08 or D6890-08.

The term "gasoline" refers to a mixture typically comprising primarily hydrocarbon compounds that can be used to operate spark ignition engines (e.g., automotive engines), and is more volatile than jet fuel or diesel fuel. Gasoline can also include additives such as alcohols and other oxygenated organic compounds. In practical terms, the mixture of hydrocarbons and optional additives called gasoline must at least meet ASTM D4814 specifications.

The term "diesel fuel" refers to a mixture typically comprising primarily hydrocarbon compounds that can be used to operate a diesel engine. In practical terms, the mixture of hydrocarbons called diesel fuel must meet key ASTM specifications for diesel fuel listed in ASTM specification D975. Typical petroleum-based diesel fuels consist of primarily linear alkanes with $C_{14}$-$C_{15}$ alkanes as the major component, and lesser amounts of smaller and larger alkanes.

The term "jet fuel" refers to a mixture typically comprising primarily hydrocarbon compounds that can be used to operate a jet engine. Jet fuel can also include optional non-hydrocarbon additives. In practical terms, the mixture of hydrocarbons and optional additives called jet fuel must at least meet key ASTM specifications for jet fuel listed in ASTM specification D1655. Typical petroleum-based jet fuels consist primarily of straight chain alkanes, with $C_{12}$ alkanes as the major component, and lesser amounts of aromatics and smaller and larger alkanes.

A "fuel precursor" refers to a mixture comprising hydrocarbons (aliphatic and/or aromatic hydrocarbons) that does not meet one or more of the respective fuel specifications (e.g., the ASTM requirements described herein applicable to spark ignition fuels, diesel fuels, or jet fuels), but which can be adjusted to meet these specifications by blending an appropriate amount (e.g., typically up to about 10%, up to about 20%, up to about 30%, up to about 40%, or up to about 50%) of the appropriate hydrocarbons.

The term "Weight Hourly Space Velocity" or "WHSV" refers to the weight of a reactant that is passed over a given weight of catalyst in a flow reactor configuration over an hour.

The term "saturated" refers to the oxidation state of a hydrocarbon molecule in which all bonds are single bonds between carbon and hydrogen. Saturated acyclic hydrocarbons have a general molecular formula of $C_nH_{2n+2}$.

The terms "terephthalates", "isophthalates", and "phthalates" refers to both esters, free acids, and salts of terephthalic acid, isophthalic acid, and phthalic acid, unless expressly indicated otherwise.

As indicated above, the compositions of transportation fuels (e.g., jet and diesel fuels) are not defined at a molecular level. Instead, transportation fuels are defined as mixtures of typically aliphatic and (optionally) aromatic hydrocarbons that meet a collection of physical properties and specifications (e.g., as described in ASTM D1655, D 4817, D975, D910). All engines and turbines that use these fuels are designed to use mixtures (typically primarily hydrocarbons) with these specific properties. If a biofuel is to be widely used as a transportation fuel replacement, it must also meet this collection of physical properties and specifications.

For jet fuel or aviation turbine fuel, the key ASTM specifications related to intrinsic fuel properties are measured by the following tests: flash point, distillation temperature range, density, freezing point, viscosity, net heat of combustion, smoke point, naphthalene content, aromatic content, thermal oxidation stability, gum content, and acidity. Jet fuel volatility affects the performance of the fuel, especially its ability to be ignited in jet engine, and safety and handling of the material both on and off the aircraft. Flash point measures the minimum temperature a liquid must be at to form a flammable vapor mixture with air above its surface. It is measured by heating a quantity of the fuel until its surface can be ignited by a flame or an electric ignition source. The specification for jet fuel flash point is a minimum 38° C. and is measured using ASTM method D56 or D3828. The physical distillation temperature range of a jet fuel is a measure of the type and behavior of the various hydrocarbon molecules in the mixture. Jet fuel physical distillation temperature range is measured by ASTM method D86. The specification for jet fuel is 10% of the mass of the fuel is recovered at maximum of 205° C. and the final boiling point of the last bit of material is at a maximum of 300° C. The density of a jet fuel must be constant since transfer equipment and pumps function volumetrically and fuel tanks on aircrafts are designed to hold fixed volumes of jet fuel. Jet fuel density or specific gravity is measured by ASTM method D1298 or D 4052 and must be in the range of 775 to 840 kg/m$^3$ at 15° C. API gravity is another way of measuring jet fuel density and is measured by comparing the gravity of the jet fuel on an arbitrary scale from 0 to 100 with water having an API gravity of 10 on the scale. The API gravity range for jet fuel is between 37 and 51.

Low temperature operability of jet fuels is essential because jet aircraft operate at high altitudes where temperatures are typically between −60° C. and −40° C. If the jet fuel freezes solid or even clouds up during operation at these temperatures, the aircraft will cease to fly. Freezing point measures the lowest temperature at which the material remains a liquid. The specification for the freezing point of jet fuel is a maximum of −40° C. for Jet A (jet fuel used within the United States) or a maximum of −47° C. for Jet A-1 (jet fuel used on international flights) measured by ASTM method D7154. Viscosity measures the ability of the fuel to flow. The jet fuel viscosity specification is a maximum of 8.0 mm$^2$/s measured by ASTM method D445.

The combustion properties of jet fuel must be in specification to ensure that the fuel functions properly. Net heat of combustion measures the energy content of the fuel and is critical because it indirectly determines how far an aircraft can fly. The higher the energy density of a fuel the better, but the specification for jet fuel net heat of combustion is a minimum of 42.8 MJ/kg measured by ASTM method D4809. Smoke point measures the combustion quality of the fuel and is inversely correlated with radiant heat transfer in jet engine combustors. The smoke point is also an indicator of soot forming potential of a fuel. In general, the higher the smoke point, measured by burning the fuel in a wick-fed lamp and measuring the flame size at which smoking occurs, the higher quality the fuel and the longer the jet engine combustor part lifetimes. The jet fuel smoke point specification is a minimum of 25 mm measured by ASTM method D1322. Combustion quality is also measured by the amount of aromatic organic compounds in the jet fuel. In general, high amounts of naphthalenes burn hotter than other hydrocarbons, limiting the lifetime of jet engine parts. The specification for naphthalene content in jet fuel is a maximum of 3% measured by ASTM method D1840. Similarly, high aromatics in jet fuel affect combustion quality, especially heat transfer and soot formation. The specification for aromatic content in jet fuel is a maximum of 25% measured by ASTM method D1319.

Jet fuel must be stable when stored and when exposed to the temperature extremes during operation. In a jet engine, jet fuel is used as a heat sink and lubricant meaning that it is exposed to most of the moving parts of the engine at fairly high temperatures. Jet fuel high temperature stability is measured by ASTM method D3241. In this method, jet fuel is heated and recirculated through a filter to capture particles that form by the thermal oxidation of the fuel. Additionally, the recirculated fuel is passed over a polished aluminum surface to identify oxidized material that may discolor it, causing the fuel to fail the test. The specifications for this test are after 2.5 hours of recirculation at a temperature of 260° C., the maximum pressure drop across the in-line filter unit is 25 mm Hg and the tube is discolored less than 3 units on the Jet Fuel Thermal Oxidation Test (JFTOT) scale. Jet fuel low temperature stability is determined by measuring the gum content of fuel using ASTM method D381. In this method, heated air or steam is used to evaporate a portion of jet fuel to dryness and the residue is weighed to measure the amount of non-volatile compounds in the fuel. The specifications for gum content are a maximum of 7 mg/100 mL of jet fuel, although typical values for jet fuels used in the field are ~2 mg/100 mL of jet fuel. To prevent corrosion of engine components as the jet fuel lubricates and cools the engine, the acidity of the fuel must be kept low. Acidity of jet fuel is measured by ASTM method D3242 and has a specification of a maximum of 0.10 mg potassium hydroxide/g of jet fuel to neutralize the acid in the fuel. Acidity is also measured using a copper corrosion test described in ASTM method D130. This test measures the potential of a given fuel to corrode a clean copper strip. The experiment is conducted at elevated temperatures, usually for 2 hours, and corrosion is graded visually on a 1-5 scale, with 1 being essentially no change in the appearance of the copper strip. The copper corrosion specification for jet fuel is 1.

Conventional jet fuels are complex mixtures of aliphatic (80-90%) and aromatic (10-20%) hydrocarbons that are distilled from crude oil in a refinery. Crude oil is a heterogeneous mixture of thousands of different hydrocarbons that widely varies depending upon the source of the crude oil. Conventional jet fuel is produced by first distilling crude oil and taking "cuts" from the distillation column that correspond to mixtures that come close to meeting jet fuel specifications. The "cuts" are then finished off by blending in additional refined material such as other crude oil distillates or chemically altered material to meet specifications. Although the exact composition of a jet fuel can vary, in general, jet fuels are mixtures of linear and branched aliphatic hydrocarbons with a molecular weight distribution centered around $C_{12}$ hydrocarbons.

For diesel fuels the key ASTM specifications are measured by the following tests: flash point, distillation temperature range, viscosity, cetane number, aromatic composition, and copper corrosion test. There are two major grades of diesel fuel, #1 and #2, with the latter being the most commonly used in general commerce, and in particular, the trucking industry. For many of the key specifications, the requirements for #1 diesel fuels are similar to, or somewhat less demanding than, the analogous ASTM specifications for jet fuels. The requirements for #2 diesel fuels reflect the higher average molecular weights and boiling ranges of these fuels. In cases where jet fuel fails certain specifications (such as copper corrosion, smoke point, etc.), this fuel can be downgraded and sold as #1 grade diesel fuel (provided it meets cetane number specifications). Red dyes are added to some diesel fuels and can be used to distinguish them from jet and other grades of diesel fuel.

Diesel fuel is generally as or less volatile than other fuels such as gasoline and jet fuel. Like these fuels, the volatility of diesel fuel is measured by flash point and distillation range. Diesel fuel flash point is measured using ASTM method D93. #1 grade diesel fuel is required to have a minimum flash point of 38° C., whereas the flashpoint for #2 grade diesel fuel must be at least 52° C. Diesel fuel distillation range is measured using ASTM method D86. The distillation range requirement for #2 grade diesel fuel is that 90% of the fuel be recovered in the distillation range 282-338° C. For #1 grade diesel fuel, the distillation range requirement is a maximum temperature of 288° C. for this 90% fraction to be recovered.

The low temperature operability of diesel fuel depends upon where the fuel is used. Generally, in colder climates the fuel should be formulated to not freeze solid or even begin to "cloud" when stored. Because of the enormous diversity of geographies, environments, and weather conditions under which diesel engines must operate, there are no overall, specific cold property specifications for diesel fuel. This is in distinct contrast to jet fuel, which is almost always used under the very cold conditions of high altitudes. Rather than setting hundreds of diesel specifications for cold properties, sellers and distributors negotiate diesel compositions specific to their own geographic, environmental, and seasonal requirements. In virtually all cases, desired cold-flow properties can be obtained by mixing varying proportions of #1 grade diesel fuel (better cold flow—close in properties to jet fuel) and #2 grade diesel fuel (much heavier, thicker, and more viscous). Additionally, several ASTM cold flow specifications are recommended to characterize these fuel blends, including: ASTM method D2500 for cloud point which indicates the beginning of fuel crystallization, ASTM method D4539 for low temperature flow, and ASTM method D6371 for cold filter plug point which is predictive of when fuel filters will fail under cold conditions. Under cold conditions where a significant portion of #1 grade diesel fuel must be mixed with #2 grade diesel fuel to ensure engine operability, the higher distillation requirements of #2 diesel fuel are waived. The viscosity of diesel fuel is determined using ASTM method D445. In the case of #2 grade diesel fuel, the required viscosity is 1.9-4.1 mm$^2$/s at 40° C., and the required viscosity of #1 grade diesel fuel is 1.3-2.4 mm$^2$/s at 40° C.

The engine performance of diesel fuels is determined by an engine operability test which measures the cetane number, and by the amount of aromatic compounds found within the fuel. Cetane number is determined using ASTM method D613 (or alternatively, derived cetane number measured by ASTM D1707-08 or D6890-08), and a minimum cetane number of 40 is required for both #1 and #2 grade diesel fuels. Aromatic compounds in diesel fuel must be limited because large amounts of them can increase particulate air emissions, soot and deposit formation in the engines, and incomplete fuel combustion. The maximum aromatic content of diesel fuels is measured using ASTM method D1319 and is specified to be 35%. An alternative to this test is the computed "cetane index", which is computed by other distillation data according to ASTM method D976-80.

The stability of diesel fuel is partially determined by its reaction with metals over a period of time using a copper corrosion test described in ASTM method D130. This test measures the potential of a given fuel to corrode a clean copper strip. The experiment is conducted at elevated temperatures, usually for 2 hours, and corrosion is graded visually on a 1-5 scale, with 1 being essentially no change in the appearance of the copper strip. The copper corrosion specification for diesel fuel is 3.

Like diesel and jet fuels, gasoline is defined not by its composition, but by its ability to function in a spark ignition engine in very specific ways. For gasoline the ASTM key specification are defined by ASTM D4814. Also included in this document are the specifications for a series of ASTM methods used to determine whether or not gasoline and its blends are suitable fuels. The specifications can be roughly divided into two categories. The first category describes properties that are inherent to composition of the gasoline, such as vapor pressure, energy density, octane number, water solubility, thermal oxidation stability, gum content, and drivability. In general, these properties can only be adjusted by modifying the amounts and types of organic molecules that make up the gasoline. For example, if the octane number of a gasoline mixture is low, it can be raised by adding high octane components to the mixture provided that the other important properties of the mixture do not fall out of specification. The key ASTM methods relevant to the gasoline compositions of the present invention fall within the first category.

The second category of gasoline specifications describes properties that are caused by contamination of the mixture either during or after processing, especially during storage of the fuel under inadequate conditions. Properties in this second category include water content and acidity. Gasoline mixtures that measure out of specification for these properties can be treated to bring the mixture into specification. For example, excess water can be removed from gasoline by phase separation and acid can be neutralized.

The distillation range of gasoline is a property that captures many different key aspects of how the gasoline composition behaves in a combustion engine to produce usable energy. For example, volatile compounds are necessary for proper ignition of the fuel in the combustion chamber of the engine. Additionally, less volatile but energy dense compounds are required to increase overall fuel performance, especially mileage. The distillation curve of a gasoline mixture is measured using ASTM method D86, and the specification is calibrated by how the typical hydrocarbon mixtures that comprise gasoline behave in an engine. When a substantial amount of the hydrocarbon component in a gasoline mixture is replaced with a different type of organic compound, i.e. an alcohol such as n-butanol or isobutanol, the distillation curve will differ from what is specified in ASTM D4814, even though the blend has similar, if not identical, engine performance compared to unblended gasoline. For this reason, the distillation curve specification is not used to describe the gasoline compositions of the present invention.

The vapor liquid ratio specification describes the amount of vapor that forms above a given volume of liquid gasoline at atmospheric pressure, and is a measure of the volatility of the gasoline. The vapor liquid ratio specification has both performance and environmental impact implications. The performance aspect of the test measures the tendency of the fuel to form combustible vapor mixtures inside the engine, and the environmental impact aspect of measures the tendency of the fuel to release volatile organic compounds into the environment. The optimum vapor liquid ratio of a gasoline mixtures is a balance between being just volatile enough to perform well in an engine, but not too volatile to leak from fuel tanks in volumes that are detrimental to air quality. The vapor liquid ratio is measured using ASTM method D2533. The specification for vapor liquid ratio is a maximum ratio of 20 at a given temperature, depending upon the season that the gasoline is used. In general, higher ratio blends (ones containing increased amounts of more volatile compounds) are used in the winter months. The temperature at which a vapor liquid ratio reaches 20 puts the mixture into a vapor lock class which determines, in conjunction with other fuel properties, which time of year, and where in the country, the gasoline can be used. The gasoline blends embodied herein meet the vapor liquid ratio specifications appropriate for each season and in each state of the United States. Additionally, refinery products that fail to meet ASTM gasoline specifications and state and federal regulations for vapor pressure may be brought into specification by blending in compositions of the present invention that lower the vapor pressure without altering other fuel properties.

Vapor pressure measures the tendency of the mixture to vaporize from its liquid surface and, as described above, affects both engine performance and environmental impact of the gasoline. Vapor pressure can be measured a number of different ways using ASTM methods D4953, D5190, D5191, and D5482. The specification for vapor pressure is a maximum of 7.8 to 15 psi at 100° F., depending upon what time of the year and where the gasoline is to be used. In some embodiments, blends of renewable hydrocarbons with gasoline have a vapor pressure that meets ASTM specifications appropriate to the time and place of its use as gasoline. In yet another embodiment, a mixture of hydrocarbons with low octane and/or high vapor pressure, e.g. raffinate from a refinery, which cannot normally be blended with gasoline in high proportions is brought into ASTM specification by blending such hydrocarbon mixtures with compositions of the present invention.

Aviation gasoline (Avgas) is used in aircraft with internal combustion reciprocating piston engines. The Wankel engine is another type of internal combustion engine, which uses a rotary design to convert pressure into a rotating motion, and can also use Avgas. There are many different models of piston engine aircraft, such as Husky, Eagle, Pitts, Cessna, Piper, and Bellanca, which use different grades of Avgas. Aviation gasoline has a very high octane number which generally requires that it primarily be compromised of highly branched alkanes such as isooctane. Ideally, aviation gasoline is a mixture of $C_5$ to $C_8$ hydrocarbons that as a mixture meet the key ASTM specifications for aviation gasoline in ASTM D910. Usually, because of inefficiencies in refinery operations, the octane number of the branched hydrocarbons used to make aviation gasoline is less than 100. To increase the octane number of this material, tetraethyl lead is added. The invention described herein, especially when the biofuel precursor used to make renewable aviation gasoline is isobutanol, produced primarily $C_8$ aliphatic hydrocarbons with octane numbers not higher than 100.

Tetraethyl lead (TEL) was used in automotive and aviation gasoline fuels as octane enhancer for many decades. After passing the "Clean Air Act" in 1972, EPA launched an initiative to phase out TEL from automotive gasoline fuel. Although TEL has been banned in automotive gasoline fuel, it is still being used in aviation gasoline. TEL is a toxic material and Environmental Protection Agency has realized the implication of the airborne lead on health. In addition, aviation gasoline contains sulfur and high levels of aromatics. The impact of sulfur dioxide as an air pollutant is well researched and reported. At the present time, most aviation gasoline, especially high octane aviation gasoline, contains TEL in part to satisfy the high octane requirement. For example, aviation gasoline 100 (Avgas 100) contains 0.77 g/L of TEL. Moreover, most aviation gasoline contains a high percentage of aromatics and sulfur as stated in ASTM D910. Renewable fuels with inherently high octane number require less aromatics and TEL to meet aviation gasoline specifications.

In contrast to fuels, fine chemicals are characterized by their chemical composition rather than their physical and performance properties. However, when used as raw materials in manufacturing processes, fine chemicals are generally required to have certain characteristics such as minimum purity levels. When fine chemicals are prepared from petroleum-based feedstocks, such purity levels can be difficult and/or expensive to achieve since petroleum-based feedstocks often comprise complex mixtures of hydrocarbons from which the desire starting material must be separated.

For example, xylenes are converted into either phthalic acid or phthalate esters by oxidation over a transition metal-containing catalyst (see for example, *Ind. Eng. Chem. Res.* 2000, 39, p. 3958-3997 for a review of the literature). Terephthalic acid (TPA) is the preferred form for conversion into PET, but until recently it was difficult to produce TPA in a pure enough form for PET production. Dimethyl terephthalate (DMT) was traditionally produced in a purer form than the TPA and can be used to manufacture PET as well. DMT is produced by esterification of the raw product of the TPA reactions described above with methanol and purification by distillation. A single step process to produce DMT by oxidizing xylene in the presence of methanol was developed by DuPont but is not often used due to low yields. All of these processes also produce monomethyl esters of the phthalates which are hydrolyzed to form the di-acids or further esterified to form dimethyl esters. Methods for producing TPA and DMT are taught in U.S. Pat. Nos. 2,813,119; 3,513,193; 3,887,612; 3,850,981; 4,096,340; 4,241,220; 4,329,493; 4,342,876; 4,642,369; and 4,908,471).

TPA is produced by oxidizing p-xylene in air or oxygen over a catalyst containing manganese and cobalt, although nickel catalysts have also been used with some success. Acetic acid is used as a solvent for these oxidation reactions and a bromide source such as hydrogen bromide, bromine, or tetrabromoethane is added to encourage oxidation of both methyl groups of the xylene molecule with a minimum of by-products. The temperatures of the reactions are generally kept between 80-270° C. with residence times of a few hours. TPA is insoluble in acetic acid at lower temperatures (i.e. below 100° C.), which allows separation and purification of TPA by precipitation or crystallization. Similar methods are also used to prepare isophthalic acid from m-xylene, or phthalic acid from o-xylene. However, xylenes are conventionally obtained by distillation from petroleum, from which it is difficult to obtain sufficiently pure p-xylene free of m-xylene. Thus, contamination of a desired xylene isomer (e.g., p-xylene) with an unwanted xylene isomer (e.g., m-xylene) results in a mixture of e.g., isophthalic acid and terephthalic acid which can be difficult to separate. However, as described herein, the processes of the present invention are capable of providing renewable fine chemicals having higher purity than conventional petroleum-derived fine chemicals because the renewable precursors for preparing renewable fine chemicals are generally relatively pure compounds or simple mixtures of compounds (e.g. alcohols) rather than complex mixtures of aliphatic, aromatic, and olefinic hydrocarbons. For example, the process of the present invention can be used to obtain terephthalic acid (or esters thereof) at higher levels of purity compared to petroleum-derived terephthalic acid by providing the starting p-xylene at higher levels of purity (as described herein) compared to p-xylene obtained by distillation from petroleum. Similarly, the process of the present invention can provide phthalic acid or isophthalic acid (or esters thereof) at relatively high purity compared to conventional methods by providing the respective o-xylene or m-xylene starting materials at relatively high purity levels.

The compositions of the present invention are produced by reacting precursors, e.g. isobutanol or isopentanol, produced by biocatalysts from biomass-derived feedstocks, in the presence of one or more chemical catalysts, typically a heterogeneous catalyst, to produce mixtures of hydrocarbons that meet the fuel-defining ASTM specifications for the respective fuel (e.g., gasoline, diesel, or jet fuel). Renewable fine chemicals can likewise be prepared by appropriate oxidation of one or more hydrocarbons produced by the processes of the present invention described herein (e.g., an olefin or aromatic hydrocarbon). The catalyst or catalysts can catalyze a single reaction (e.g., dehydration) or can catalyze several reactions (e.g., dehydration, isomerization, and oligomerization).

Although the specific organic compounds of the biofuels and biofuel precursors of the present invention can also be obtained from refineries using crude oil starting materials, biofuels and biofuel precursors produced via the fermentation of carbon sources such as carbohydrates and other biologically-derived materials, are qualitatively different and have different fuel properties compared to compositions prepared from petroleum-derived sources. For example, as noted above, petroleum-derived fuels are distilled from a complex mixture of hydrocarbons, whereas the biofuels of the present invention are typically prepared by the dehydration, oligomerization, and hydrogenation of a single alcohol (e.g. isobutanol) or a mixture of a few different $C_2$-$C_6$ alcohols, and thus have quite different chemical compositions as the oligomers provided in a subsequent oligomerization step (as discussed herein) are formed from integral numbers of the intermediate olefins. For example, biofuels of the present invention prepared from isobutanol would typically consist of a mixture of branched $C_8$, $C_{12}$, $C_{16}$ hydrocarbons; biofuels prepared from methylbutanols (e.g. 2-methyl-1-butanol or 3-methyl-1-butanol) would typically consist of branched $C_{10}$, $C_{15}$, $C_{20}$ hydrocarbons, etc., whereas petroleum-based fuels would include both linear and branched hydrocarbons, including $C_9$, $C_{10}$, $C_{11}$, $C_{13}$, $C_{14}$ hydrocarbons, etc. Thus, biofuels prepared by the claimed process are compositionally different from conventional petroleum-based fuels.

In most embodiments of the present invention, the biofuel, biofuel precursors, or fine chemical precursors are produced by biocatalysts that convert carbon sources derived from biomass into the biofuels, biofuel precursors, or fine chemical precursors. Suitable carbon sources include any of those described herein such as starch, pre-treated cellulose and hemicellulose, lignin, and pectin. The carbon source is converted into a biofuel, biofuel precursor, or fine chemical precursor such as n-butanol or isobutanol by the metabolic action of the biocatalyst (or by thermochemical methods, e.g. using Fischer-Tropsch catalysts). The carbon source is consumed by the biocatalyst and excreted as a biofuel, biofuel precursor, or fine chemical precursor in a large fermentation vessel. The biofuel, biofuel precursor, or fine chemical precursor is then separated from the fermentation broth, optionally purified, and in the case of biofuel or fine chemical precursors, subjected to further processes such as dehydration, oligomerization, hydrogenation, isomerization, aromatization, alkylation, blending, oxidation etc. to form a biofuel or renewable fine chemical.

In most embodiments of the present invention, the biocatalyst produces a $C_3$-$C_6$ alcohol or mixture of alcohols. For example, the biocatalyst can be a single microorganism capable of forming more than one type of alcohol during fermentation (e.g. propanols and butanols). In most embodiments however, a particular microorganism preferentially forms a particular alcohol (e.g. isobutanol) during fermentation. In alternative embodiments, the fermentation can be carried out with a mixture of different organisms, each producing a different alcohol during fermentation, or different alcohols produced in different fermentations using different organisms can be combined, thereby providing a mixture of two or more different alcohols.

Any suitable organism can be used in the fermentation step of the process of the present invention. For example, 2-propanol is produced by various *Clostridia* strains including *Clostridium beijerinkii* (Journal of Bacteriology, 1993, p. 5907-5915). Additionally, higher molecular weight alcohols such as isobutanol and various pentanols including isopentanol are produced by yeasts during the fermentation of sugars into ethanol. These fusel alcohols are known in the art of industrial fermentations for the production of beer and wine and have been studied extensively for their effect on the taste and stability of these products. Recently, production of fusel alcohols using engineered microorganisms has been reported (U.S. Patent Application No. 2007/0092957, and Nature, 2008, 451, p. 86-89).

Alcohols prepared by fermentation in the process of the present invention include at least one of 1-propanol, 2-propanol, 1-butanol, 2-butanol, isobutanol, 1-pentanol, 2-pentanol, 3-pentanol, 2-methyl-1-butanol, 3-methyl-1-butanol, 1-hexanol, 2-hexanol, 3-hexanol, 2-methyl-1-hexanol, 3-methyl-1-hexanol, or 4-methyl-1-hexanol.

Alternatively, the alcohols used to prepare the renewable compositions of the present invention can be produced by converting biomass into a mixture of alcohols at high heat over a catalyst containing copper, aluminum, chromium, manganese, iron, cobalt, or other metals and alkali metals such as lithium, sodium, and/or potassium (Energy and Fuels, 2008, 22, p. 814-839). The separate alcohols, including butanols and pentanols, optionally can be separated from the mixture by distillation and used to renewable compositions or compounds as described herein, or the mixtures can be directly treated with appropriate catalyst(s) in subsequent processing steps, as described herein to make renewable compounds, such as mixtures of aromatic compounds to blend with fuels.

The processes of the present invention for making renewable compositions, as described herein, begin with the formation of alcohols from biomass. In one embodiment, the alcohols are formed by fermentation, and the alcohol produced during fermentation is removed from the feedstock by various methods, for example fractional distillation, solvent extraction (e.g., with a renewable solvent such as renewable oligomerized hydrocarbons, renewable hydrogenated hydrocarbons, renewable aromatic hydrocarbons, etc. prepared as described herein), adsorption, pervaporation, etc. or by combinations of such methods, prior to dehydration. In other embodiments, the alcohol produced during fermentation is not isolated from the feedstock prior to dehydration, but is dehydrated directly as a dilute solution in the feedstock.

In a particular embodiment, the alcohol produced during fermentation of the feedstock is isobutanol, which is removed from the feedstock in the vapor phase under reduced pressure (e.g. as a water/isobutanol azeotrope). In a very particular embodiment, the fermentor itself is operated under reduced pressure without the application of additional heat (other than that used to provide optimal fermentation conditions for the microorganism) or the use of distillation equipment, whereby the alcohol (e.g., isobutanol) is removed as an aqueous vapor (or azeotrope). This latter embodiment has the advantage of providing for separation of the alcohol without the use of energy intensive or equipment intensive unit operations, as well as continuously removing a metabolic by-product of the fermentation and thereby improves the productivity of the fermentation process. In other embodiments, the aqueous isobutanol removed from the fermentation is then further concentrated from the water/isobutanol azeotrope by phase separation of the isobutanol phase. The resulting wet isobutanol can then be dried or dehydrated to isobutylene directly.

The post-fermentation processes for converting alcohols (e.g. $C_3$ to $C_6$ alcohols) to renewable compositions (e.g., biofuels comprising $C_6$-$C_{24}$ hydrocarbon mixtures) may be carried out separately, or may be combined. For example, when the biofuel precursor is isobutanol, the dehydration step (e.g., forming isobutene) and oligomerization step (e.g. forming dimers, trimers, etc.) can be carried out separately or combined into a single process whereby isobutanol is contacted with a single catalyst which catalyzes both dehydration and oligomerization. Similarly, hydrogenation of the unsaturated dimers, trimers, etc., formed during oligomerization can be carried out as a separate step, or can be effected during dehydration and/or oligomerization by the appropriate selection of catalyst and reaction conditions (e.g., temperature, hydrogen partial pressure, etc.).

As described herein, the various unit operations of the process of the present invention (e.g., dehydration, oligomerization, alkylation, hydrogenation, aromatization, oxidation, etc.) can be carried out in different reaction zones, or two or more chemically compatible unit operations can be carried out in the same reaction zone, wherein the different reaction zones can be in the same or different reactor vessels. When different unit operations are carried out in the same reaction zone, the appropriate catalysts can be physically mixed in the same reaction zone, or in other embodiments the different catalysts can be combined on a single support. The unit operations employed will depend on the nature of the ultimate renewable product desired. For example, processes for preparing biofuels or biofuel precursors can include dehydration, oligomerization, and hydrogenation (and optionally aromatization and alkylation), whereas processes for preparing renewable acrylates can include dehydration, optionally oligomerization, oxidation, and esterification, and processes for preparing renewable phthalates can include dehydration, optionally oligomerization, aromatization, oxidation, and esterification.

The first reaction catalyzed is the dehydration of the alcohol biofuel precursor, e.g. isobutanol or isopentanol, into the corresponding alkene, e.g. isobutylene or isopentene. Depending upon the catalyst, dehydration of the alcohol can also be accompanied by rearrangement of the resulting alkene to form one or more isomeric alkenes. If isomerization occurs, the isomerization can occur concurrently with the dehydration, or subsequently to the dehydration.

The dehydration of alcohols to alkenes can be catalyzed by many different catalysts. In general, acidic heterogeneous or homogeneous catalysts are used in a reactor maintained under conditions suitable for dehydrating the alcohol. Typically, the alcohol is activated by an acidic catalyst to facilitate the loss of water. The water is usually removed from the reaction zone with the product. The resulting alkene either exits the reactor in the gas or liquid phase (e.g., depending upon the reactor conditions) and is captured by a downstream purification process or is further converted in the reactor to other compounds as described herein. For example, t-butyl alcohol is dehydrated to isobutylene by reacting it in the gas phase at 300-400° C. over an acid treated aluminum oxide catalyst (U.S. Pat. No. 5,625,109) or in the liquid phase at 120-200° C. over a sulfonic acid cationic exchange resin catalyst (U.S. Pat. No. 4,602,119). The water generated by the dehydration reaction exits the reactor with unreacted alcohol and alkene product and is separated by distillation or phase separation. Because water is generated in large quantities in the dehydration step, the catalysts used are generally tolerant to water and a process for removing the water from substrate and product may be part of any process that contains a dehydration step. For this reason, it is possible to use wet (i.e., up to 95% water by weight) alcohol as a substrate for a dehydration reaction and remove this water with the water generated by the dehydration reaction. For example, dilute aqueous solutions of ethanol (up to 98% water by weight) can be dehydrated over a zeolite catalyst with all water removed from the ethylene product stream after the dehydration step occurs (U.S. Pat. Nos. 4,698,452 and 4,873,392). Additionally, neutral alumina and zeolites will dehydrate alcohols to alkenes but generally at higher heats and pressures than the acidic versions of these catalysts. For example, neutral chromium treated alumina will dehydrate isobutanol to isobutylene above 250° C. (U.S. Pat. No. 3,836,603).

In one embodiment of the invention described herein, the first step in a process to form a fuel is a dehydration step where aqueous mixtures of biofuel precursors that are alcohols, e.g. isobutanol, are fed into a reactor containing an acidic solid phase catalyst and heated such that the alcohol is converted into an alkene, e.g. isobutylene.

In other embodiments, the aqueous alcohol mixtures comprise about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% water, inclusive of all values, ranges, and subranges therebetween.

The alkene formed in the dehydration step can be transferred directly to the oligomerization catalyst (e.g., in another reaction zone or another reactor), or can be isolated prior to oligomerization. In one embodiment, the alkene is isolated as a liquid and optionally purified (e.g., by distillation) prior to oligomerization. Isolation of the alkene (or olefin) is advantageous in that the dehydration process is optimally carried out under gas-phase conditions to remove water vapor, whereas the oligomerization is optimally carried out under liquid-phase conditions, and thus isolation of the alkene allows the dehydration and oligomerization reactions to both be carried out under optimal conditions. Isolation of the alkene can refer to a process in which the alcohol produced by the biocatalyst (or thermochemical process) is continuously removed from the fermentor and dehydrated continuously to provide alkene. The alkene can then be stored and later reacted further (e.g., oligomerization and/or aromatization and/or hydrogenation and/or oxidation), or the isolated alkene can be temporarily stored in a holding tank prior to e.g. oligomerization providing an integrated, continuous process in which each of the unit operations (e.g., fermentation, dehydration, oligomerization, optional aromatization, optional alkylation, optional dehydration, optional oxidation, optional distillation into various fuel fractions, etc.) run simultaneously and more or less continuously, and the isolation of the alkene provides a "buffer" to processes upsets.

The second reaction catalyzed is the oligomerization of the alkene produced by dehydration of the alcohol as described above, into unsaturated aliphatic compounds, primarily dimers, trimers, tetramers, or pentamers, etc. of the corresponding alkene (depending upon the catalyst and reaction conditions).

The renewable unsaturated aliphatic compounds prepared by oligomerization in the process of the present invention have three, two or at least one double bond. On average, the product of the oligomerizing step of the process of the present invention has less than about two double bonds per molecule, in particular embodiments, less than about 1.5 double bonds per molecule. In most embodiments, the unsaturated aliphatic compounds (alkenes) have on average one double bond.

Alkenes are reactive molecules that condense into oligomeric compounds (oligomerize) under a variety of conditions and with the assistance of several different types of both heterogeneous and homogenous catalysts (G. Busca, "Acid Catalysts in Industrial Hydrocarbon Chemistry" *Chemical Reviews*, 2007, 107, 5366-5410). Of the many ways of oligomerizing alkenes, the most relevant processes for the production of fuels and fine chemicals depend upon acidic solid phase catalysts such as alumina and zeolites (e.g. U.S. Pat. No. 3,997,621; U.S. Pat. No. 4,663,406; U.S. Pat. No. 4,612,406; U.S. Pat. No. 4,864,068; U.S. Pat. No. 5,962,604). Methods for controlling the molecular weight distribution of the resulting oligomers has been reported including methods which form primarily dimers including isooctane (U.S. Pat. No. 6,689,927), trimers (WO 2007/091862 A1), and tetramers and pentamers (U.S. Pat. No. 6,239,321 B1). Typical methods for controlling oligomer size include the addition of alcohols such as t-butanol and diluents such as paraffins. Additionally, higher molecular weight oligomers and polymers can be formed using similar catalysts reacting under different conditions. For example, low molecular weight polyisobutylene (up to 20,000 Daltons) can be produced using a boron trifluoride complex catalyst (U.S. Pat. No. 5,962,604).

If a mixture of different alkenes (e.g., derived from a mixture of different alcohols) is oligomerized, the resulting oligomer mixture comprises the corresponding addition products formed by the addition of two or more alkenes which can be the same or different. For example if a mixture of propenes and butenes is oligomerized, the product can comprise "binary" or "dimer" addition products such as hexenes, heptenes, octenes; "ternary" or "trimer" addition products such as nonenes, decenes, undecenes, dodecenes, etc. Isobutylene is especially useful as a key intermediate in the oligomerization reaction because it forms primarily branched hydrocarbons that are essential to meeting gasoline and jet fuel ASTM specifications. In some embodiments, the oligomerization reaction may be omitted, for example if the desired product is a renewable fine chemical which can be prepared directly from the alkene produced in the dehydration reaction (e.g., acrylates can be produced by oxidation of propene followed by esterification). Alternatively, in other embodiments fine chemicals may be prepared by a process incorporating oligomerization, e.g. if the ultimate fine chemical has a higher carbon number than the carbon number of the alcohol produced in the fermentation step. For example, if the desired fine chemical is a methacrylate (i.e., four carbon atoms), and the alcohol produced in the fermentation is ethanol (i.e., two carbon atoms), dimerization of the ethylene produced in the dehydration step would provide butenes which can be oxidized to methacrylate.

The third reaction catalyzed is the rearrangement of the alkene monomer during oligomerization to introduce new branching patterns into the hydrocarbon products. Rearrangement can be important in achieving a mixture of branched hydrocarbons that best meets gasoline and jet fuel specifications without the need for oligomerizing a mixture of alkenes, derived from the corresponding mixture of alcohols. In some embodiments, rearrangement of the alkene may not be desired if the intended product is a fine chemical, or if a particular alkene isomer is the desired product.

During the oligomerization reaction described above, alkyl and hydride group shifts occur that result in a mixture of isomers of oligomerization products (U.S. Pat. No. 5,962,604). In some cases, isomerization of the oligomers is not desired because it can affect the overall physical properties of the material that is being produced in unpredictable ways. In other cases, isomerization is preferred, especially if the starting alkene is deficient in certain key properties. For example, melting points of polymers made from n-butylene can be decreased by isomerizing the n-butylene to isobutylene before or during the polymerization (U.S. Pat. No. 6,323,384; U.S. Pat. No. 5,107,050: U.S. Pat. No. 6,111,160) using catalysts and processes specifically designed to isomerizes these compounds. Degree of branching is a key parameter that affects many of the physical properties related to the performance of jet and diesel fuel. For example, the more branched an alkane, the lower the melting point. For a mixture of alkanes with a given molecular weight distribution, the mixture containing more branched alkanes will have a lower freezing point. Additionally, the acyclic alkanes in petroleum-based jet and diesel fuels are present in most of their possible isomers, giving these fuels their signature ranges of cold flow properties, ignitability, and energy density. Biofuels that are jet or diesel fuels will generally be more successful replacements if they, too, contain mixtures of isomers.

In some embodiments the dehydration and oligomerization/rearrangement steps can be carried out separately. In other embodiments, the dehydration and oligomerization/rearrangement are carried out in a single reaction zone using a catalyst which catalyzes both reactions.

The fourth reaction catalyzed (particularly for the production of biofuels) is the conversion of the alkene bonds in these hydrocarbon products into heat-stable saturated hydrocarbons (e.g., by hydrogenation). As indicated above, this reaction may be omitted in various embodiments of the processes of the present invention, when the desired product is not an alkane.

In most embodiments, the renewable saturated aliphatic compound formed after hydrogenation in the process of the present invention is fully saturated or partially saturated. On average, the product of said hydrogenating step has less than about 0.5 double bonds per molecule, in particular embodiments less than about 0.2 double bonds per molecule.

As described herein, some renewable compositions such as biofuels or renewable fine chemicals comprise aromatic compounds, in which case the process of the present invention can include an aromatization step, either as a separate process or as a unit operation integrated into the process. In some embodiments, alkenes prepared by dehydration of a renewable alcohol (e.g. obtained by fermentation) are contacted with the appropriate aromatization catalyst to provide renewable aromatic compounds. In other embodiments, unsaturated oligomers obtained from the oligomerization of alkenes are aromatized to provide higher molecular weight aromatics (e.g. typically more highly alkylated aromatics).

In some embodiments, each of the above unit operations can be carried out in separate reaction zones. Alternatively, in other embodiments various unit operations can be combined in a single reaction zone, whereby intermediates are immediately converted into the desired product. For example, a single reaction zone can contain the appropriate catalyst or mixture of catalysts whereby a renewable alcohol can be dehydrated and immediately oligomerized, or can be dehydrated, oligomerized, and aromatized, or can be dehydrated, oligomerized, and hydrogenated etc.

For the production of biofuels, once the starting material, e.g. isobutanol or isopentanol, is loaded into the reactor with the catalyst(s), the reaction is maintained at a temperature and pressure (and if needed, under a reducing atmosphere such as $H_2$) that produces a mixture of hydrocarbons that meets the appropriate biofuel specifications. The resulting products are then separated (or removed) from the reactor, optionally purified, and optionally blended with aromatics produced from the starting material in a separate reaction to meet the appropriate biofuel specifications. In processes of the present invention incorporating aromatization as a unit operation, the hydrogen produced as a byproduct can be used to reduce alkenes (e.g. alkenes produced by dehydration of alcohols and/or oligomeric alkenes produced in the oligomerization step) to saturated hydrocarbons. Thus in some embodiments of the process of the present invention, virtually all carbon and hydrogen in the biofuel is renewable. Alternatively, the hydrogen or other reducing agent can be supplied from other sources.

In some embodiments of the process of the present invention, the process is carried out in an apparatus having a single reactor with one or more reaction zones in which various unit operations are carried out (e.g. dehydration, polymerization, hydrogenation, etc.). In other embodiments, the process of the present invention may require two or more reactors, each with one or more reaction zones, in which the two or more reactors are appropriately interconnected to provide an integrated process. For example, renewable jet fuels which comprise a mixture of hydrocarbons and aromatics can be prepared in an apparatus in which one or more of dehydration, oligomerization, alkylation, and hydrogenation are carried out in one or more reactors containing one or more reaction zones, and aromatization is carried out in a separate reactor, such that a portion of the alkenes and/or alkene oligomers formed in the dehydration and/or oligomerization reaction zones are fed to the aromatization reactor. The aromatic compounds formed in the aromatization reactor can then be collected and/or mixed with the alkanes formed after hydrogenation, or further alkylated (e.g., in a separate alkylation reaction zone or in the oligomerization reactions) before being collected and/or mixed with the alkanes formed after hydrogenation. In addition, the hydrogen produced during aromatization can be used in the hydrogenation reaction zone.

The process of the present invention can be optimized to provide a specific biofuel or a specific biofuel precursor, or can be optimized to produce a mixture of renewable hydrocarbons which can be separated into two or more different product streams, each of which is a different biofuel (e.g. renewable diesel or renewable jet fuel) or a different biofuel precursor (e.g. octane isomers or dodecane isomers), or one of the different product streams can be a particular biofuel, and another different product streams can be a particular biofuel precursor.

Alternatively, the process of the present invention can be designed such that by modification of process conditions (e.g., temperature, pressure, or selection of catalyst, etc.) a particular feedstock can be converted to any particular desired biofuel or biofuel precursor. For example, the process can be designed such that by changing process conditions one could obtain either renewable diesel fuel or renewable jet fuel.

The biofuel precursors can include a pure alcohol (e.g., isobutanol) or can be a mixture of different $C_2$-$C_6$ alcohols, produced either by conversion of a feedstock with a mixture of different microorganisms, or by the combination of different $C_2$-$C_6$ alcohols produced by separately fermenting feedstocks in the presence of different microorganisms which preferentially produced different alcohols. For example, ethanol and isobutanol, separately produced by different fermentation processes can be combined and subjected to dehydration, oligomerization, hydrogenation, and optionally aromatization processes. Alternatively, biofuel precursors can include alkenes or oligomers (e.g., alkene dimers, trimers, etc.) which when added to hydrocarbon mixtures can improve the properties of the resulting composition to comply with the appropriate ASTM fuel specifications. For example, addition of biofuel precursors to hydrocarbon mixture can improve the octane (e.g. MON and RON values) or cetane values, or improve low temperature performance of the fuel, etc.

The biofuels described in this invention can comprise mixtures of hydrocarbons with molecular weight distributions similar to those of petroleum-derived fuels, i.e. the biofuel that replaces jet fuel is a mixture of linear and branched hydrocarbons with a molecular weight distribution centered around hydrocarbons containing 12 carbon atoms. These biofuels are produced from biofuel precursors such as isobutanol and isopentanol by reacting the precursors in chemical reactors containing catalysts that convert the precursors into mixtures of hydrocarbons that fit the typical profile of jet fuel. However, biofuels produced by the processes of the present invention from a relatively pure precursor such as isobutanol or 2-methyl-1-butanol would produce mixtures of hydrocarbons which are (or are derived from) dimers, trimer, tetramers, etc. of the alkene produced by dehydration of the corresponding alcohol.

In one embodiment, a relatively pure biofuel precursor, e.g. isobutanol, formed by the fermentation of a biomass-derived feedstock is dehydrated in a chemical reactor that contains a solid phase catalyst that catalyzes both the dehydration and oligomerization of the alcohol to form precursors to, or forms gasoline, jet or diesel fuels. In another embodiment, an aqueous solution of biofuel precursor is fed to a chemical reactor that contains a solid phase catalyst that catalyzes both the dehydration and oligomerization of the alcohol to form precursors to, or forms gasoline, jet or diesel fuels. In another embodiment, an alkene, e.g. isobutylene, formed by the dehydration of a biofuel precursor, e.g. isobutanol, is fed into a chemical reactor containing a catalyst that catalyzes the oligomerization of the alkene to form precursors to, or forms gasoline, jet or diesel fuels. In yet another embodiment, water and alkene, e.g. isobutylene, formed by the dehydration of a biofuel precursor, e.g. isobutanol, is fed into a chemical reactor containing a catalyst that catalyzes the oligomerization of the alkene to form precursors to, or forms gasoline, jet or diesel fuels. In a particular embodiment, the jet fuel produced by the dehydration and oligomerization of isobutanol produced by fermentation is comprised of a distribution of oligomers of isobutylene in which a majority of the isomers are trimers of isobutylene containing 12 carbon atoms. In another particular embodiment, the diesel fuel produced by the dehydration and oligomerization of isobutanol reviews by fermentation is comprised of a distribution of oligomers of isobutylene in which a majority of the isomers are tetramers of isobutylene containing 16 carbon atoms. In still another particular embodiment, the gasoline produced by the dehydration and oligomerization of isobutanol produced by fermentation is comprised of a distribution of oligomers of isobutylene in which a majority of the isomers are dimers of isobutylene containing 8 carbon atoms. The oligomerization products are further reduced to saturated hydrocarbons by hydrogen, in some embodiments derived from the aromatization of a second stream of alcohol or alkene, as described herein. In a particular embodiment, these aromatics are blended with the saturated hydrocarbons (e.g. trimers of isobutylene) to produce jet fuel that meets ASTM specifications.

In one embodiment of the invention described herein, a biofuel precursor, e.g. isobutanol, formed by the fermentation of a biomass-derived feedstock is dehydrated in a chemical reactor that contains a solid phase catalyst that catalyzes both the dehydration, oligomerization, and partial rearrangement of the alcohol to form precursors to or to form jet fuels with increased isomer diversity, relative to a product formed by oligomerization without rearrangement, in the final product. In another embodiment, a linear biofuel precursor, e.g. n-butanol, formed by the fermentation of a biomass-derived feedstock is dehydrated in a chemical reactor that contains a solid phase catalyst that catalyzes both the dehydration, oligomerization, and rearrangement of the alcohol to form precursors to, or which forms gasoline, jet or diesel fuel with increased branching and isomer diversity, relative to a product formed by oligomerization without rearrangement, in the final product. In another embodiment, the biofuel precursor undergoing dehydration, oligomerization, and rearrangement is fed to the reactor as an aqueous solution. In yet another embodiment, the biofuel precursor is converted into an alkene in a separate reactor, and the alkene is fed into a reactor where it is oligomerized and rearranged to form precursors to, or which forms gasoline, jet or diesel fuels with increased branching and isomer diversity, relative to a product formed by oligomerization without rearrangement, in the final product. In a particular embodiment, the jet fuel produced by the dehydration, oligomerization, and rearrangement of isobutanol produced by fermentation is comprised of a distribution of oligomers of butylenes in which a majority of the isomers are trimers of butylenes containing 12 carbon atoms. In another embodiment, the diesel fuel produced by the dehydration, oligomerization, and rearrangement of isobutanol produced by fermentation is comprised of a distribution of oligomers of butylenes in which a majority of the isomers are tetramers of butylenes containing 16 carbon atoms. In still another embodiment, the gasoline produced by the dehydration, oligomerization, and rearrangement of isobutanol produced by fermentation is comprised of a distribution of oligomers of butylenes in which a majority of the isomers are dimers of butylenes containing 8 carbon atoms. The oligomerization products are subsequently reduced to saturated hydrocarbons by hydrogen derived from the aromatization of a second stream of alcohol or alkene, as described herein. These aromatics are blended with the saturated hydrocarbons to produce gasoline, jet or diesel fuel that meets ASTM specifications.

Suitable acid catalysts are selected from the group consisting of inorganic acids, organic sulfonic acids, heteropolyacids, perfluoroalkyl sulfonic acids, metal salts thereof, mixtures of metal salts, and combinations thereof. The acid catalyst may also be selected from the group consisting of zeolites such as CBV-3020, ZSM-5, β Zeolite CP 814C, ZSM-5 CBV 8014, ZSM-5 CBV 5524 G, and YCBV 870; fluorinated alumina; acid-treated silica; acid-treated silica-alumina; acid-treated titania; acid-treated zirconia; heteropolyacids supported on zirconia, titania, alumina, silica; and combinations thereof. The acid catalyst may also be selected from the group consisting of metal sulfonates, metal sulfates, metal trifluoroacetates, metal triflates, and mixtures thereof; mixtures of salts with their conjugate acids, zinc tetrafluoroborate, and combinations thereof.

Other acid catalysts that may be employed in this process of the invention include inorganic acids such as sulfuric acid, phosphoric acid, hydrochloric acid, and nitric acid, as well as mixtures thereof. Organic acids such as p-toluene sulfonic acid, triflic acid, trifluoroacetic acid and methanesulfonic acid may also be used. Moreover, ion exchange resins in the acid form may also be employed. Hence, any type of acid catalyst known in the art may be employed.

Fluorinated sulfonic acid polymers can also be used as acid catalysts for the process of the present invention. These acids are partially or totally fluorinated hydrocarbon polymers containing pendant sulfonic acid groups, which may be partially or totally converted to the salt form. One particularly suitable fluorinated sulfonic acid polymer is Nafion® perfluorinated sulfonic acid polymer, (E.I. du Pont de Nemours and Company, Wilmington, Del.). One preferred form is Nafion® Super Acid Catalyst, a bead-form strongly acidic resin which is a copolymer of tetrafluoroethylene and perfluoro-3,6-dioxa-4-methyl-7-octene sulfonyl fluoride, converted to either the proton (H+), or the metal salt form.

A soluble acid catalyst may also be used during the method of the invention. Suitable soluble acids include, those acid catalysts with a pKa less than about 4, preferably with a pKa less than about 2, including inorganic acids, organic sulfonic acids, heteropolyacids, perfluoroalkylsulfonic acids, and combinations thereof. Also suitable are metal salts of acids with pKa less than about 4, including metal sulfonates, metal sulfates, metal trifluoroacetates, metal triflates, and mixtures thereof, including mixtures of salts with their conjugate acids. Specific examples of suitable acids include sulfuric acid, fluorosulfonic acid, phosphoric acid, p-toluenesulfonic acid, benzenesulfonic acid, phosphotungstic acid, phosphomolybdic acid, trifluoromethanesulfonic acid, 1,1,2,2-tetrafluoroethanesulfonic acid, 1,2,3,2,3,3-hexapropanesulfonic acid, bismuth triflate, yttrium triflate, ytterbium triflate, neodymium triflate, lanthanum triflate, scandium triflate, zirconium triflate, and zinc tetrafluoroborate.

For batch reactions, the acid catalyst is preferably used in an amount of from about 0.01% to about 50% by weight of the reactants, although the concentration of acid catalyst may exceed 50% if the reaction is run in continuous mode using a packed bed reactor. A preferred range is 0.25% to 5% by weight of the reactants unless the reaction is run in continuous mode using a packed bed reactor. For flow reactors, the acid catalyst will have WHSV values ranging from 0.1 to 20.

Other suitable heterogeneous acid catalysts include, for example, acid treated clays, heterogeneous heteropolyacids and sulfated zirconia. The acid catalyst can also be selected from the group consisting of sulfuric acid-treated silica, sulfuric acid-treated silica-alumina, acid-treated titania, acid-treated zirconia, heteropolyacids supported on zirconia, heteropolyacids supported on titania, heteropolyacids supported on alumina, heteropolyacids supported on silica, and combinations thereof. Suitable heterogeneous acid catalysts include those having an $H_0$ of less than or equal to 2.

The oligomerization process described above produces hydrocarbons that may contain at least one double bond. In general, double bonds are very reactive and their presence in, for example jet fuel, is not desirable because they will spontaneously polymerize in an engine, which may cause damage. Accordingly, in most embodiments of processes for preparing jet fuel according to the present invention, such double bonds are removed by hydrogenation, for example using hydrogen gas derived from the aromatization of isobutanol or hydrocarbon derivatives of isobutanol (e.g., isobutylene). Alternatively, non-renewable hydrogen or other hydrogen containing compounds such as borane may be used. The reduction of the double bond is catalyzed by Group VIII metals such as palladium, nickel, cobalt, rhodium or platinum dispersed in a heterogenous catalyst material (*Advanced Organic Chemistry*, $4^{th}$ edition, J. March, 1992). In particular embodiments, the dehydration, oligomerization, rearrangement, and reduction (hydrogenation) steps are carried out in a single reactor containing a heterogenous catalyst complex capable of catalyzing all of these reactions. Alternatively, in other embodiments the oligomerized and rearranged product may be transferred into an additional reactor for reduction over a different catalyst.

In other embodiments, hydrogenation is carried out in the presence of a suitable active metal hydrogenation catalyst. Acceptable solvents, catalysts, apparatus, and procedures for hydrogenation in general can be found in Augustine, Heterogeneous Catalysis for the Synthetic Chemist, Marcel Decker, New York, N.Y. (1996).

Many hydrogenation catalysts are effective, including (without limitation) those containing as the principal component iridium, palladium, rhodium, nickel, ruthenium, platinum, rhenium, compounds thereof, combinations thereof, and the supported versions thereof.

When the hydrogenation catalyst is a metal, the metal catalyst may be a supported or an unsupported catalyst. A supported catalyst is one in which the active catalyst agent is deposited on a support material e.g. by spraying, soaking or physical mixing, followed by drying, calcination, and if necessary, activation through methods such as reduction or oxidation. Materials frequently used as supports are porous solids with high total surface areas (external and internal) which can provide high concentrations of active sites per unit weight of catalyst. The catalyst support may enhance the function of the catalyst agent; and supported catalysts are generally preferred because the active metal catalyst is used more efficiently. A catalyst which is not supported on a catalyst support material is an unsupported catalyst.

The catalyst support can be any solid, inert substance including, but not limited to, oxides such as silica, alumina, titania, calcium carbonate, barium sulfate, and carbons. The catalyst support can be in the form of powder, granules, pellets, or the like. A preferred support material of the present invention is selected from the group consisting of carbon, alumina, silica, silica-alumina, titania, titania-alumina, titania-silica, barium, calcium, compounds thereof and combinations thereof. Suitable supports include carbon, $SiO_2$, $CaCO_3$, $BaSO_4TiO_2$, and $Al_2O_3$. Moreover, supported catalytic metals may have the same supporting material or different supporting materials.

In one embodiment of the instant invention, a more preferred support is carbon. Further preferred supports are those, particularly carbon, that have a surface area greater than 100-200 $m^2/g$. Further preferred supports are those, particularly carbon, that have a surface area of at least 300 $m^2/g$. Commercially available carbons which may be used in this invention include those sold under the following trademarks: Bameby & Sutcliffe™, Darco™, Nuchar™, Columbia JXN™, Columbia LCK™, Calgon PCB™, Calgon BPL™, Westvaco™, Norit™ and Barnaby Cheny NB™. The carbon can also be commercially available carbon such as Calsicat C, Sibunit C, or Calgon C (commercially available under the registered trademark Centaur®).

Preferred combinations of catalytic metal and support system include nickel on carbon, nickel on $Al_2O_3$, nickel on $CaCO_3$, nickel on $TiO_2$, nickel on $BaSO_4$, nickel on $SiO_2$, platinum on carbon, platinum on $Al_2O_3$, platinum on $CaCO_3$, platinum on $TiO_2$, platinum on $BaSO_4$, platinum on $SiO_2$, palladium on carbon, palladium on $Al_2O_3$, palladium on $CaCO_3$, palladium on $TiO_2$, palladium on $BaSO_4$, palladium on $SiO_2$, iridium on carbon, iridium on $Al_2O_3$, iridium on $SiO_2$, iridium on $CaCO_3$, iridium on $TiO_2$, iridium on $BaSO_4$, rhenium on carbon, rhenium on $Al_2O_3$, rhenium on $SiO_2$, rhenium on $CaCO_3$, rhenium on $TiO_2$, rhenium on $BaSO_4$, rhodium on carbon, rhodium on $Al_2O_3$, rhodium on $SiO_2$, rhodium on $CaCO_3$, rhodium on $TiO_2$, rhodium on $BaSO_4$, ruthenium on carbon, ruthenium on $Al_2O_3$, ruthenium on $CaCO_3$, ruthenium on $TiO_2$, ruthenium on $BaSO_4$, and ruthenium on $SiO_2$.

Raney metals or sponge metals are one class of catalysts useful for the present invention. A sponge metal has an extended "skeleton" or "sponge-like" structure of metal, with dissolved aluminum, and optionally contains promoters. The sponge metals may also contain surface hydrous oxides, absorbed hydrous radicals, and hydrogen bubbles in pores. Sponge metal catalysts can be made by the process described in U.S. Pat. No. 1,628,190, the disclosure of which is incorporated herein by reference.

Preferred sponge metals include nickel, cobalt, iron, ruthenium, rhodium, iridium, palladium, and platinum. Sponge nickel or sponge cobalt are particularly suitable as catalysts. The sponge metal may be promoted by one or more promoters selected from the group consisting of Group IA (lithium, sodium, and potassium), IB (copper, silver, and gold), IVB (titanium and zirconium), VB (vanadium), VIB (chromium, molybdenum, and tungsten), VIIB (manganese, rhenium), and VIII (iron, cobalt, nickel, ruthenium, rhodium, palladium, osmium, iridium, and platinum) metals. The promoter can be used in an amount useful to give desired results. For example, the amount of promoter may be any amount less than 50% by weight of the sponge metal, preferably 0 to 10% by weight, more preferably 1 to 5% by weight.

Sponge nickel catalysts contain mainly nickel and aluminum. The aluminum is typically in the form of metallic aluminum, aluminum oxides, and/or aluminum hydroxides. Small amounts of other metals may also be present either in their elemental or chemically bonded form, such as iron and/or chromium, and may be added to the sponge nickel to increase activity and selectivity for the hydrogenation of certain groups of compounds. It is particularly preferred to use chromium and/or iron promoted sponge nickel as a catalyst.

Sponge cobalt catalysts also contain aluminum and may contain promoters. Preferred promoters are nickel and chromium, for example in amounts of about 2% by weight based on the weight of the catalyst. Examples of suitable sponge metal catalysts include Degussa BLM 112W, W. R. Grace Raney® 2400, Activated Metals A-4000™, and W. R. Grace Raney® 2724.

As stated above, useful catalytic metals include component iridium, palladium, rhodium, nickel, ruthenium, platinum, rhenium; and useful support materials include carbon, alumina, silica, silica-alumina, titania, titania-alumina, titania-silica, barium, calcium, particularly carbon, $SiO_2$, $CaCO_3$, $BaSO_4$ and $Al_2O_3$. A supported catalyst may be made from any combination of the above named metals and support materials. A supported catalyst may also, however, be made from combinations of various metals and/or various support materials selected from subgroup(s) of the foregoing formed by omitting any one or more members from the whole groups as set forth in the lists above. As a result, the supported catalyst may in such instance not only be made from one or more metals and/or support materials selected from subgroup(s) of any size that may be formed from the whole groups as set forth in the lists above, but may also be made in the absence of the members that have been omitted from the whole groups to form the subgroup(s). The subgroup(s) formed by omitting various members from the whole groups in the lists above may, moreover, contain any number of the members of the whole groups such that those members of the whole groups that are excluded to form the subgroup(s) are absent from the subgroup(s). For example, it may be desired in certain instances to run the process in the absence of a catalyst formed from palladium on carbon.

The optimal amount of the metal in a supported catalyst depends on many factors such as method of deposition, metal surface area, and intended reaction conditions, but in many embodiments can vary from about 0.1 wt % to about 20 wt % of the whole of the supported catalyst (catalyst weight plus the support weight). A more preferred catalytic metal content range is from about 0.1 wt % to about 10 wt % by weight of the whole of the supported catalyst. A further preferred catalytic metal content range is from about 1 wt % to about 7 wt % by weight of the whole of the supported catalyst. Optionally, a metal promoter may be used with the catalytic metal in the method of the present invention. Suitable metal promoters include: 1) those elements from groups 1 and 2 of the periodic table; 2) tin, copper, gold, silver, and combinations thereof; and 3) combinations of group 8 metals of the periodic table in lesser amounts.

Temperature, solvent, catalyst, pressure and mixing rate are all parameters that affect the hydrogenation. The relationships among these parameters may be adjusted to effect the desired conversion, reaction rate, and selectivity in the reaction of the process.

In one embodiment, the hydrogenation temperature is from about 25° C. to 350° C., more preferably from about 50° C. to about 250° C., and most preferred from about 50° C. to 200° C. The hydrogen pressure is preferably about 0.1 to about 20 MPa, more preferably about 0.3 to 10 MPa, and most preferably about 0.3 to 4 MPa. The reaction may be performed neat or in the presence of a solvent. Useful solvents include those known in the art of hydrogenation such as hydrocarbons, ethers, and alcohols (where the alcohols and ethers, or hydrocarbon solvents can be renewable). Alcohols are most preferred, particularly lower alkanols such as methanol, ethanol, propanol, butanol, and pentanol. Where the reaction is carried out according to the preferred embodiments, selectivities in the range of at least 70% are attainable where selectivities of at least 85% are typical. Selectivity is the weight percent of the converted material that is a saturated hydrocarbon where the converted material is the portion of the starting material that participates in the hydrogenation reaction.

Upon completion of the hydrogenation reaction, the resulting mixture of products may be separated by a conventional method, such as for example, by distillation, by crystallization, or by preparative liquid chromatography.

For jet fuels which must pass the very restrictive JFTOT test described above, oxygen-containing compounds are also not desired. Jet fuels containing oxygen-containing compounds which fail the JFTOT test are usually used as diesel fuels or diesel fuel precursors Petroleum-derived jet fuels are mixtures of hydrocarbons having carbon numbers distributed around $C_8$ to $C_{16}$, most of which are normal paraffins (i.e. straight chain alkanes) and isoparaffins (i.e., branched alkanes), naphthenes (i.e. cycloalkanes) and aromatics. As discussed herein, renewable jet fuels are produced by dehydration of a renewable alcohol, e.g. propanol or isobutanol, to produce alkenes, e.g. propylene or isobutylene, which undergo oligomerization in the presence of an acid catalyst. Under these conditions, the precursors are converted into mixtures of hydrocarbons, which are subsequently hydrogenated, resulting in a mixture that meets the typical specifications of jet fuel. Because the starting materials for the renewable jet fuels of the present invention are e.g., $C_3$ and i-$C_4$ alcohols, renewable jet fuel compositions will be mainly branched aliphatic hydrocarbons. However, Fisher Tropsch synthetic jet fuels have shown that the complete lack of aromatic hydrocarbons is associated with a lower density fuel and an inability to swell nitrile elastomer o-rings needed to provide adequate performance for aircraft fuel system seals. The United State Department of Defense has indicated that the minimum density requirement is of secondary importance, but it was realized that at least some aromatics are needed to provide elastomer compatibility (*Energy & Fuels* 2007, 21, 1448).

There is presently no commercial process to produce $C_6$-$C_8$ aromatics from renewable sources. Instead, $C_6$-$C_8$ aromatics are currently produced by catalytic cracking and catalytic reforming of petroleum-derived feedstocks. In particular, the catalytic reforming process uses light hydrocarbon "cuts" like liquefied petroleum gas ($C_3$ and $C_4$) or light naphtha (especially $C_5$ and $C_6$). There are three main processes for conversion of these petroleum-derived feedstocks to $C_6$-$C_8$ aromatics: M-2 Forming (Mobil), Cyclar (UOP) and Aroforming (IFP-Salutec).

In the past three decades, new catalysts have been developed to produce petrochemical grade benzene, toluene, and xylene (BTX) from low molecular weight alkanes in a single step. The process can be described as "dehydrocyclodimerization and dehydrogenation" over one catalyst and in single reaction zone. In refineries liquefied petroleum gas streams containing a mixture of $C_3$ and $C_4$ alkanes are aromatized to produce a mixture of benzene, toluene, and all three isomers of xylene. Ethyl benzene may also be produced in these reactions.

The conversion of small alkanes and alkenes into aromatic compounds, such as xylene, has been reported many times over the years using a variety of alumina and silica based catalysts and reactor configurations. For example, the Cyclar process developed by UOP and BP for converting liquefied petroleum gas into aromatic compounds uses a gallium-doped zeolite (*Appl. Catal. A*, 1992, 89, p. 1-30). Other catalysts reported in the patent literature include bismuth, lead, or antimony oxides (U.S. Pat. Nos. 3,644,550 and 3,830,866), chromium treated alumina (U.S. Pat. Nos. 3,836,603 and 6,600,081 B2), rhenium treated alumina (U.S. Pat. No. 4,229,320) and platinum treated zeolites (WO 2005/065393 A2). The conversion of alkenes and alkanes into aromatic compounds is a net oxidation reaction that releases hydrogen from the aliphatic hydrocarbons. If no oxygen is present, hydrogen gas and light alkanes such as methane and ethane are by-products. If oxygen is present, the hydrogen is converted into water. In an embodiment of the present invention, the hydrogen and light alkanes by-products are renewable sources of these compounds. In another embodiment, the renewable hydrogen and light alkanes are used in a biorefinery to produce additional renewable compounds. In a traditional refinery that produces aromatics, these light compounds are collected and used throughout the refinery. These and other light hydrocarbons ($C_3$-$C_6$) are also produced by direct cracking of the hydrocarbon feedstocks at the high heats and pressures needed to generate the aromatics. In another embodiment, these cracking products are renewable and used in a biorefinery to produce additional renewable compounds.

The hydrocarbon feedstocks used to form aromatic compounds in a conventional petroleum refinery are primarily mixtures of hydrocarbons. As a result, the aromatics produced by petroleum refineries are mixtures of aromatics, which are typically used directly in fuel blends. For chemical applications, the pure aromatic compounds must be separated and purified from these mixtures. However, in a large-scale refinery, producing pure streams of specific aromatics can be expensive and difficult.

In contrast, the process of the present invention can readily provide relatively pure aromatic compounds at a cost which is competitive with that of conventional refineries. For example, biomass derived isobutanol (e.g. from fermentation) can be dehydrated and oligomerized to diisobutylene in a reactor containing a metal-doped zeolite catalyst. The diisobutylene is then selectively converted to aromatics in high yield. Of the xylenes produced, the selectivity to p-xylene is greater than 90%. Such selectivity has been demonstrated on laboratory scale using pure t-butanol (U.S. Pat. No. 3,830,866), isobutylene (U.S. Pat. No. 3,830,866), and diisobutylene (U.S. Pat. No. 6,600,081 B2). Thus, the process of the present invention provides pure alcohol starting materials such as butanols and pentanols, as described herein, at cost competitive or lower than conventional refineries. In addition, the alkenes produced by dehydration of these alcohols in the process of the present invention are more reactive than the primarily saturated alkanes traditionally used in a refinery to produce aromatics, which allow the use of milder reaction conditions resulting in improved selectivity for the desired single product (e.g., p-xylene).

For example, renewable xylene can be prepared by the process of the present invention by aromatizing renewable isooctene. The resulting product contains only negligible amounts of renewable benzene and toluene, and predominately comprises xylene(s), from which renewable p-xylene can be recovered at very high purity.

Thus, in some embodiments of the process of the present invention, renewable aromatics—benzene, toluene, and xylene (BTX)—are produced by the dehydrocyclodimerization and dehydration of alkanes, e.g. isobutane, prepared from renewable alcohols, e.g. isobutanol, reacted with a hydrotreating catalyst. The hydrodeoxygenation process can be carried out over Co/Mo, Ni/Mo or both catalysts and in the presence of hydrogen at reasonable temperatures (e.g., ~150° C.). When isobutanol is used as a starting material in this reaction, the product is highly selective (~90%) isobutane with more than 95% conversion. The renewable alkenes, e.g. propylene or isobutylene, formed by the process of the present invention can be aromatized using various catalysts, for example zeolite catalyst, e.g. H-ZSM-5 (*Ind. Eng. Chem. Process Des. Dev.* 1986, 25, 151) or GaH-ZSM-5 (*Applied Catalysis* 1988, 43, 155), which sequentially oligomerizes the olefin, cyclizes the oligomerized olefins to naphthenes, and dehydrates the naphthene to the corresponding aromatic compound. Alternatively, a metal oxide catalyst can be used in presence of molecular oxygen. This latter type of catalyst dimerizes the olefin to the corresponding diene, which is further cyclized to the corresponding aromatic compound. Because such aromatization conditions are more severe than oligomerization conditions, these two processes are generally carried out as separate process steps.

The first step of the process to produce renewable aromatics from renewable alcohol precursors, e.g., propanol, isobutanol, or isopentanol, is the dehydration of the alcohol. For example, a renewable alcohol is fed into a reactor containing an acidic solid phase catalyst and heated to dehydrate the alcohol to an alkene, e.g. propene, isobutene, or isopentene. In the production of renewable aromatics, the dehydration step of the renewable alcohol produces almost exclusively alkenes, with are more reactive to the aromatization process than the alkanes used in conventional aromatization processes.

Alcohol Dehydration:

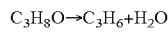

$C_3H_8O \rightarrow C_3H_6 + H_2O$

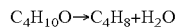

$C_4H_{10}O \rightarrow C_4H_8 + H_2O$

The second step is the conversion of alkenes to $C_6$-$C_8$ aromatics. In some embodiments, the production of renewable aromatics from renewable propylene or isobutylene is achieved according to one of the following processes:

Aromatization of light olefins using zeolites, i.e. H-ZSM-5 or GaH-ZSM-5:

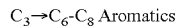

$C_3 \rightarrow C_6$-$C_8$ Aromatics

$C_4 \rightarrow C_6$-$C_8$ Aromatics

Oxidative dehydrodimerization of light olefins using metal oxide/$O_2$:

$2C_3H_6 \rightarrow C_6H_{10} \rightarrow$ benzene + $H_2O$

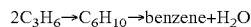

$2C_4H_8 \rightarrow C_8H_{14} \rightarrow p$-xylene + $H_2O$

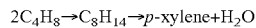

Dimerization of isobutylene to isooctene followed by its aromatization using eta-alumina doped with Cr, Zr, and other elements:

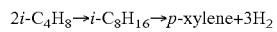

$2i$-$C_4H_8 \rightarrow i$-$C_8H_{16} \rightarrow p$-xylene + $3H_2$

In one embodiment, the invention described herein comprises an integrated process for producing jet fuel from a fermentation product such as isopropanol, n-butanol, isobutanol, isopentanol, and 2-methyl-1-butanol. The renewable jet fuel of the present invention comprises a mixture of aliphatic and aromatic hydrocarbons that meets all ASTM specifications for jet fuel. The renewable jet fuel produced from this process can be used in place of jet fuel produced by a petroleum refinery without modification of transportation, storage, and fueling equipment. The renewable jet fuel from this process can be used in existing jet turbine engines without modifying the engines. Substantially all of the carbon in the renewable jet fuel produced with this process is derived from renewable sources (e.g., at least about 90% of the carbon is derived from renewable sources). The aliphatic hydrocarbon component is produced from alcohols by a combination of dehydration, oligomerization, and reduction to saturated hydrocarbons. The aromatic component is produced by directly reacting the alcohols or their oligomers over an aromatization catalyst in an oxygen-free environment. The aromatization process produces aromatic compounds such as xylenes and other alkyl benzenes that are blended with the saturated hydrocarbons to meet ASTM specifications for jet fuel. The aromatization process also produces enough hydrogen gas to stoichiometrically reduce the oligomers to saturated hydrocarbons. Because the hydrogen is derived from the fermentation product, no additional carbon sources such as biomass or natural gas are required to produce the hydrogen needed to remove olefins from the jet fuel mixture. The carbon and hydrogen in the renewable jet fuel is completely derived from renewable sources.

For example, isobutanol can be converted into primarily p-xylene, generating 3 chemical equivalents of hydrogen gas. Isobutanol is also converted into $C_{12}$-branched oligomers. Each molecule of oligomers that is generated by the oligomerization process contains a single olefinic bond which must be converted into a saturated hydrocarbon before it is acceptable for use in a jet fuel. An ideal jet fuel which meets all key ASTM standards contains about 25 mole percent of p-xylene (or other renewable aromatics) and 75 mole percent of aliphatic hydrocarbons. To generate the 75 mole percent of saturated hydrocarbons from the olefinic oligomers, 75 mole percent of hydrogen is required. For most on-specification combinations of aromatic and aliphatic hydrocarbons, the conversion of the starting alcohol into the aromatic portion of the fuel will produce approximately as much hydrogen gas as will be needed to convert the aliphatic portion of the fuel into saturated hydrocarbon. An integrated process which starts with a single alcohol such as isobutanol will be able to produce a jet fuel that meets all ASTM specifications without the need for additional carbon or hydrogen. Alternatively, a biorefinery that produces aromatic compounds for jet fuel will produce additional aromatic compounds for use with other fuels and chemical processes, generating additional hydrogen that can be used as needed to remove olefinic compounds from the jet fuel.

Other renewable alcohols, including ethanol, 1- and 2-propanol, 1- and 2-butanol, and pentanols such as 1-, 2-, 3-pentanol, 2-methyl-1-butanol, and isopentanol, are converted to aromatic compounds using similar sets of reactions and catalysts and producing 3 equivalents of hydrogen per aromatic ring produced. These alcohols are also oligomerized to aliphatic hydrocarbons that are reduced with the hydrogen by-product to saturated compounds and blended with the aromatics to generate renewable jet fuel that meets ASTM specifications. These alcohols can be used alone or in combination with each other and/or isobutanol to produce mixtures of aromatic and aliphatic hydrocarbons that meet ASTM specifications for jet fuel. These mixtures are produced in an integrated process that does not require additional carbon and hydrogen inputs to create jet fuel from the starting alcohols.

The aromatization of propylene or isobutylene will mainly produce a BTX mixture ($C_6$-$C_8$ aromatics), which are too light for renewable jet fuel. Aromatics more suitable for use in jet fuel can be obtained by alkylation of BTX. The alkylation of aromatics is carried out industrially using mineral acids (e.g. solid phosphoric acid) and Friedel-Crafts catalysts (e.g. $AlCl_3$-HCl). One of the most commercially important examples of aromatic alkylation is the alkylation of benzene with ethylene or propylene to produce ethyl benzene and cumene, respectively. Ethyl benzene and cumene are starting materials for the production of phenol and styrene (*Catalysis Review* 2002, 44(3), 375). However, economic, engineering and environmental factors have driven the development of new technologies in which solid acids, such as zeolite-based catalysts, are used to catalyze the direct alkylation of benzene with propylene or ethylene. Several commercial processes have been developed in the past few years for the alkylation of aromatics with light alkenes based on zeolite catalysts. A common concern in these processes is that for more highly reactive olefins (reactivity increases with increasing length of the olefin chain) oligomerization of the olefin will compete with alkylation of the aromatic, and thus high aromatic to olefin ratios are needed. Furthermore, because monoalkyl-aromatics are more reactive that non-alkylated aromatics (due to the electron donating effects of the alkyl substituent), mono-alkyl aromatics are more readily alkylated to dialkyl or trialkyl-aromatics. However, such concerns are not relevant for the production of fuels, because the oligomerization and alkylation of aromatics can be done in one step, thereby saving capital costs.

Renewable benzene, toluene and xylene can be alkylated with renewable propylene or isobutylene to produce heavier aromatics compounds that are more suitable for renewable jet fuel (*Ind. Eng. Chem. Res.* 2008, 47, 1828). Furthermore, aromatic alkylation conditions are similar to oligomerization conditions and both steps can be performed in one reactor or one reaction zone by reacting a stream of $C_6$-$C_8$ aromatics with alkenes in the presence of a suitable catalyst, as shown in FIG. 1. Under excess olefin conditions, both aromatic alkylation and oligomerization will take place. Alternatively, it is well known that alcohols can also act as alkylating agents under acid catalytic conditions. Accordingly, in other embodiments, aromatics can be alkylated with alcohols under excess alcohol conditions (i.e. dehydration of the alcohol and subsequent oligomerization occur in the presence of aromatics, resulting in alkylation of aromatics). In still other embodiments, oligomerization/aromatic alkylation using $C_3$-$C_4$ olefins can be carried in the presence of an acid catalyst in one reaction zone or in one reactor having two or more reaction zones. In particular embodiments, $C_3$-$C_4$ alcohols can be used as alkylating agents for aromatics, in the presence of an acid catalyst, in one reaction zone.

The renewable jet fuel produced by the process of the present invention can be used directly as a jet fuel or blended with jet fuel derived from petroleum for use in jet engines. Renewable jet fuels include jet fuels comprising from about 0.01% to about 100% of hydrocarbons (aliphatic and aromatic) prepared from renewable feedstocks as described herein. In other embodiments, the jet fuels of the present invention comprise an amount of renewable hydrocarbons (aromatic and aliphatic of at least about 1%, 5%, 10%, 15%, 20%, 25%, 30%, 35%, 40%, 45%, 50%, 55%, 60%, 65%, 70%, 75%, 80%, 85%, 90%, 95%, or 100% inclusive of all values and subranges therebetween. Because the jet fuel described herein is renewable, it has a distinct carbon isotopic signature which can be used to identify its presence in blends. The renewable jet fuel derived from this process will contain measurable amounts of $^{14}C$ due to its origin from plant material whereas petroleum-based jet fuel contains essentially none. The increase in $^{14}C$ will be measurable in blends of any concentration of renewable jet fuel with petroleum-based jet fuel. Additionally, the biological pathways used to produce the $C_3$-$C_5$ alcohol starting materials react at different rates with molecules containing different carbon isotopes. The accumulation of these different reaction rates results in a difference in $^{13}C$ in the renewable product relative to an internationally recognized standard. The renewable jet fuel described herein will have a distinctive isotopic signature dependent upon which alcohols are used to produce it. Traces of the isotopic signature will be apparent in blends of renewable jet fuel with petroleum-based jet fuel. A discussion of how isotope effects accumulate in renewable materials and examples of composition of matter patents that use these effects are J. Agric. Food Chem. 1997, 45, p. 2042-2046; J. Agric. Food Chem. 2005, 53, p. 197-201; New Phytologist, 2004, 161, p. 371-385; Naturwissenschaften 2003, 90, p. 537-552; U.S. Pat. No. 7,169,588 B2; and U.S. Patent Application No. US 2007/0202062 A1.

In addition, the biofuel compositions of the present invention (e.g., gasoline, jet or diesel) are also quite different from petroleum-derived fuel compositions. The chemical conversion of a relatively pure renewable alcohol (e.g., isobutanol produced by fermentation) or a simple mixture of two or more renewable alcohols by dehydration, oligomerization, isomerization, hydrogenation, and optionally aromatization typically provides a characteristic mixture of branched dimers, trimers, tetramers, etc., whereas petroleum-derived fuels are distillates and/or blends of complex hydrocarbon mixtures. For example, as shown in FIGS. 3-7, conventional petroleum-based fuel compositions comprise a complex mixture of hydrocarbons produced by combining various distillation "cuts", whereas the biofuel compositions of the present invention comprise a much simpler mixture of hydrocarbons. An additional advantage to using renewable fuels of this invention is the ability to tune the final fuel properties by controlling the amount and types of oligomers that are produced. In traditional petroleum-based fuel refining such tuning is impractical because all carbon from crude oil must be utilized, limiting flexibility. For example, the cold flow properties of a renewable diesel fuel of this invention can be increased by changing the catalyst in the oligomerization step to one that favors slightly more branched products.

The process of the present invention may be carried out in batch, sequential batch (i.e. a series of batch reactors) or in continuous mode in any of the equipment customarily employed for continuous processes (see, for example, H. S. Fogler, Elementary Chemical Reaction Engineering, Prentice-Hall, Inc., NJ, USA). Byproducts such as the condensate water formed as the product of the dehydration reaction, hydrogen produced by an aromatization reaction, etc. can be removed by separation methods customarily employed for such separations.

In some embodiments, the alcohol produced by fermentation of an appropriate renewable feedstock is renewable isobutanol, which is dehydrated over an acid catalyst in a first reaction zone to form isobutylene. The isobutylene is oligomerized in a second reaction zone under suitable conditions (high heat) to provide primarily dimers, trimers, or tetramers (e.g. depending upon whether the desire product is gasoline, jet fuel, or diesel, or additives for any of these fuels). The oligomerized diisobutylene is then hydrogenated in a third reaction zone to provide the corresponding branched, saturated hydrocarbons (e.g., 2,2,4-trimethylpentane, 2,2,4,4,6-pentamethylheptane, and 2,2,4,4,6,6,8-heptamethylnonane, and isomers thereof). The "crude" product of the process comprises a mixture of $C_8$, $C_{12}$, and $C_1$-6 hydrocarbons, in which the predominant component is either one or more $C_8$ isomers, one or more $C_{12}$ isomers, or one or more $C_{16}$ isomers, depending upon the reaction conditions employed. In other embodiments, the dehydration and oligomerization steps can be carried out in a single reaction zone to form unsaturated oligomers (e.g., dimers, trimers, and tetramers) directly from isobutanol. In still other embodiments, the dehydration, oligomerization, and hydrogenation steps can be carried out in a single reaction zone to form branch, saturated hydrocarbons as described above directly from isobutanol.

In alternative embodiments, the alcohol produced by fermentation of an appropriate renewable feedstock is renewable isobutanol, which is dehydrated over an acid catalyst in a 1st reaction zone to form isobutylene. The isobutylene is recovered and reacted under high heat and pressure conditions in a second reaction zone containing one or more catalysts known to aromatize aliphatic hydrocarbons. The resulting aromatic product, comprising p-xylene, is recovered and optionally shown by known methods to be renewable. In another embodiment, the isobutanol is dehydrated and dimerized over an acid catalyst, and the diisobutylene is recovered and reacted in a second reactor to form renewable p-xylene. In yet another embodiment, isobutanol containing up to 15% water is dehydrated, or alternatively dehydrated and oligomerized, and then further reacted as described herein to form a renewable aromatic product comprising p-xylene. In another embodiment, hydrogen and the $C_1$-$C_3$ hydrocarbon byproducts of an aromatization reaction as described herein are recovered for later use in other reactions. In still other embodiments, the dehydration and aromatization step occurs in a single reaction zone using a single catalyst. The aromatic compounds are either purified to obtain pure streams of individual aromatic products or the mixture of aromatics is partially purified or used directly as an aromatic blendstock for gasoline or jet fuel.

In other embodiments, the alcohol produced by fermentation of an appropriate renewable feedstock is renewable 1-propanol or 2-propanol, which is dehydrated or dehydrated and oligomerized over an acid catalyst and then reacted over a second catalyst to produce benzene, toluene, and xylenes in addition to hydrogen and $C_1$-$C_2$ hydrocarbons. In yet other embodiments, the renewable alcohols are $C_4$ alcohols such as 1-butanol and 2-butanol, $C_5$ alcohols such as 2-methyl-1-butanol, isopentanol and 2-pentanol, or $C_6$ alcohols such as 2-methyl-1-pentanol, isohexanol and 2-hexanol that are dehydrated or dehydrated and oligomerized and then reacted over a second catalyst to produce xylenes and other alkyl- and dialkyl-benzenes in addition to hydrogen and $C_1$-$C_3$ hydrocarbons. In an embodiment, aromatization of these alcohols is performed in a single reaction zone. In yet another embodiment, the alcohols contain up to saturating levels of water. The aromatic compounds are either purified to obtain pure streams of individual aromatic products, or the mixture of aromatics is partially purified or used directly as a aromatic blendstock for jet fuel.

In other embodiments, mixtures of $C_2$-$C_{10}$ alcohols and/or $C_2$-$C_{20}$ hydrocarbons produced by the thermochemical processing of biomass are treated over appropriate catalysts to form renewable aromatic compounds and hydrogen and $C_1$-$C_3$ hydrocarbons. The aromatic compounds are either purified to obtain pure streams of individual aromatic products or the mixture of aromatics is partially purified or used directly as a aromatic blendstock for gasoline or jet fuel.

The materials produced by the processes described above are tested for their renewable carbon content using the test method described in ASTM D6866. The alcohols are primarily produced by the fermentation of recently harvested biomass (within the last 2 years). Therefore, the ratio of carbon isotopes of the recently produced product is approximately equal to the ratio of carbon isotopes of the current biomass. Older biomass is also used to produce these materials and will have carbon isotope ratios greater than zero which demonstrate that they are also renewable.

The methods of the present invention also provide compositions of aromatic compounds, especially benzene, toluene, alkylbenzenes, xylenes, and dialkylbenzenes. Using ASTM method D6866, the carbon content of these materials is shown to be renewable. It is the intent of this disclosure to cover all proportions of these renewable materials in blends with their fossil fuel carbon derived equivalents, as these blends have biobased carbon fractions when measured with ASTM method D6866.

In another embodiment, isobutanol produced by a biocatalyst from biomass can be directly used as a gasoline replacement. In other embodiments, however, isobutanol produced in this manner is reacted as described herein to provide a mixture of hydrocarbons which may also contain other organic compounds such as ethers and esters that can be used as diesel fuel. Other alcohols, for example, n-butanol and isoamyl alcohol derived from biomass (e.g. by fermentation), can be similarly treated to produce different hydrocarbon mixtures that also meet diesel fuel specifications. These mixtures may also contain ethers and esters derived from the starting alcohols. In general, the types of molecules suitable for use as a diesel fuel, e.g. linear and mono-branched alkanes, fatty acid esters, and ethers, have high cetane numbers.

In one embodiment, diesel fuel is produced from renewable isobutanol in the following manner: 1) isobutanol produced by a biocatalyst from biomass-derived feedstocks is removed from the fermentation broth by distillation or other means (e.g., extraction from the fermentor headspace under reduced pressure); 2) isobutanol of sufficient purity is transferred to a reactor containing a heterogenous catalyst that catalyzes the dehydration of isobutanol to form isobutylene, and one or more of the condensation of one or more isobutylene units into a larger hydrocarbon (e.g. oligomerization), the rearrangement of the isobutylene monomers during condensation (or the rearrangement of oligomerized hydrocarbons), and the reaction of alkene bonds in the hydrocarbon product with hydrogen (e.g. hydrogenation), methanol, or carbon dioxide. The reactor containing isobutanol and the catalyst described in (2) is maintained at an operating temperature and pressure that promotes the reactions required to convert the isobutanol into a diesel fuel, and the hydrocarbon or organic compound mixture obtained after step (and 2) is removed from the reactor and treated to remove impurities. The hydrocarbon or organic compound mixture or biofuel is tested against ASTM diesel fuel specifications, and if it does not meet specifications it is blended with other biofuel components to produce material that will pass specifications. Similarly, renewable jet fuel can be prepared by a similar method, except that the hydrocarbons prepared in step (2) on average have a lower molecular weight and are more volatile than the hydrocarbons appropriate for renewable diesel fuel, and meet ASTM specifications for jet fuel (in which case the mixture may be used directly as jet fuel, or if not, are blended with a jet fuel or jet fuel precursor to meet the appropriate ASTM specification). Likewise, renewable gasoline (including aviation gasoline) can be prepared by similar method, except that the hydrocarbons prepared in step (2) have a lower molecular weight and are more volatile than the hydrocarbons for renewable jet fuel, and meet ASTM specifications for gasoline (in which case the mixture may be used directly as gasoline, or if not, blended with gasoline or a gasoline precursor to meet the appropriate ASTM specification).

In certain embodiments, and additional aromatization step can be incorporated into the process (as described herein) to provide biofuels (e.g., gasoline, aviation gasoline, diesel, or jet fuels) which additionally include an aromatic component.

In a particular embodiment, jet fuel is produced in the following manner: 1) isobutanol produced by fermentation of a biomass-derived feedstock is removed from the fermentation broth by distillation or other means; 2) isobutanol of sufficient quality is transferred to a reaction zone containing a catalyst that catalyzes the dehydration of isobutanol to form isobutylene; 3) the isobutylene is oligomerized in a reaction zone to form a mixture of unsaturated aliphatic hydrocarbons suitable for jet fuel (e.g., primarily $C_{12}$ hydrocarbons); 4) isobutylene is reacted in a reaction zone to form aromatic compounds, especially p-xylene, and hydrogen gas; 5) hydrogen gas is separated from the aromatic products and used to convert the oligomers formed in step (3) to saturated hydrocarbons; 6) the aliphatic and aromatic hydrocarbons are blended to a product that meets all jet fuel specifications; and optionally 7) if the biofuel does not meet jet fuel specifications it is blended with other biofuel or petroleum based components to produce a mixture that meets jet fuel specifications. Alternatively, off-specification renewable jet fuel can be used as diesel fuel or blended with any diesel fuel.

In several embodiments, the process described herein produces other types of hydrocarbon mixtures including various different grades of diesel fuel including diesel fuel for trucks, trains, and ships. In other words, any hydrocarbon mixture that can be used as a fuel can be produced from renewable alcohols by the methods described.

As described above, isobutanol is a particular embodiment of the renewable alcohol starting materials used in the process of the present invention. However, any $C_2$-$C_6$ alcohol formed from biomass suitable for use in the process of the present invention. For example ethanol can be dehydrated to form ethylene, separately or in situ, and then oligomerized to form linear hydrocarbons of various lengths. Alpha-olefins of varying size, i.e. $C_4$ to greater than $C_{20}$ are produced in this manner. If completely unbranched alkanes are desired to use directly as diesel fuel or to blend with other hydrocarbons to produce diesel fuel, the products, i.e. alk-1-enes, of the alpha-olefin process are reduced with hydrogen to form saturated linear alkanes sized $C_4$ to greater than $C_{20}$. The oligomerization of ethylene to form these compounds usually requires an organometallic aluminum catalyst, but zeolite-catalyzed oligomerization has also been reported (see *Accounts of Chemical Research* 2005, 38, 784-793; *Journal of Natural Gas Chemistry* 2002, 11, 79-86; U.S. Pat. No. 4,025,575; WO 2005/092821 A1).

As discussed herein, in most embodiments of the process of the present invention, a renewable alcohol (or mixture of renewable alcohols) derived from biomass, for example by fermentation, are dehydrated to form alkenes which are then converted to biofuels or fine chemicals through one or more subsequent processing steps. The renewable alcohol may be dehydrated by feeding an aqueous solution of the alcohol (or mixture of alcohols) into a reactor containing e.g. an acidic solid phase catalyst, which is heated to convert the alcohol into an alkene, e.g. isobutylene. In another embodiment, the alkene is captured after the dehydration step, separated from the water, and fed into a separate oligomerization reactor. In still another embodiment, the alkene is formed in situ in the reactor and continues to react in other ways with the catalyst in the reactor to form oligomers that are precursors to, or are biofuels. In yet another embodiment, a mixture of renewable alcohols is fed into a dehydration reactor to form a mixture of alkenes that are further oligomerized to precursors to, or to biofuels in the same reactor, or a second reactor in the process. The oligomerization products are reduced to saturated hydrocarbons by hydrogen, wherein the hydrogen may be produced by the aromatization of a second stream of renewable alcohol or alkene. These aromatics are optionally blended with the saturated hydrocarbons to produce biofuels, e.g. jet fuel, that meet ASTM specifications.

In one embodiment of the invention described herein, a biofuel precursor, e.g. isobutanol, formed by the fermentation of a biomass-derived feedstock is dehydrated in a chemical reactor that contains a solid phase catalyst that catalyzes both the dehydration, oligomerization, and partial rearrangement of the alcohol to form precursors to, or form biofuels (e.g. jet or diesel fuels) with increased isomer diversity, relative to a biofuel formed by oligomerization without rearrangement. The resulting alkenes are also reduced by the solid phase catalyst in the presence of hydrogen to form saturated hydrocarbon biofuels (e.g. jet or diesel fuels). In order to obtain a fully renewable biofuel, the hydrogen used for the hydrogenation is derived from biofuel precursors (e.g. alkenes) that are reacted over an aromatization catalyst to form aromatics for blending into the biofuel, for example jet fuel. In another embodiment, a linear biofuel precursor, e.g. n-butanol, formed by the fermentation of a biomass-derived feedstock is dehydrated in a chemical reactor that contains a solid phase catalyst that catalyzes both the dehydration, oligomerization, and rearrangement of the alcohol to form precursors to, or form biofuels with increased branching and isomer diversity, relative to a biofuel formed by oligomerization without rearrangement, that are also reduced by the solid phase catalyst in the presence of renewable or non-renewable hydrogen to form saturated hydrocarbon biofuels, e.g. jet or diesel fuels. In some embodiments, the biofuel precursor to (e.g. alcohol) is fed to the dehydration/oligomerization/rearrangement reactor as an aqueous solution. In yet another embodiment, the biofuel precursor (e.g. alcohol) is converted into an alkene in a first reactor, then the alkene is fed into a second, separate reactor where it is oligomerized and rearranged to form precursors to, or forms biofuels (e.g. jet or diesel fuels) with increased branching and isomer diversity, relative to a biofuel formed by oligomerization without rearrangement, that are reduced by another solid phase catalyst in the presence of renewable or non-renewable hydrogen in a third reactor to form saturated hydrocarbon biofuels, e.g. jet or diesel fuels.

In a particular embodiment, the biofuel produced by the dehydration of renewable isobutanol (e.g., produced by fermentation), and subsequent oligomerization, rearrangement, and reduction (e.g., hydrogenation) is a jet fuel comprising a distribution of hydrogenated oligomers of butylenes in which a majority of the oligomers are isomers of butylene trimers containing 12 carbon atoms. In other particular embodiments, this composition is blended with aromatics produced from renewable alcohols (e.g., the same renewable alcohols used to prepare the hydrogenated butylene oligomers).

The resulting mixture of alkanes and aromatics that is the final jet fuel product is not soluble in water. Any water that passes through the system, either as part of an aqueous alcohol mixture used to feed the dehydration reactor, or which is removed from the alcohol during the dehydration process, is separated from the final product by phase separation. Alternatively, if a separate dehydration reactor is used, water is separated from the alkene product stream by a similar method. By tuning the catalyst composition and reactor conditions it is possible to produce a mixture of hydrocarbons that meets jet fuel specifications, wherein the primary purification of the product steam comprises removal of water and trace contaminants that interfere with its use as a fuel (e.g. by phase separation). Alternatively, additional purification may be carried out to refine the mixture of hydrocarbons into a biofuel meeting ASTM specifications (e.g. gasoline, diesel, or jet fuel specifications).

In some embodiments, the product stream will comprise a mixture of hydrocarbons which can be separated into different fractions, each of which corresponds to a particular type of fuel, such that the majority or all of the product stream can be distilled into two or three fractions corresponding to e.g. jet fuel and other fuels such as gasoline or diesel fuel. Any remaining organic material, primarily polymeric material, can be used for other purposes such as lubricants, tars, or oils. In other embodiments, the product stream will comprise a mixture of hydrocarbons that can be distilled to produce one or more of a jet fuel, #1 grade diesel fuel, and #2 grade diesel fuel. For example, the product stream comprises a mixture of hydrocarbons that are distilled into a jet fuel and #1 grade diesel fuel; or the product stream is distilled into a jet fuel and #2 grade diesel fuel; or the product stream is distilled into #1 grade diesel fuel and #2 grade diesel fuel; or the product stream is distilled into #1 grade diesel fuel, #2 grade diesel fuel, and jet fuel.

In still other embodiments after distilling the product stream into separate product streams comprising one or more of a jet fuel, #1 grade diesel fuel, #2 grade diesel fuel, the residual portion of the product stream comprises hydrocarbons which are blended into fuel precursors so that the resulting blends meet all ASTM specifications for the respective fuel. For example, the residual hydrocarbon components remaining after distillation of one or more of a jet fuel, #1 grade diesel fuel, and/or #2 grade diesel fuel can be purified and used for other purposes, such as using residual 2,2,4-trimethylpentane as an octane enhancer for gasoline and an additive for gasoline replacement.

In particular embodiments, a renewable jet fuel of the present invention comprises at least one of the following eight-carbon and twelve-carbon compounds: renewable 2,2,4-trimethylpentane, renewable 2,2,4,4,6-pentamethylheptane, renewable 2-methylpentane, renewable 2,4-dimethylheptane, renewable 2,4,6-trimethylnonane and renewable xylene. In another particular embodiment, the jet fuel comprises at least two of those compounds. In another embodiment, the combined concentration of these compounds in the renewable jet fuel of the present invention is at least about 10%, at least about 50%, or at least about 100% greater than their concentration in petroleum-derived, non-renewable jet fuel.

In particular embodiments, a renewable diesel fuel comprises one or more of 2,2,4-trimethylpentane, 2,2,4,4,6-pentamethylheptane, 2,2,4,4,6,6,8-heptamethylnonane, 2,2,4,4,6,6,8,8,10-nonamethylundecane, and 2,2,4,4,6,6,8,8,10,10,12-undecamethyltridecane. In other particular embodiments, the renewable diesel fuel comprises oligomers that have been rearranged, such as 2,2,4-trimethylpentane, 2,2,4,4,6-pentamethylheptane, 2,2,4,4,6,6,8-heptamethylnonane, 2,2,4,4,6,6,8,8,10-nonamethylundecane, and 2,2,4,4,6,6,8,8,10,10,12-undecamethyltridecane and various isomers and other derivatives of these compounds including, but not limited to, 2,3,4-trimethylpentane, 2,3,4,4,5-pentamethylheptane, 2,3,3,4,5,6-pentamethylheptane, and 2,2,3,4,6,6,7,8,10-nonamethylundecane. In yet another embodiment, these organic compounds are present in concentrations such that the entire mixture is a diesel fuel that meets ASTM D975 specifications for diesel fuel as determined by ASTM methods D93, D86, D445, D613, D1319 and D130.

In most embodiments, the biofuels or biofuel precursors of the present invention comprise about 100% of renewable aliphatic hydrocarbons (e.g., renewable $C_8$-$C_{24}$ branched aliphatic hydrocarbons) and optionally aromatic hydrocarbons (e.g., renewable BTX) prepared by the processes described herein. In other embodiments, the biofuels of the present invention comprise a blend of renewable hydrocarbons (aliphatic and/or aromatic) and non-renewable compounds (e.g., petroleum-derived hydrocarbons, additives, etc.). In some embodiments, the biofuels or biofuel precursors of the present invention comprise at least about 1% of renewable $C_8$-$C_{24}$ branched aliphatic hydrocarbons, or about 2%, about 5%, about 10%, about 15%, about 20%, about 30%, about 40%, about 50%, about 60%, about 70%, about 80%, about 90%, about 95%, or about 99% of renewable $C_8$-$C_{24}$ branched aliphatic hydrocarbons.

In yet another embodiment, the biofuel precursors are a mixture of alcohols that are ethanol, propanols, butanols, and pentanols. The mixture is oligomerized with rearrangement to form a complex product mixture of branched and unbranched hydrocarbons and other organic compounds that are present in concentrations such that the entire mixture is a diesel fuel that meets ASTM D975 specifications for diesel fuel as determined by ASTM methods D93, D86, D445, D613, D1319 and D130. These embodiments are only exemplary since many different combinations of alcohol biofuel precursors and degrees of rearrangement are possible to create mixtures of branched and unbranched hydrocarbons and organic compounds that are present in these mixtures in concentrations such that these mixtures are diesel fuel that meets ASTM D975 specifications for diesel fuel as determined by ASTM methods D93, D86, D445, D613, D1319 and D130.

In still other embodiments, the biofuel precursors are propanols, and the hydrocarbon and organic compound mixture produced comprises 2-methylpentane, 2,4-dimethylheptane, 2,4,6-trimethylnonane, 2,4,6,8-tetramethylundecane, 2,4,6,8,10-pentamethyltridecane, 2,4,6,8,10,12-hexamethylpentadecane, and 2,4,6,8,10,12,14-heptamethylheptadecane and isomers and other derivatives of these compounds in concentrations such that the entire mixture is a jet fuel that also meets ASTM D975 specifications for diesel fuel as determined by ASTM methods D93, D86, D445, D613, D1319 and D130. In yet another embodiment, the biofuel precursors are pentanols and the hydrocarbon and organic compound mixture produced comprises 1,3-diisopropylbutane, 1,3,5-triisopropylhexane, 1,3,5,7-tetraisopropyloctane, and 1,3,5,7,9-pentaisopropyldecane and isomers and other derivatives of these compounds in concentrations such that the entire mixture is a jet fuel that also meets ASTM D975 specifications for diesel fuel as determined by ASTM methods D93, D86, D445, D613, D1319 and D130.

As discussed above, many fine chemicals such as acrylates or phthalates are conventionally prepared from petroleum-based starting materials. Renewable alcohols can also serve as starting materials for preparing renewable fine chemicals. For example, acrolein or methacrolein can be prepared by oxidizing propylene and isobutylene, alkanes such as isobutane, and alcohols such as t-butanol or isobutanol by partial oxidation over a suitable catalyst. Some processes generate acrolein or methacrolein in the first step, which is then oxidized to acrylic acid or methacrylic acid in a second step, and converted into a methyl ester—the monomeric unit for polymerization—in a third step. (U.S. Pat. Nos. 3,301,906, 3,825,502, 3,755,458, 4,129,600, 4,190,608, 4,354,044). Alternatively, such compounds can be prepared in a two step process in which the appropriate alkene is oxidized to acrolein or methacrolein and then methyl acrylate or methyl methacrylate is prepared by oxidative esterification (U.S. Pat. No. 5,969,178). Generally, the same reaction conditions can be used to prepare alkacroleins and alkacrylates (e.g., wherein the "alk" moiety refers to an alkyl radical such as methyl, ethyl, etc.) from higher molecular weight alkenes and alcohols. For example, 2-methyl-1-butene and 2-methyl-1-butanol reacted under these conditions to provide ethacrolein and ethacrylates. Thus, in some embodiments, renewable acrylates such as renewable acrolein, methacrolein, ethacrolein, acrylic acid, methacrylic acid, ethacrylic acid, acrylic asters, methacrylic esters, and ethacrylic esters can be prepared by the oxidation of the appropriate renewable alcohol, renewable alkene (e.g. prepared from the corresponding renewable alcohol by dehydration, or by a combination of dehydration, and oligomerization), or renewable alkane (e.g. prepared from the corresponding renewable alkene by hydrogenation), optionally in the presence of alcohol (renewable or non-renewable alcohols) if an ester is the desired product. In other embodiments, the alkalcroleins or alkacrylates can be prepared by direct oxidation of appropriate renewable alcohols prepared e.g., by fermentation of biomass as described herein. One advantage of direct oxidation of alcohols is that the dehydration of the alcohol on the oxidation catalyst provides steam to regenerate the catalyst during operation, increasing catalyst lifetime and allowing the reactor to operate longer without interruption to regenerate.

As indicated above, aromatic fine chemicals are conventionally prepared from aromatic starting materials distilled from, or derived from petroleum. As discussed herein, renewable aromatic compounds can also be prepared from renewable alcohols, for example by aromatization of alkenes or alkanes prepared by dehydration or dehydration and hydrogenation of renewable alcohols. Alternatively, renewable aromatic compounds can be obtained by alkylation of renewable aromatic compounds with renewable alkenes, and other processes described herein.

In one embodiment, a renewable alcohol, e.g. isobutanol, is dehydrated over an acidic catalyst in a reactor to form isobutylene. The isobutylene is recovered and reacted under the appropriate high heat and pressure conditions in a second reactor containing a catalyst known to aromatize aliphatic hydrocarbons, as described herein. The renewable p-xylene is recovered and may be shown to be renewable by ASTM methods referenced herein. In another embodiment, the renewable alcohol, e.g. isobutanol is dehydrated and dimerized over an acid catalyst; the resulting diisobutylene is recovered and reacted in a second reactor to form renewable p-xylene. In yet another embodiment, a renewable alcohol, e.g. isobutanol containing up to 15% water is dehydrated, or dehydrated and oligomerized, and the resulting oligomers aromatized to form renewable p-xylene. In still another embodiment, hydrogen and $C_1$-$C_3$ hydrocarbon byproducts of the aromatization reaction are recovered for later use in other reactions. In yet another embodiment, the dehydration of the renewable alcohol and the aromatization of the resulting alkene occurs in a single reactor using a single catalyst, to form a mixture of renewable aromatic compounds. The resulting renewable aromatic compounds are purified, e.g. by distillation or crystallization to obtain pure streams of individual renewable aromatic products. The pure xylenes from these reactions are oxidized to their corresponding phthalic acids and phthalate esters using the methods described herein.

In other embodiments, the alcohol is renewable 1-propanol or 2-propanol, which is dehydrated or dehydrated and oligomerized over an acid catalyst and then reacted over a second catalyst to produce benzene, toluene, and xylenes in addition to hydrogen and $C_1$-$C_3$ hydrocarbons. In yet other embodiments, the renewable alcohols are $C_4$ alcohols such as 1-butanol and 2-butanol, $C_5$ alcohols such as isopentanol and 2-pentanol, or $C_6$ alcohols such as isohexanol and 2-hexanol, that are dehydrated, or dehydrated and oligomerized, and then reacted over a second catalyst to produce xylenes and other alkyl- and dialkyl-benzenes in addition to hydrogen and $C_1$-$C_3$ hydrocarbons. In still another embodiment, the aromatization of the renewable alcohols described above is carried out in a single reactor. In yet another embodiment, the renewable alcohols contain up to saturating levels of water, and the resulting renewable aromatic compounds are purified to obtain pure streams of individual renewable aromatic products. The pure xylenes from these reactions are then oxidized to their corresponding phthalic acids and phthalate esters using the methods described herein.

In other embodiments, mixtures of $C_2$-$C_{10}$ alcohols and/or $C_2$-$C_{20}$ hydrocarbons produced by the thermochemical processing of biomass are treated over appropriate catalysts to form renewable aromatic compounds and hydrogen and $C_1$-$C_3$ hydrocarbons. The renewable aromatic compounds are purified to obtain pure streams of individual renewable aromatic products. The pure xylenes from these reactions are oxidized to their corresponding phthalic acids and phthalate esters using the methods described above.

EXAMPLES

Example 1

Isobutanol Fermentation

An overnight culture was started in a 250 mL Erlenmeyer flask with microorganism from a freezer stock (e.g., *Escherichia coli* modified to produce isobutanol) with a 40 mL volume of modified M9 medium consisting of 85 g/L glucose, 20 g/L yeast extract, 20 μM ferric citrate, 5.72 mg/L $H_3BO_3$, 3.62 mg/L $MnCl_2.4H_2O$, 0.444 mg/L $ZnSO_4.7H_2O$, 0.78 mg/L $Na_2MnO_4.2H_2O$, 0.158 mg/L $CuSO_4.5H_2O$, 0.0988 mg/L $CoCl_2.6H_2O$, 6.0 g/L $NaHPO_4$, 3.0 g/L $KH_2PO_4$, 0.5 g/L NaCl, 2.0 g/L $NH_4Cl$, 0.0444 g/L $MgSO_4$, and 0.00481 g/L $CaCl_2$ and at a culture $OD_{600}$ of 0.02 to 0.05. The starter culture was grown for approximately 14 hrs in a 30° C. shaker at 250 rpm. Some of the starter culture was then transferred to a 400 mL DasGip fermentor vessel containing about 200 mL of modified M9 medium to achieve an initial culture $OD_{600}$ of about 0.1. The vessel was attached to a computer control system to monitor and control the fermentation to a pH of 6.5 (by appropriate addition of base), a temperature of 30° C., dissolved oxygen levels, and agitation. The vessel was agitated, with a minimum agitation of 200 rpm—the agitation was varied to maintain a dissolved oxygen content of about 50% of saturation using a 12 sl/h air sparge until the $OD_{600}$ was about 1.0. The vessel was then induced with 0.1 mM IPTG. After continuing growth for approximately 8-10 hrs, the dissolved oxygen content was decreased to 5% of saturation with 200 rpm minimum agitation and 2.5 sl/h airflow. Continuous measurement of the fermentor vessel off-gas by GC-MS analysis was performed for oxygen, isobutanol, ethanol, carbon dioxide, and nitrogen throughout the experiment. Samples were aseptically removed from the fermentor vessel throughout the fermentation and used to measure $OD_{600}$, glucose concentration, and isobutanol concentration in the broth. Isobutanol production reached a maximum at around 21.5 hrs with a titer of 18 g/L and a yield of approximately 70% maximum theoretical. The broth was subjected to vacuum distillation to provide a 84:16 isobutanol/water mixture which was redistilled as needed to provide dry isobutanol.

Example 2

Isobutanol Dehydration 23 g of a commercial γ-alumina catalyst was loaded into a fixed-bed tubular reactor. Wet isobutanol containing about 12% water was fed through a preheater and onto the catalyst bed. The internal reactor temperature was maintained at 310° C., and the WHSV of the isobutanol was ~6 hr$^{-1}$. Isobutylene and water containing about <1% of unreacted isobutanol were recovered. The products were separated in a gas-liquid separator and the isobutylene recovered. The conversion was >99%, and GC-MS analysis of the gas phase effluent indicated it was >90% isobutylene with the remainder comprising linear butenes.

Example 3

Isobutanol Dehydration 20 mL of wet isobutanol containing 15% water was reacted in a batch reactor over 2 gm of Zeolite-Y CBV-780 at 220° C. The reactor pressure increased from atmospheric pressure to 350 psig. Conversion of isobutanol was about 25% and GC-MS analysis indicated the product mixture was >90% isobutylene and <10% linear butenes.

Example 4

Isobutanol/Gasoline Blend

Isobutanol was blended with 84.7 octane gasoline with a Reid vapor pressure (RVP) of 8.47 psi to a concentration of 12.5% v/v isobutanol/gasoline. The RVP of the blend was 8.14 psi and the octane number was 86.9.

Example 5 n-Butanol/Gasoline Blend

N-butanol is blended with 84.7 octane gasoline with a Reid vapor pressure of 8.47 psi to a concentration of 12.5% v/v n-butanol/gasoline. The RVP of the blend is 8.14 psi and the octane number is 85.0.

Example 6

Pentanol/Gasoline Blend

Pentanols produced by a fermentation process similar to that described in Example 1 (except that a microorganism preferentially producing pentanols instead of isobutanol was used) are separated from the fermentation broth by distillation. The pentanols are blended with 84.7 octane gasoline with a Reid vapor pressure of 8.47 psi to a concentration of 12.5% v/v pentanols/gasoline. The resulting blend is tested and shown to meet ASTM specifications for gasoline. The RVP of the blend is 8.0 psi and the octane number is 85.0.

Example 7

Isobutanol/Gasoline Blend

Isobutanol prepared by a fermentation process e.g., of Example 1 was blended with 84.7 octane gasoline with a Reid vapor pressure of 8.47 psi to a concentration of 16.1% v/v isobutanol/gasoline. The RVP of the blend was 7.98 psi and the octane number was 87.7.

Example 8

Thermochemical Synthesis of $C_1$-$C_7$ Alcohols

Poplar wood chips are heated for 8 hours in a gasifier at 500° C. over a solid catalyst comprising cobalt and sodium to produce a mixture of alcohols including methanol, ethanol, propanols, butanols, pentanols, hexanols, and heptanols. The butanols and pentanols are separated from the mixture by distillation and are blended with 84 octane gasoline with a vapor pressure of 15 psi at 100° F. to a concentration of 20% v/v alcohols in gasoline. The resulting blend is tested and shown to meet ASTM specifications for gasoline. The vapor pressure of the blend is 12.5 psi at 100° F. and the octane number is 84.6. Using ASTM method D6866 it is determined that the blend is renewable. A life cycle analysis of the production of the blend is performed to show that burning a gallon of the blend produces less than 19 pounds of net carbon dioxide. The cost of producing a gallon of the blend is shown to be equivalent to the cost of a gallon of unblended gasoline.

Example 9

Diisobutylene from Isobutanol in an Integrated Flow Reactor

Isobutanol produced by fermentation (e.g. according to Example 1) was separated from the fermentation broth by distillation. The isobutanol, which contains 16% water, was passed through a chemical reactor containing a commercial γ-alumina catalyst heated to 310° C. at ~10 psig and a WHSV of 6 hr$^{1}$. The water drained from the bottom of the reactor contained less than 0.1 M isobutanol, and isobutylene (gas) was collected with >99% conversion. The isobutylene gas was dried by passing it through molecular sieves, and was then fed into a second reactor containing a ZSM-5 catalyst maintained at 140-160° C., ambient pressure, and WHSV=1.5 hr$^{-1}$ to give ~60% conversion to a mixture of about 80% of diisobutylene isomers and about 20% triisobutylene isomers and minor quantities of higher molecular weight products.

Example 10

Isododecane from Isobutanol in an Integrated Flow Reactor

Isobutanol produced by fermentation (e.g. according to Example 1) was separated from the fermentation broth by distillation. The isobutanol, which contains 16% water, was passed through a chemical reactor containing acidic commercial γ-alumina catalyst heated to 310° C. at ~10 psig and a WHSV of 6 hr$^{-1}$. The water drained from the bottom of the reactor contained less than 0.1 M isobutanol, and isobutylene (gas) was collected with >99% conversion. The isobutylene gas was dried by passing it through molecular sieves, and was then fed into a second reactor containing Amberlyst® 35, maintained at 100-120° C., ambient pressure, and WHSV=2.5 hr$^{-1}$ to give ~90% conversion to a mixture of about 15% of diisobutylene isomers, 75% triisobutylene isomers and 10% tetramers. The liquid product was pumped to a trickle-bed hydrogenation reactor packed with a commercial 0.5% Pd on alumina catalyst and co-fed with 10% excess hydrogen. Hydrogenation of >99% of the olefins occurred at 150° C., 150 psig, and WHSV=3 hr$^{-1}$. The saturated hydrocarbon product was collected with an overall process yield of ~90%.

Example 11

Gasoline from Dimers and Trimers of Isobutylene

The product mixture from Example 9 was fed into a hydrogenation reactor containing a 0.5% Pd on alumina catalyst maintained at 150° C. and 150 psi to give a saturated hydrocarbon product, which was distilled at atmospheric pressure to give three fractions containing diisobutylene, triisobutylene and small quantities of higher molecular weight products. The three fractions can be separated and used in aviation gasoline and auto gasoline.

Example 12

Methylundecene Isomers from Isobutylene 90 g of isobutylene, as formed in Example 2, was loaded into a 350 mL batch reactor with 10 g of a ZSM-5 catalyst (Si:Al ratio=80) that had been treated with 2,4,6-trimethylpyridine. The sealed reactor was heated to 220° C. and allowed to react for approximately 40 hours. 75 mL of product was collected and a sample was analyzed by GC/MS. The composition was approximately 30% $C_{12}$ or larger molecules and the primary compounds were isomers of methylundecene.

Example 13

Methylundecene Isomers to Diesel Fuel

The unsaturated product from Example 12 was loaded into a 350 mL batch reactor containing 1 g of 5% Pd/C catalyst. The reactor was flushed with nitrogen and pressurized with 200 psig of hydrogen. The reactor was heated to 100° C. and held at this temperature for 1 hour. 70 mL of product was collected and analyzed by GC/MS. The product was found to be fully saturated. 70 mL of this hydrogenated mixture was then distilled to concentrate the $C_{12}+$ fraction (i.e., the fraction containing $C_{12}$ or higher hydrocarbons). Approximately 50 mL of the mixture was distilled off (primarily $C_8$ hydrocarbons), leaving 20 mL of $C_{12}+$ hydrocarbons. The flash point of the final product was measured as 51° C. and the derived cetane number was measured by ASTM D6890-07 as 68. The product was determined to meet the ASTM specifications for #1 diesel fuel.

Example 14

Diesel Fuel Blend Composition

The renewable #1 diesel fuel from Example 13 is blended in a 50:50 mixture with #2 diesel fuel having a flash point of 62° C. and a cetane number of 44. The resulting blend is tested and shown to meet ASTM D975-07 specifications for #2 diesel fuel. The flash point of the blend is 55° C. and the derived cetane number is 56 using ASTM method D6890-07. It is determined that the blend is renewable (i.e., meets the requirements of ASTM method D6866).

Example 15

Jet Fuel from Isobutylene

The trimerization of isobutylene (e.g., isobutylene prepared as described in Examples 1 or 2) was carried out using a fixed bed continuous flow system equipped with a tube furnace housing SS 316 reactor (OD 5/16 in×12 in), gas flow meters, an HPLC pump, a back pressure regulator, and a gas-liquid separator. In a typical trimerization procedure, the reactor was loaded with β Zeolite CP 814C (Zeolyst International) and isobutylene was fed at WHSV 1-3 $h^{-1}$ at a reaction temperature of 140-180° C., at atmospheric pressure. The isobutylene conversion was 85% with a product distribution of about 29% dimer isomers, 58% trimer isomers, and 11% tetramer isomers. The hydrogenation of the resulting oligomer blend was carried out at 150° C. and 150 psi $H_2$ to give a hydrocarbon product which was fractionated to provide a blend of saturated $C_{12}$ (trimers) and $C_{16}$ (tetramers) hydrocarbons that were used as a jet fuel feedstock.

Example 16

Additives in a Jet Fuel Composition

To the diesel fuel produced in Example 15, dinonylnaphthylsulfonic acid is added to enhance static charge dissipation, and 10% of petrochemically-derived C10+ aromatics are added to improve seal performance in older jet turbine engines. The resulting fuel composition, when tested using ASTM methods D56, D86, D1298, D7154, D445, D4809, D1322, D1840, D1319, D3241, D381, D3242, and D130 is shown to meet the requirements for jet fuel.

Example 17

Xylene from Diisobutylene

Diisobutylene prepared from isobutanol as described in Example 9 was fed to a reactor containing a chromium doped eta-alumina catalyst. The reactor was maintained at 550° C. with a WHSV of 1.1 $hr^{-1}$. The reaction product was condensed and analyzed by GC-MS. The yield of the xylene fraction was about 20%, and p-xylene was produced with a selectivity of 90%. Hydrogen, methane, ethane, ethylene, propane, isobutylene, n-butane, isobutylene, and 2-butene were also produced and captured for use in other processes.

Example 18

BTEX from Isobutylene

A fixed bed continuous flow system equipped with a tube furnace housing SS 316 reactor (OD 5/16 in×12 in), gas flow meters, an HPLC pump, back pressure regulator, and a gas-liquid separator was loaded with ZSM-5 CBV 8014 Zeolite catalyst. The catalyst was calcined at 540° C. under $N_2$ for 8 hrs before the reaction was started. Isobutylene (e.g., prepared as described herein) was fed into the reactor at WHSV 1.0 $h^{-1}$ and the reaction conditions were maintained at 400-550° C. and atmospheric pressure. Aromatic products were formed in about 45% yield and the selectivity for BTEX (i.e., benzene, toluene, ethylbenzene and xylene) was 80%. The aromatic product was separated and used in fuels and other products.

Example 19

BTEX from Isobutylene

A fixed bed continuous flow system equipped with a tube furnace housing SS 316 reactor (OD 5/16 in×12 in), gas flow meters, an HPLC pump, back pressure regulator, and a gas-liquid separator was loaded with ZSM-5 CBV 5524 G Zeolite catalyst. The catalyst was calcined at 540° C. under $N_2$ for 8 his before the reaction was started. Isobutylene (e.g., prepared as described herein) was fed into the reactor at WHSV 1.0 $hr^{-1}$ while the reaction conditions were maintained at 400-550° C. and atmospheric pressure. Aromatic products were formed in about 35% yield and the selectivity for BTEX was 80%. The aromatic product was separated and used in fuels and other products.

Example 20

BTEX from Isobutylene

A fixed bed continuous flow system equipped with a tube furnace housing SS 316 reactor (OD 5/16 in×12 in), gas flow meters, an HPLC pump, back pressure regulator, and a gas-liquid separator was loaded with type YCBV 870 Zeolite catalyst. The catalyst was calcined at 540° C. under $N_2$ for 8 hrs before the reaction was started. Isobutylene (e.g., prepared as described herein) was fed at WHSV $1.0 \, h^{-1}$ while the reaction conditions were maintained at 400-550° C. and atmospheric pressure. Aromatic products were formed in about 25% yield and the selectivity for BTEX was 80%. The aromatic product was separated and used in fuels and other products.

Example 21

Dehydration of Propanol

Propanols produced by fermentation (e.g., similar to the method of Example 1, except that the microorganisms preferentially produce propanols rather than isobutanol) are separated from the fermentation broth by distillation. 23 g of a commercial γ-alumina catalyst is loaded into a fixed-bed tubular reactor. Propanol is fed through a preheater and onto the catalyst bed. The internal reactor temperature is maintained at 350° C., and the WHSV of the propanol is ~6 $hr^{-1}$. Propylene and water are recovered, and the water contains about 7% of unreacted propanol. The propylene and water are separated in a gas-liquid separator and the propylene is recovered. The conversion is about 90%, and GC-MS analysis of the gas phase effluent indicated it is >90% propylene.

Example 22

Diesel Fuel from Propylene 90 g of propylene, prepared as described in Example 21, is loaded into a 350 mL batch reactor containing 10 g of a ZSM-5 catalyst (Si:Al ratio=80) that is been treated with 2,4,6-trimethylpyridine. The sealed batch reactor is heated to 220° C. and allowed to react for approximately 40 hours. 75 mL of product is collected and a sample is analyzed by GC/MS. The composition is approximately 30% $C_{12}$ or larger molecules and the primary compounds are isomers of methylundecene. The product is then loaded into a 350 mL batch reactor with 1 g of 0.5% Pd/C catalyst. The reactor is flushed with nitrogen and pressurized with 200 psig of hydrogen and heated to 100° C. and held at that temperature for 1 hour, with stirring. 70 mL of product is collected and analyzed by GC/MS. The product is found to be fully saturated. 70 mL of this hydrogenated mixture is then distilled, to concentrate the $C_{12}$+ fraction. Approximately 50 mL of the mixture is distilled off (primarily $C_9$ compounds), leaving 20 mL of $C_{12}$+ hydrocarbons. The flash point of the final product is measured as 51° C. and the derived cetane number is measured as 68. The product is determined to meet the ASTM specifications for #1 diesel fuel.

Example 23

Mixed Butenes from 1-Butanol

1-Butanol produced by fermentation (e.g., similar to the method of Example 1, except that the microorganisms preferentially produce 1-butanol rather than isobutanol) is separated from the fermentation broth by distillation. 23 g of a commercial γ-alumina catalyst is loaded into a fixed-bed tubular reactor. 1-Butanol is fed through a preheater and onto the catalyst bed. The internal reactor temperature is maintained at 350° C. and the WHSV of the 1-butanol is ~6 $hr^{-1}$ Butylene isomers and water are recovered, and the water contains about 7% of unreacted 1-butanol. The products are separated in a gas-liquid separator and the butylene is recovered. The conversion is about 98%, and GC-MS analysis of the gas phase effluent indicated it is >90% butylene isomers.

Example 24

Diesel Fuel from Butylene 90 g of butylene, prepared as described in Example 23, was loaded into a 350 mL batch reactor with 10 g of a ZSM-5 catalyst (Si:Al ratio=80) that had been treated with 2,4,6-trimethylpyridine. The sealed batch reactor was heated to 220° C. and allowed to react for approximately 40 hours. 75 mL of product was collected and a sample was analyzed by GC/MS. The composition was approximately 30% C12 or larger molecules (C16$^+$) and the primary compounds were isomers of methylundecene. The product was then loaded into a 350 mL batch reactor with 1 g of 0.5% Pd/C catalyst. The reactor was flushed with nitrogen and pressurized with 200 psig of hydrogen, then heated to 100° C. and held at that temperature for 1 hour. 70 mL of product was collected and analyzed by GC/MS. The product was found to be fully saturated. 70 mL of this hydrogenated mixture was then distilled to concentrate the C12+ fraction. Approximately 50 mL of the mixture was distilled off (primarily C8 compounds), leaving 20 mL of C12+ hydrocarbons. The flash point of the final product was measured as 51° C. and the derived cetane number was measured as 68. The fuel was determined to meet the ASTM specifications for #1 diesel fuel.

Example 25

BTEX from Butylene Isomers

A fixed bed continuous flow system equipped with a tube furnace housing SS 316 reactor (OD 5/16 in×12 in), gas flow meters, an HPLC pump, back pressure regulator, and a gas-liquid separator was loaded with ZSM-5 CBV 8014 Zeolite catalyst. The catalyst was calcined at 540° C. under $N_2$ for 8 hrs before the reaction was started. Butylene (e.g. prepared as described in Example 24) was fed at WHSV $1.0 \, h^{-1}$ while the reaction conditions were maintained at 400-550° C. and atmospheric pressure. Aromatic products were formed in about 40% yield and with a selectivity for BTEX of about 80%. The aromatic product was separated and used in fuels and other products.

Example 26

Jet Fuel from Propylene

The oligomerization of propylene (e.g., prepared as described in Example 21) is carried out using a fixed bed continuous flow system equipped with a tube furnace housing a SS 316 reactor (OD 5/16 in×12 in), gas flow meters, an HPLC pump, a back pressure regulator, and a gas-liquid separator. In a typical trimerization procedure, the reactor is loaded with β Zeolite CP 814C (Zeolyst International) and propylene is fed into the reactor at WHSV 1-3 hr$^{-1}$ while the reaction conditions are maintained at 140-180° C. and atmospheric pressure. The hydrogenation of the resulting blend of olefin oligomers is carried out at 150° C. and 150 psi $H_2$ to provide a mixture of saturated hydrocarbons which are subsequently fractionated to provide an isolated blend of about 20% dimers, 40% trimers and 40% tetramers (and trace amounts of higher oligomers) that are separated and used as a jet fuel feedstock.

Example 27

Additives for Jet Fuel Composition

To the biofuel produced in Example 26 dinonylnaphthylsulfonic acid is added to enhance static charge dissipation, and 10% of petrochemically-derived aromatics are added to improve seal performance in older jet turbine engines. This composition, when tested using ASTM methods D56, D86, D1298, D7154, D445, D4809, D1322, D1840, D1319, D3241, D381, D3242, and D130, meets the ASTM specifications for jet fuel.

Example 28

Additives for Jet Fuel Composition

Dinonylnaphthylsulfonic acid is added to the jet fuel prepared as described in Example 26 to enhance static charge dissipation and de-icing properties, but additional aromatic additives are not required because the fuel is compatible with newer, high-technology seal elastomers. This aviation biofuel composition exhibits a freezing point of −75° C. with no cloudiness until −59° C. according to test method ASTM D2386, and when tested using ASTM methods D56, D86, D1298, D445, D4809, D1322, D1840, D1319, D3241, D381, D3242, and D130, and meets the ASTM specifications for jet fuel.

Example 29

Diesel Fuel from Ethanol

Ethanol recovered from the fermentation of a carbohydrate feedstock or the thermochemical treatment of biomass is converted into ethylene by reacting it over an HZSM-5 acidic zeolite catalyst for 2 seconds at 350° C. in a tubular flow reactor. The ethylene that is produced is separated by flash distillation from the water by-product and passed through a reactor containing 0.01% (w/w ethylene) dichloroethylaluminum. Initially, the reaction temperature is about 30° C., but the reaction temperature increases as the exothermic reaction proceeds. A mixture of $C_6$ to $C_{20}$ α-olefins is produced from the reaction. These olefins are recovered and reduced with hydrogen over a platinum catalyst to form linear saturated hydrocarbons that are blended with other hydrocarbons to provide a composition meeting ASTM specifications for diesel fuel.

Example 30

BTEX from $C_1$ to $C_7$ Alcohols

Poplar wood chips are heated for 8 hours in a gasifier at 500° C. over a solid catalyst containing cobalt and sodium to produce a mixture of alcohols including methanol, ethanol, propanols, butanols, pentanols, hexanols, and heptanols. A fixed bed continuous flow system equipped with a tube furnace housing SS 316 reactor (OD 5/16 in×12 in), gas flow meters, an HPLC pump, a back pressure regulator, and a gas-liquid separator is loaded with ZSM-5 Zeolite catalyst. The catalyst is calcined at 540° C. under $N_2$ for 8 hrs before the reaction is started. The $C_1$ to $C_7$ alcohol mixture, above, is fed into the reactor at WHSV 1.0 h$^{-1}$ and the reaction conditions are maintained at 400-550° C. and atmospheric pressure. Aromatic products are formed in about 40% yield and with a selectivity for BTEX of about 80%. The aromatic product is separated and used in fuels and other products. The aromatics are tested using ASTM method D6866 and determined to be renewable. The aromatics are blended with gasoline and with jet fuel providing fuel blends which are also tested using ASTM method D6866 and shown to be renewable.

Example 31

Isopentene from Isopentanol

Isopentanol produced by a fermentation process similar to that described in Example 1 (except that a microorganism preferentially producing isopentanol instead of isobutanol was used) is separated from the fermentation broth by distillation. 23 g of a commercial γ-alumina catalyst is loaded into a fixed-bed tubular reactor and isopentanol is fed through a preheater and onto the catalyst bed. The internal reactor temperature is maintained at 350° C., and the WHSV of the isopentanol is ~6 hr$^{-1}$. Isopentene and water containing about 7% of unreacted isopentanol is recovered. The products are separated in a gas-liquid separator and the dehydrated isopentene is recovered. The conversion is about 98%, and GC-MS analysis of the gas phase effluent indicates it is >90% isopentene.

Example 32

Jet Fuel from Isopentene

The oligomerization of isopentene is carried out using a fixed bed continuous flow system equipped with a tube furnace housing a SS 316 reactor (OD 5/16 in×12 in), gas flow meters, an HPLC pump, a back pressure regulator, and a gas-liquid separator. In a typical trimerization procedure, the reactor is loaded with β Zeolite CP 814C (Zeolyst International) and isopentene is fed into the reactor at WHSV 1-3 h$^{-1}$ while the reaction conditions are maintained at 100-150° C. and ambient pressure. The conversion is about 85%, with a product distribution of about 15% isopentene, 25% isopentene dimers, 50% isopentene trimers, and 10% isopentene tetramers. The hydrogenation of this oligomer blend is carried out at 150° C. and 150 psi $H_2$ to give a saturated hydrocarbon product which is fractionated to provide isolated $C_{15}$ isomers that are used as a jet fuel feedstock.

Example 33

Diesel Fuel from Isopentene 90 g of isopentene, prepared as described in Example 31, is loaded into a 350 mL batch reactor with 10 g of a ZSM-5 catalyst (Si:Al ratio=80) that is treated with 2,4,6-trimethyl pyridine. The sealed batch reactor is heated to 220° C. and the reaction is allowed to proceed for approximately 40 hours. 75 mL of product is collected and a sample is analyzed by GC/MS. The product composition is approximately 30% $C_{10}$ or larger molecules and the primary compounds are isomers of methyltetradecene. The product is loaded into a 350 mL batch reactor with 1 g of 0.5% Pd/C catalyst, the reactor is flushed with nitrogen and then pressurized with 200 psig of hydrogen and stirred. The reactor is heated to 100° C. and held at that temperature for 1 hour. 70 mL of product is collected and analyzed by GC/MS. The product is found to be fully saturated. 70 mL of this hydrogenated mixture is then distilled, to concentrate the $C_{15}+$ fraction. Approximately 50 mL of the mixture is distilled off (primarily $C_{10}$ compounds), leaving 20 mL of $C_{15}+$ hydrocarbons. The flash point of the final product is measured as 54-56° C., and the derived cetane number is 68. The final product was determined to meet the ASTM specification for #2 diesel fuel.

Example 34

Dimers and Trimers of Isopentene from Isopentanol

Isopentanol produced by a fermentation process similar to that described in Example 1 (except that a microorganism preferentially producing isopentanol instead of isobutanol was used) is separated from the fermentation broth by distillation. The isopentanol, which contains 5% water, is passed through a chemical reactor containing gamma alumina heated to 350° C. at 1 atmosphere. Water is drained from the bottom of the reactor and isopentene is collected with 98% conversion. The isopentene gas is dried by passing it through molecular sieves and is then fed into a second reactor containing a ZSM-5 catalyst at 160° C. and 100 psi pressure to give a mixture of about 80% of pentene dimers and about 20% of pentene trimers and minor quantities of higher molecular weight products at 80% conversion.

Example 35

Gasoline from Dimers of Isopentene

The product mixture from Example 34 is charged into a hydrogenation reactor with a 0.5% Pt on alumina catalyst, and which is maintained at 150° C. and 150 psi hydrogen to give a saturated hydrocarbon product, which was distilled at atmospheric pressure to give three fractions containing $C_{10}$ isomers, $C_{15}$ isomers, and small amounts of $C_{20}$ isomers and traces of higher molecular weight products, respectively. The fractions are separated and blended in gasoline.

Example 36

BTEX from Isopentene

A fixed bed continuous flow system equipped with a tube furnace housing SS 316 reactor (OD 5/16 in×12 in), gas flow meters, an HPLC pump, a back pressure regulator, and a gas-liquid separator is loaded with ZSM-5 CBV 8014 Zeolite catalyst. The catalyst is calcined at 540° C. under $N_2$ for 8 hrs before the reaction is started. Isopentene (e.g., as prepared in Example 31) is fed into the reactor at WHSV $1.0\,h^{-1}$ while the reactor conditions are maintained at 400-550° C. and atmospheric pressure. Aromatic products are formed in about 40% yield and with a selectivity for BTEX of about 80%. The aromatic product is separated and used in fuels and other products.

Example 37

Experimental Jet Fuels

Renewable jet fuels are produced from biofuel precursors such as isobutanol by reacting the precursors in chemical reactor(s), as described above, containing a catalyst that converts the precursors into mixtures of hydrocarbons. The resulting fuel product meets the specifications for jet fuel.

If the biofuel precursor is isobutanol, then the renewable jet fuel composition will comprise branched $C_8$, $C_{12}$ and $C_{16}$ hydrocarbons. In this example, experimental jet fuel blends were prepared with only $C_8$, $C_{12}$ and $C_{16}$ hydrocarbons to better understand the impact of chemical composition on key physical properties. Various experimental jet fuel blends and the physical properties of these blends are provided below in Table 1.

TABLE 1

Experimental Jet Fuel Blends and Physical Properties

| | Matrix | | | | Blend Composition vol % | | | | | | Physical Properties | | | |
|---|---|---|---|---|---|---|---|---|---|---|---|---|---|---|
| | Aromatics | $C_8$ | i-paraffin | | | | | | | | Flash Point | Freezing Point | Smoke Point | Density (Kg/L) at |
| Blend | vol % | vol % | vol % | p-xylene | n-$C_8$ | i-$C_8$ | n-$C_{12}$ | i-$C_{12}$ | n-$C_{16}$ | i-$C_{16}$ | (° C.) Min 38 | (° C.) Max −40 | (mm) Min 25 | 15.6° C. 775-840 |
| 1 | 5 | 10 | 95 | 5.0 | 0.5 | 9.0 | 3.8 | 72.2 | 0.5 | 9.0 | 26 | −58.0 | 32 | 755 |
| 2 | 5 | 10 | 75 | 5.0 | 2.4 | 7.1 | 19.0 | 57.0 | 2.4 | 7.1 | 28 | −36.5 | 33 | 753 |
| 3 | 5 | 2 | 95 | 5.0 | 0.1 | 1.8 | 4.1 | 78.6 | 0.5 | 9.8 | 38 | −58.5 | 32 | 758 |
| 4 | 5 | 2 | 75 | 5.0 | 0.5 | 1.4 | 20.7 | 62.1 | 2.6 | 7.8 | 38 | −36.0 | 33 | 757 |
| 5 | 10 | 10 | 95 | 10.0 | 0.5 | 8.6 | 3.6 | 68.4 | 0.5 | 8.6 | 26 | −58.0 | 24 | 765 |
| 6 | 10 | 10 | 75 | 10.0 | 2.3 | 6.8 | 18.0 | 54.0 | 2.3 | 6.8 | 28 | −38.5 | 30 | 756 |
| 7 | 10 | 2 | 95 | 10.0 | 0.1 | 1.7 | 3.9 | 74.5 | 0.5 | 9.3 | 36 | −56.0 | 28 | 763 |
| 8 | 10 | 2 | 75 | 10.0 | 0.5 | 1.4 | 19.6 | 58.8 | 2.5 | 7.4 | 38 | −38.0 | 30 | 763 |
| 9 | 15 | 10 | 95 | 15.0 | 0.4 | 8.1 | 3.4 | 64.6 | 0.4 | 8.1 | 26 | −58.5 | 24 | 765 |
| 10 | 15 | 10 | 75 | 15.0 | 2.1 | 6.4 | 17.0 | 51.0 | 2.1 | 6.4 | 28 | −38.0 | 23 | 765 |
| 11 | 15 | 2 | 95 | 15.0 | 0.1 | 1.6 | 3.7 | 70.3 | 0.5 | 8.8 | 34 | −54.5 | 22 | 776 |
| 12 | 15 | 2 | 75 | 15.0 | 0.4 | 1.3 | 18.5 | 55.5 | 2.3 | 6.9 | 36 | −38.0 | 24 | 768 |

Example 38

Isooctene from Isobutylene/SPA Catalyst

A fixed bed continuous flow reactor was loaded with solid phosphoric acid (SPA) catalyst. The SPA catalyst was prepared according to published procedures (Ind. Eng. Chem. Res. 2007, 46, 7838-7843) and was calcined at 320° C. and was sieved to obtain 2-3 mm particles. Isobutylene was fed into the reactor at a WHSV between 1.0-1.3 with reaction conditions maintained at 160-180° C. and atmospheric pressure. The isobutylene was converted to liquid oligomers at about 90% yield and the selectivity for isooctene isomers was 82%. The isooctene isomers were separated from heavier oligomers by fractionation at atmospheric pressure. The isooctene isomers were hydrogenated to isooctane as described in the hydrogenation step in Example 23. The octane value R+M/2 of the hydrogenated isooctane was 98, the vapor pressure RVP was 1.65 psig, and the freezing point was below −55° C.

Example 39

Isooctene from Isobutylene/Zeolite ZSM-5 Catalyst

A fixed bed continuous flow reactor was loaded with ZSM-5 CBV 2314 Zeolite catalyst. Prior to reaction, the catalyst was calcined at 540° C. under $N_2$ for 8 hrs. Isobutylene was fed into the reactor at a WHSV between 1.2-2 $h^{-1}$ and the reaction conditions were maintained at 160-180° C. and atmospheric pressure. The isobutylene was converted to liquid oligomers at about 85% yield, and the selectivity for isooctene isomers was 88%. The isooctene isomers were separated from heavier oligomers by atmospheric fractionation. The isooctene isomers were hydrogenated to isooctane as described in the hydrogenation step in Example 23. The octane value R+M/2 of the hydrogenated isooctane was 98, vapor pressure RVP was 1.65 psig, and freezing point was below −55° C.

Example 40

Isooctene from Isobutylene/Amberlyst-15 Catalyst 3 grams of dry Amberlyst 15 catalyst was charged into a 300 mL stainless steel batch reactor. Isobutylene (33 g) and a similar amount of isobutane diluent were also charged into the reactor. The mixture was stirred for two hours, the temperature was increased to 140° C., and the pressure was increased to 580 psi. The conversion, based on the amount of isobutylene starting material, was 85% and the selectivity to isooctene isomers was 62%. The isooctene isomers were separated from heavier oligomers by atmospheric fractionation. The isooctene isomers were hydrogenated to isooctane as described in the hydrogenation step in Example 23. The octane value R+M/2 of the hydrogenated isooctane was 98, vapor pressure RVP was 1.65 psig, and freezing point was below −55° C.

Example 41

Isooctene from 1-Butene/Zeolite ZSM-5 Catalyst

A fixed bed continuous flow reactor was loaded with ZSM-5 CBV 2314 Zeolite catalyst. Prior to starting the reaction, the catalyst was calcined at 540° C. under $N_2$ for 8 hrs. 1-butene was fed into the reactor at a WHSV between 0.2-2.0 $h^{-1}$ while the reaction conditions were maintained at 200-240° C. and atmospheric pressure. The 1-butene was converted to liquid oligomers at about 80% yield and with a selectivity for $C_4$-$C_9$ isomers of 90%. 1-butene did not oligomerize at the temperatures at which isobutylene isomers oligomerized, so the relatively high oligomerization temperature range of 200-240° C. produced all of the possible $C_4$-$C_9$ olefin isomers, probably due to cracking. Some of the oligomers produced were $C_6$-$C_8$ hydrocarbons having low levels of branching, and thus had low octane values.

Example 42

Isooctene Hydrogenation 2 grams of 0.5% Palladium on carbon (0.5% Pd/C) catalyst was charged into a 2000 mL stainless steel batch reactor equipped with stirrer. 1000 mL of a hydrocarbon fraction comprising isooctene isomers was charged into the reactor. The reactor was then flushed with nitrogen and pressurized with 100 psig hydrogen. The reaction mixture was stirred for one hour and the temperature was increased from ambient temperature to 80-100° C. The reactor was subsequently cooled down to ambient temperature and excess hydrogen remaining in the reactor was released, and the reactor purged with a small amount of nitrogen. The product was filtered off from the catalyst and GC analysis of the product showed 100% hydrogenation.

Example 43

Isooctene Alkylate

Oligomerization of more than 95% pure isobutylene with only 5% of other $C_4$ isomers (cis and trans 2-butene) over either solid phosphoric acid (SPA) or zeolite ZSM-5 catalysts produced high quality high octane isooctene isomers. The olefinic product was hydrogenated with hydrogen in the presence of 0.5% Pd/C and gave 100% paraffinic isooctane referred to as "alkylate". The alkylate produced by this technique comprises more than 97% of highly branched isooctane isomers, including 2,2,4-trimethylpentane (R+M/2=100), 2,3,4-trimethylpentane (R+M/2=98.3), 2,2,3-trimethylpentane (R+M/2=104.9), and 2,3,3-trimethylpentane (R+M/2=103). This type of selective oligomerization and the absence of $C_3$ and $C_5$ hydrocarbons in the composition provides an alkylate with superior properties (e.g., octane values) compared to the analogous petroleum refinery alkylate. The minimum octane value of the alkylate provided by oligomerization of a $C_4$ olefinic feed is 98, while the average octane value of typical petroleum refinery alkylate is 92-94, and this refinery alkylate contains considerable amounts of $C_6$, $C_7$, and $C_9$ isomers.

Example 44

BTEX and Hydrogen from Isobutylene Aromatization

A fixed bed continuous flow reactor was loaded with ZSM-5 CBV 8014 Zeolite catalyst. Prior to initiating the reaction, the catalyst was calcined at 540° C. under $N_2$ for 8 hrs. Isobutylene was fed into the reactor at a WHSV of 1.0 $h^{-1}$ while the reaction conditions were maintained at 400-550° C. and atmospheric pressure. Aromatic products were formed in about 45% yield with a selectivity for BTEX of 80%. The aromatic products were isolated and used in fuels and other products. Hydrogen also was produced as a byproduct of the reaction; about 3 moles of hydrogen were produced for each mole of aromatic ring formed.

Example 45

BTEX and Hydrogen from Isobutylene Aromatization

A fixed bed continuous flow reactor was loaded with ZSM-5 CBV 5524 G zeolite catalyst. Prior to initiating the reaction, the catalyst was calcined at 540° C. under $N_2$ for 8 hrs. Isobutylene was fed into the reactor at a WHSV of $1.0\,h^{-1}$ while the reaction conditions were maintained at 400-550° C. and atmospheric pressure. Aromatic products were formed in about 40% yield with a selectivity for BTEX of 80%. The aromatic products were isolated and used in fuels and other products. Hydrogen also was produced as a byproduct of the reaction; about 3 moles of hydrogen were produced for each mole of aromatic ring formed.

Example 46

BTEX and Hydrogen from Isobutylene Aromatization

A fixed bed continuous flow reactor was loaded with Zeolite type Y CBV 780 catalyst. Prior to initiating the reaction, the catalyst was calcined at 540° C. under $N_2$ for 8 hrs. Isobutylene was fed into the reactor at a WHSV of $1.0\,h^{-1}$ while the reaction conditions were maintained at 400-550° C. and atmospheric pressure. Aromatic products were formed in about 25% yield and with a selectivity for BTEX of 80%. The aromatic products were isolated and used in fuels and other products. Hydrogen also was produced as a byproduct of the reaction; about 3 moles of hydrogen were produced for each mole of aromatic ring formed.

Example 47

BTEX and Hydrogen from Diisobutylene Aromatization

A fixed bed continuous flow reactor was loaded with ZSM-5 CBV 8014 Zeolite catalyst. Prior to initiating the reaction, the catalyst was calcined at 540° C. under $N_2$ for 8 hrs. Isobutylene was fed into the reactor at a WHSV of $1.6\,h^{-1}$ while the reaction conditions were maintained at 400-550° C. and atmospheric pressure. Aromatic products were formed in about 38% yield and with a selectivity for BTEX of 80%. The aromatic products were isolated and used in fuels and other products. Hydrogen also was produced as a byproduct of the reaction; about 3 moles of hydrogen were produced for each mole of aromatic ring formed.

Example 48

Aviation Gasoline

Aviation gasoline (Avgas) blend was prepared by blending hydrocarbons comprising 90% renewable hydrocarbons. The Avgas blend was formulated mainly from isooctane, toluene, isobutylene, and isopentane or isomerate blend. Toluene obtained from a BTEX aromatic blend and was used in the Avgas formulation. To meet the Avgas ASTM D-910 standard, the Avgas was formulated from 70-80% alkylate, 10-20% toluene, 1-3% isobutylene, and 10% of a petroleum isomerate stream or isopentane. The motor octane number (MON) value for a lean mixture was higher than 100 as required for standard Avgas grades 100LL and 100. The sulfur content was 1-10 ppm—substantially below the 500 ppm maximum standard of ASTM D-910. All other specifications such as freezing point, oxidation stability of this Avgas met or exceeded the requirements of the D-910.

Example 49

Auto Gasoline

Several formulated auto gasolines (gasoline(s)) were prepared from a blend of 90% renewable and 10% petroleum hydrocarbons. The gasoline blends were formulated mainly from isooctane, isooctene, BTEX, isobutylene, and isopentane or isomerate blends. Benzene from BTEX was fractionated and removed and it was used for the production of higher molecular weight aromatic molecules (e.g., by alkylation of aromatics as described herein). Gasoline blends were formulated from 50-80% isooctane, 0-10% isooctene, 1-3% isobutylene, 10-20% BTEX, and only 10% of petroleum isomerate blend or isopentane. Because the octane values R+M/2 of isooctane and isooctene are above 98, and the BTEX R+M/2 is above 100, the octane value of the gasoline produced thereby was more than 100, the sulfur content was only 1-10 ppm, the benzene level was less than 0.5% and the amount of aromatics was below about 20%. This formulated gasoline meets all of the requirements of ASTM 4814 (including the RVP value), and is expected to meet gasoline standards for 2010 and beyond.

Example 50

Jet Fuel from Isobutylene Over Zeolite

The trimerization of isobutylene was carried out using a fixed bed continuous flow system equipped with a tube furnace housing SS 316 reactor (OD 5/16 in×12 in), gas flow meters, an HPLC pump, a back pressure regulator, and a gas-liquid separator. In a typical trimerization procedure the reactor was loaded with β Zeolite CP 814C (Zeolyst International) and isobutylene was fed into the reactor at a WHSV of $1\text{-}3\,h^{-1}$ while the reaction conditions were maintained at 140-180° C. and atmospheric pressure. The isobutylene conversion was about 85% with a product distribution of about 29% isobutylene dimer isomers, about 58% of isobutylene trimer isomers, and about 11% of isobutylene tetramer isomers. The hydrogenation of the resulting oligomer blend was carried out over a 0.5% Pd/Alumina catalyst at 150° C. and 150 psi $H_2$ to give a mixture which was fractionated to isolate a blend of isobutylene trimers and isobutylene tetramers that were used as a jet fuel feedstock.

Example 51

Jet Fuel from Isobutylene over Amberlyst® 35

The trimerization of isobutylene was carried out using a fixed bed continuous flow system equipped with a tube furnace housing SS 316 reactor (OD 5/16 in×12 in), gas flow meters, an HPLC pump, a back pressure regulator, and a gas-liquid separator. In a typical trimerization procedure the reactor was loaded with Amberlyst® 35 (Rohm and Haas) and isobutylene was fed into the reactor at a WHSV of $1\text{-}3\,h^{-1}$ while the reaction temperature was maintained at 120-140° C. by removing the heat from the exothermic reaction using a water bath to cool the reactor. The reaction was carried out at atmospheric pressure. The isobutylene conversion was 95% with product distribution of about 20% isobutylene dimer isomers, about 70% of isobutylene trimer isomers and about 10% of isobutylene tetramer isomers. The hydrogenation of the resulting oligomer blend was carried out over a 0.5% Pd/Alumina catalyst at 150° C. and 150 psi $H_2$ to give a mixture which was fractionated to isolate a blend of isobutylene trimers and isobutylene tetramers that were used as a jet fuel feedstock.

The properties of the jet fuel feedstock produced from isobutylene over an Amberlyst® 35 catalyst, and blends with t-butylbenzene and Jet A-1 was compared to the jet fuel specifications of ASTM D1655. As shown in the Table 2, the jet fuel feedstock itself meets or exceeds all ASTM D1655 specifications except for the density and API gravity (the low density is due to the lack of aromatic compounds). Blends with 12 vol % t-butylbenzene show that the addition of one type of aromatic compound will bring the density and API gravity parameters within the ASTM specification. In addition, the jet fuel feedstock can be blended up to 58 vol. % with conventional petroleum derived Jet A-1.

TABLE 2

Comparison of Example 51 Jet Fuel Feedstock/Blends with ASTM D 1655

| Property | ASTM method | Jet A or Jet A-1 ASTM D 1655 | Renewable Jet Fuel Feedstock | Renewable jet Fuel Feedstock plus 12 v % t-Butylbenzene | Renewable Jet Fuel Feedstock plus 42 v % Jet A-1 |
|---|---|---|---|---|---|
| Appearance | | | | | |
| Visual appearance | visual | | Clear, bright and visually free from solid matter and undissolved water at ambient temperature | Clear, bright and visually free from solid matter and undissolved water at ambient temperature | Clear, bright and visually free from solid matter and undissolved water at ambient temperature |
| Saybolt Color | D156 | report | +30 | | |
| Composition | | | | | |
| 1. Aromatics, vol % | D1319 | 25 max | <1 | 13 | 8.4 |
| Olefins, vol % | D1319 | | <1 | 2 | 1 |
| Sulfur, total mass % | D1266 | 0.30 max | 0.01 | 0.02 | 0.01 |
| Volatility | | | | | |
| Distillation Temperature, ° C. | D86 | | | | |
| IBP | | | 168 | 172 | 177 |
| 10% recovered | | 205 max | 178 | 178 | 185 |
| 20% recovered | | | 181 | 180 | 188 |
| 50% recovered | | report | 190 | 186 | 195 |
| 90% recovered | | report | 250 | 244 | 238 |
| FBP | | 300 max | 305 | 290 | 284 |
| Distillation residue, % | | 1.5 max | 0.5 | 1 | 1 |
| Distillation loss, % | | 1.5 max | 0.5 | 0.5 | 0.5 |
| Flash Point, ° C. | D3828 | 38 min | 49 | 48 | 50 |
| Density at 15° C., kg/L | D1298 | 0.775-0.840 | 0.768 | 0.782 | 0.778 |
| API gravity at 60, ° F. | D1298 | | 53 | 49 | 50 |
| Fluidity | | | | | |
| Freezing Point, ° C. | D2386 | 40 for Jet A 47 for Jet A-1 | −80 | −80 | −70 |
| Viscosity at −20° C., cSt | D445 | 8 max | 7 | 6 | 5 |
| Combustion | | | | | |
| Net heat of combustion, MJ/kg | D3338, | 42.8 min | 43.9 | 42.6 | 43.1 |
| Hydrogen content, mass % | D3343 | | 15.08 | 14.30 | 14.51 |
| Smoke point, mm or | D1322, | 25 min | 28 | 28 | 28 |
| Smoke point, mm and naphthalene, vol % | | | | | |
| | D1322, D1840 | 18 min, 3.0 max | | | |
| Corrosion | | | | | |
| Copper strip, 2 h at 100° C | D130 | No 1 max | 1b | 1b | 1b |
| Thermal stability | | | | | |
| Filter pressure drop, mm Hg | D3241 | 25 max | 1 | 1 | 1 |
| tube visual rating | | 3 max | <1 | <1 | <1 |
| Contaminants | | | | | |
| Existing gums, mg/100 mL | D381 | 7 max | 2.5 | 3.2 | 4.2 |
| Water reaction interface rating | D1094 | | 1 b | | |

TABLE 2-continued

Comparison of Example 51 Jet Fuel Feedstock/Blends with ASTM D 1655

| Property | ASTM method | Jet A or Jet A-1 ASTM D 1655 | Renewable Jet Fuel Feedstock | Renewable jet Fuel Feedstock plus 12 v % t-Butylbenzene | Renewable Jet Fuel Feedstock plus 42 v % Jet A-1 |
|---|---|---|---|---|---|
| Water separation index, microseparometer rating | D3948 | 85 min (with EC additive) 70 min (without EC additive) | 98 | 98 | 98 |
| Lubricity (BOCLE) Wear scar diameter, mm | D5001 | | 0.850 | 0.825 | 0.800 |
| Electrical conductivity, pS/M | D2624 | 600 max | 2 | 3 | 3 |

Example 52

Integrated Oligomers Production

Isobutanol produced by fermentation (e.g., as described in Example 1) was separated from the fermentation broth by distillation. The isobutanol, which contains 16% water, was passed through a chemical reactor containing pelleted SPA catalyst heated to 350° C. at 1 atmosphere. Water was drained from the bottom of the reactor and isobutylene was collected with 99% conversion. The isobutylene gas was dried by passing it through molecular sieves, and was then fed into a second reactor containing Amberlyst® 35 (Rohm and Haas) catalyst maintained at 120-140° C. and ambient pressure to give 90% conversion to a mixture of about 27% of diisobutylene isomers and about 70% triisobutylene isomers, and minor quantities of higher molecular weight products.

Example 53

Integrated Saturated Oligomers Production

Isobutanol produced by fermentation was separated from the fermentation broth by distillation. The isobutanol, which contains 16% water, was passed through a chemical reactor containing pelleted SPA catalyst heated to 350° C. at 1 atmosphere. Water was drained from the bottom of the reactor and isobutylene was collected with 99% conversion. The isobutylene gas was dried by passing it through molecular sieves, and then fed into a second reactor containing Amberlyst® 35 (Rohm and Haas) catalyst maintained at 120-140° C. and ambient pressure to give 90% conversion to a mixture of about 27% of diisobutylene isomers and about 70% triisobutylene isomers and minor quantities of higher molecular weight products. This oligomers blend was then fed into a third reactor to hydrogenate the olefins over 0.5% Pd supported in alumina at 150° C. and 150 psi $H_2$. The resulting product was fractionated to isolate a blend of isobutylene trimers and tetramers that were used as a jet fuel feedstock.

Example 54

Benzene Alkylation with Isobutylene Over Beta Zeolite

Benzene was alkylated with isobutylene in batch-type reactor. The reactor was loaded with 1.25 g of Beta Zeolite CP 814E (Zeolyst International) and 55.5 mL (48.75 g) of benzene, sealed into the reactor, and the reactor was then purged with nitrogen. 11.4 g of isobutylene were then loaded into the reactor and the reactor was pressurized with $N_2$ to 500 psi. The reaction was carried out at 180° C. for 2 hours. The reactor was then cooled to room temperature, depressurized and the liquid product was analyzed by GC. t-Butylbenzene was produced in 38% yield.

Example 55

Hydrogenation Using $H_2$ from BTEX Process

The hydrogenation of an oligomer blend is carried out over a 0.5% Pd/Alumina catalyst at 150° C. with 150 psi of $H_2$ obtained from the BTEX process.

Example 58

Terephthalic Acid from Xylene

A round bottom flask equipped with a stirring mechanism, Dean-Stark trap, and outlet to a gas bubbler was charged with 0.024 mol p-xylene, 0.83 mol glacial acetic acid, 0.009 mol bromoacetic acid, and 0.021 mol cobalt acetate tetrahydrate. The contents were heated to reflux as oxygen at the rate of 20 g/h was passed through the mixture for 2 h. Water formed during the oxidation of p-xylene was collected in the Dean-Stark trap. After the reaction mixture was cooled to room temperature, terephthalic acid was filtered from solution, washed with fresh glacial acetic acid, and air dried. A yield of 75% terephthalic acid was obtained.

What is claimed is:

1. A process for preparing a renewable jet fuel comprising:
   (a) treating biomass to form a feedstock;
   (b) fermenting the feedstock with one or more species of microorganism, thereby forming one or more $C_2$-$C_6$ alcohols;
   (c) dehydrating at least a portion of the one or more $C_2$-$C_6$ alcohols obtained in step (b), thereby forming a product comprising one or more $C_2$-$C_6$ olefins;
   (d) isolating the one or more $C_2$-$C_6$ olefins;
   (e) oligomerizing at least a portion of the one or more $C_2$-$C_6$ olefins isolated in step (d), thereby forming a product comprising one or more $C_6$-$C_{24}$ unsaturated oligomers;
   (f) optionally hydrogenating at least a portion of the product of step (e) in the presence of hydrogen, thereby forming a product comprising one or more $C_6$-$C_{24}$ saturated alkanes; and
   (g) combining the product of step (f) with one or more $C_{10}$-$C_{14}$ aromatic hydrocarbons, thereby forming a jet fuel;
   whereby the product of step (g) meets the requirements of ASTM D1655.

2. The process of claim 1, wherein said dehydrating, oligomerizing, and hydrogenating are each carried out in the presence of a dehydration catalyst, oligomerization catalyst, and a hydrogenation catalyst, respectively.

3. The process of claim 2, wherein each of said dehydrating, oligomerizing, and hydrogenating are carried out in a different reaction zone.

4. The process of claim 2, wherein two or more of said dehydrating, oligomerizing, and hydrogenating are carried out in the same reaction zone.

5. The process of claim 2, wherein one or more of the dehydration catalyst, oligomerization catalyst, or hydrogenation catalyst are heterogeneous catalysts.

6. The process of claim 2, wherein one or more of the dehydration catalyst, oligomerization catalyst, or hydrogenation catalyst are homogeneous catalysts.

7. The process of claim 1, wherein said dehydrating and/or said oligomerizing are carried out in the presence of an acidic catalyst, wherein the acidic catalyst for dehydrating and the acidic catalyst for oligomerizing is the same or different.

8. The process of claim 1, wherein said $C_{10}$-$C_{14}$ aromatic hydrocarbons are prepared by:
   (1) aromatizing one or more $C_2$-$C_6$ olefins, one or more dimers of $C_2$-$C_6$ olefins, and/or one or more trimers of $C_2$-$C_6$ olefins; and optionally
   (2) oligomerizing the product of step (1).

9. The process of claim 8, wherein the one or more $C_2$-$C_6$ olefins are obtained from step (d) and the dimers and trimers of $C_2$-$C_6$ olefins are obtained from step (e).

10. The process of claim 8, wherein at least a portion of the hydrogen used in step (f) is provided by hydrogen formed as a byproduct of step (1).

11. A renewable jet fuel prepared by the process of claim 1.

12. A renewable jet fuel prepared by the process of claim 8.

13. A renewable jet fuel prepared by the process of claim 10.

14. The process of claim 1, further comprising removing said $C_2$-$C_6$ alcohols from the feedstock before said dehydrating.

15. The process of claim 14, wherein said removing comprises carrying out said fermenting in step (b) below atmospheric pressure, whereby aqueous $C_2$-$C_6$ alcohol vapor is removed.

16. A process for preparing a renewable aromatic compound, comprising:
   (i) treating biomass to form a feedstock;
   (ii) fermenting the feedstock with one or more species of microorganism, thereby forming one or more $C_2$-$C_6$ alcohols;
   (iii) dehydrating at least a portion of the one or more $C_2$-$C_6$ alcohols obtained in step (ii), thereby forming a product comprising one or more $C_2$-$C_6$ olefins;
   (iv) isolating the one or more $C_2$-$C_6$ olefins;
   (v) optionally oligomerizing the one or more $C_2$-$C_6$ olefins to one or more dimers and/or one or more trimers of the $C_2$-$C_6$ olefins;
   (vi) aromatizing one or more $C_2$-$C_6$ olefins from step (iv) or one or more dimers and/or one or more trimers of the $C_2$-$C_6$ olefins of step (v), thereby forming a product comprising $C_6$-$C_{14}$ aromatic hydrocarbons, and hydrogen; and
   (vii) optionally oligomerizing the product of step (vi) in the presence of the one or more $C_2$-$C_6$ olefins of step (v) to form a product comprising one or more $C_8$-$C_{16}$ aromatic hydrocarbons.

17. A process of preparing renewable terephthalates, comprising preparing renewable p-xylene by the method of claim 16, wherein the product of step (vi) comprises at least 50% p-xylene, and further comprising:
   (a) optionally isolating and purifying the p-xylene of step (vi); and
   (b) oxidizing the p-xylene, optionally in the presence of one or more alcohols, thereby forming renewable terephthalates.

18. A renewable jet fuel or jet fuel precursor comprising a mixture of aromatic hydrocarbons and $C_{11}$-$C_{14}$ aliphatic hydrocarbons.

19. The renewable jet fuel of claim 18, comprising:
   about 65 vol. % to about 85 vol. % of one or more $C_{11}$-$C_{14}$ aliphatic hydrocarbons; and
   about 10 vol. % to about 20 vol. % of aromatic hydrocarbons.

20. The renewable jet fuel of claim 18, wherein the one or more $C_{11}$-$C_{14}$ aliphatic hydrocarbons comprise one or more pentamethylheptane isomers.

21. The renewable jet fuel of claim 18, wherein the one or more $C_{11}$-$C_{14}$ aliphatic hydrocarbons comprise one or more hydrocarbons selected from the group consisting of trimethylpentanes, pentamethylheptanes, tetramethyloctanes, heptamethylnonanes, trimethylnonanes, and combinations thereof; and the alkylated aromatic hydrocarbons comprise one or more mono- or dialkyl benzenes.

* * * * *